(12) United States Patent
Kuo et al.

(10) Patent No.: US 11,339,405 B2
(45) Date of Patent: May 24, 2022

(54) KIT AND METHOD FOR PRODUCING INDUCED EMBRYONIC NEURAL PROGENITORS

(71) Applicant: Academia Sinica, Taipei (TW)

(72) Inventors: Hung-Chih Kuo, Taipei (TW); Ching-Yu Chuang, Taipei (TW); Chan-Hsien Yeh, Taipei (TW)

(73) Assignee: ACADEMIA SINICA, Taipei (TW)

( * ) Notice: Subject to any disclaimer, the term of this patent is extended or adjusted under 35 U.S.C. 154(b) by 464 days.

(21) Appl. No.: 15/951,114

(22) Filed: Apr. 11, 2018

(65) Prior Publication Data

US 2018/0299430 A1 Oct. 18, 2018

Related U.S. Application Data

(60) Provisional application No. 62/484,409, filed on Apr. 12, 2017.

(51) Int. Cl.
| | |
|---|---|
| *C12N 15/85* | (2006.01) |
| *G01N 33/50* | (2006.01) |
| *C12N 5/079* | (2010.01) |
| *A61K 35/36* | (2015.01) |
| *C12N 5/09* | (2010.01) |
| *C12N 5/0793* | (2010.01) |
| *C12N 5/0797* | (2010.01) |
| *A61K 35/30* | (2015.01) |
| *C12N 15/86* | (2006.01) |
| *C12N 5/077* | (2010.01) |

(52) U.S. Cl.
CPC ............ *C12N 15/85* (2013.01); *A61K 35/30* (2013.01); *A61K 35/36* (2013.01); *C12N 5/0619* (2013.01); *C12N 5/0622* (2013.01); *C12N 5/0623* (2013.01); *C12N 5/0693* (2013.01); *C12N 15/86* (2013.01); *G01N 33/5058* (2013.01); *C12N 5/0656* (2013.01); *C12N 2320/10* (2013.01); *C12N 2500/38* (2013.01); *C12N 2501/60* (2013.01); *C12N 2501/602* (2013.01); *C12N 2503/02* (2013.01); *C12N 2506/03* (2013.01); *C12N 2506/1307* (2013.01); *C12N 2529/10* (2013.01); *G01N 2800/28* (2013.01)

(58) Field of Classification Search
CPC .... C12N 15/85; C12N 15/86; C12N 2503/02; G01N 2800/28
See application file for complete search history.

(56) References Cited

U.S. PATENT DOCUMENTS

| | | | | |
|---|---|---|---|---|
| 2012/0129262 | A1* | 5/2012 | West | C07K 14/4702 435/455 |
| 2014/0045915 | A1* | 2/2014 | Skog | C12Q 1/6886 514/44 A |
| 2014/0127814 | A1* | 5/2014 | Chandrasegaran | C12N 15/907 435/462 |
| 2019/0017032 | A1* | 1/2019 | Firas | C12N 5/0663 |
| 2019/0241633 | A1* | 8/2019 | Fotin-Mleczek | A61K 48/005 |

OTHER PUBLICATIONS

Peluso et al. Current Pharm. Design 20(6):1020-1024, 2014, abstract only. (Year: 2014).*
"Kit definition" google definition disclosure printed 2020 (Year: 2020).*
Choi et al. Molecular Brain 7, Article No. 17(2014). Printout dated Feb. 18, 2021 p. 1/34 (Year: 2014).*
Counsell et al. Scientific Reports 7, Article No. 44775 (2017). Printout dated Feb. 18, 20201 pp. 1/34 (Year: 2017).*
Brescia et al. Cell 2020, 9, 869, p. 1 of 24 (Year: 2020).*
Nasimuzzaman et al. Molecular Therapy—Methods & Clinical Development (2016) 3, 16071; doi:10.1038/mtm.2016.71. pp. 2-11 (Year: 2016).*

* cited by examiner

*Primary Examiner* — Marcia S Noble

(57) ABSTRACT

Disclosed herein are kits comprising transcription factors for inducing a fibroblast cell into an induced embryonic neural progenitor cell. The induced embryonic neural progenitor cell is then capable of differentiating into an astrocyte, an oligodendrocyte or a neuron. Also disclosed are the uses of the kit as a platform for selecting a drug candidate to treat neurological diseases.

2 Claims, 42 Drawing Sheets
(28 of 42 Drawing Sheet(s) Filed in Color)
Specification includes a Sequence Listing.

a)

b)

c)

a)

b)

a)

b)

c)

d)

SEQUENCE LISTING

<160> NUMBER OF SEQ ID NOS: 27

<210> SEQ ID NO 1
<211> LENGTH: 1599
<212> TYPE: DNA
<213> ORGANISM: Artificial Sequence
<220> FEATURE:
<223> OTHER INFORMATION: Synthesized CBX2 gene

<400> SEQUENCE: 1

```
atggaggagc tgagcagcgt gggcgagcag gtcttcgccg ccgagtgcat cctgagcaag      60
cggctccgca agggcaagct ggagtacctg gtcaagtggc gcggctggtc ctccaaacat     120
aacagctggg agccggagga gaacatcctg acccgaggc tgctcctggc cttccagaag     180
aaggaacatg agaaggaggt gcagaaccgg aagagaggca gaggccgag aggccggcca     240
aggaagctca ctgccatgtc ctcctgcagc cggcgctcca agctcaagga cccgatgct     300
ccctccaaat ccaagtccag cagttcctcc tcttcctcca cgtcatcctc ctcttcctca     360
gatgaagagg atgacagtga cttagatgct aagaggggtc cccggggccg cgagacccac     420
ccagtgccgc agaagaaggc ccagatcctg gtggccaaac ccgagctgaa ggatcccatc     480
cggaagaagc ggggacgaaa gcccctgccc cagagcaaa aggcaacccg aagacccgtg     540
agcctggcca aggtgctgaa gaccgcccgg aaggatctgg gggccccggc cagcaagctg     600
cccccctccac tcagcgcccc cgttgcaggc ctggcagctc tgaaggccca cgccaaggag     660
gcctgtggcg gccccagtgc catggccacc ccagagaacc tggccagcct aatgaagggc     720
atggccagta gccccggccg gggtggcatc agctggcaga gctccatcgt gcactacatg     780
aaccggatga cccagagcca ggcccaggct gccagcaggt tggcgctgaa ggcccaggcc     840
accaacaagt gcggcctcgg gctggacctg aaggtgagga cgcagaaagg ggagctggga     900
atgagccctc caggaagcaa aatcccgaag gcccccagcg gtggggctgt ggagcagaaa     960
gtggggaaca caggggggccc cccgcacacc catggtgcca gcagggtgcc tgctgggtgc    1020
ccaggccccc agccagcacc cacccaggag ctgagcctcc aggtcttgga cttgcagagt    1080
gtcaagaatg gcatgcccgg ggtgggtctc cttgcccgcc acgccaccgc caccaagggt    1140
gtcccggcca ccaacccagc ccctgggaag ggcactggga gtggcctcat tggggccagc    1200
ggggccacca tgcccaccga cacaagcaaa agtgagaagc tggcttccag agcagtggcg    1260
ccacccaccc ctgccagcaa gagggactgt gtcaagggca gtgctacccc cagtgggcag    1320
gagagccgca cagcccccgg agaagcccgc aaggcggcca cactgccaga gatgagcgca    1380
ggtgaggaga gtagcagctc ggactccgac cccgactccg cctcgccgcc cagcactgga    1440
cagaacccat cagtgtccgt tcagaccagc caggactgga gcccacccg cagcctcatc    1500
gagcacgtat ttgtcaccga cgtcactgcc aacctcatca ccgtcacagt gaaggagtct    1560
cccaccagcg tgggcttctt caacctgagg cattactga                          1599
```

<210> SEQ ID NO 2
<211> LENGTH: 843
<212> TYPE: DNA
<213> ORGANISM: Artificial Sequence
<220> FEATURE:
<223> OTHER INFORMATION: Synthesized HES1 gene

<400> SEQUENCE: 2

```
atgccagctg atataatgga gaaaaattcc tcgtccccgg tggctgctac cccagccagt     60
gtcaacacga caccggataa accaaagaca gcatctgagc acagaaagtc atcaaagcct    120
```

| | |
|---|---|
| attatggaga aaagacgaag agcaagaata aatgaaagtc tgagccagct gaaaacactg | 180 |
| attttggatg ctctgaagaa agatagctcg cggcattcca agctggagaa ggcggacatt | 240 |
| ctggaaatga cagtgaagca cctccggaac ctgcagcggg cgcagatgac ggctgcgctg | 300 |
| agcacagacc caagtgtgct ggggaagtac cgagccggct tcagcgagtg catgaacgag | 360 |
| gtgacccgct tcctgtccac gtgcgagggc gttaataccg aggtgcgcac tcggctgctc | 420 |
| ggccacctgg ccaactgcat gacccagatc aatgccatga cctacccggg cagccgcac | 480 |
| cccgccttgc aggcgccgcc accgccccca ccgggacccg gcggccccca gcacgcgccg | 540 |
| ttcgcgccgc cgccgccact cgtgcccatc cccgggggcg cggcgccccc tcccggcggc | 600 |
| gcccctgca agctgggcag ccaggctgga gaggcggcta aggtgtttgg aggcttccag | 660 |
| gtggtaccgg ctcccgatgg ccagtttgct ttcctcattc ccaacggggc cttcgcgcac | 720 |
| agcggccctg tcatccccgt ctacaccagc aacagcggca cctccgtggg ccccaacgca | 780 |
| gtgtcaccct tccagcggcc ctcgcttacg gcggactcca tgtggaggcc gtggcggaac | 840 |
| tga | 843 |

<210> SEQ ID NO 3
<211> LENGTH: 468
<212> TYPE: DNA
<213> ORGANISM: Artificial Sequence
<220> FEATURE:
<223> OTHER INFORMATION: Synthesized ID1 gene

<400> SEQUENCE: 3

| | |
|---|---|
| atgaaagtcg ccagtggcag caccgccacc gccgccgcgg gccccagctg cgcgctgaag | 60 |
| gccggcaaga cagcgagcgg tgcgggcgag gtggtgcgct gtctgtctga gcagagcgtg | 120 |
| gccatctcgc gctgcgccgg gggcgccggg gcgcgcctgc ctgccctgct ggacgagcag | 180 |
| caggtaaacg tgctgctcta cgacatgaac ggctgttact cacgcctcaa ggagctggtg | 240 |
| cccaccctgc cccagaaccg caaggtgagc aaggtggaga ttctccagca cgtcatcgac | 300 |
| tacatcaggg accttcagtt ggagctgaac tcggaatccg aagttggaac ccccgggggc | 360 |
| cgagggctgc cggtccgggc tccgctcagc accctcaacg gcgagatcag cgccctgacg | 420 |
| gccgaggcgg catgcgttcc tgcggacgat cgcatcttgt gtcgctga | 468 |

<210> SEQ ID NO 4
<211> LENGTH: 1296
<212> TYPE: DNA
<213> ORGANISM: Artificial Sequence
<220> FEATURE:
<223> OTHER INFORMATION: Synthesized TFAP2A gene

<400> SEQUENCE: 4

| | |
|---|---|
| atgttagttc acagtttttc agccatggac cgtcacgacg gcaccagcaa cgggacggca | 60 |
| cggttgcccc agctgggcac tgtaggtcaa tctccctaca cgagcgcccc gccgctgtcc | 120 |
| cacaccccca atgccgactt ccagccccca tacttccccc accctaccca gcctatctac | 180 |
| ccccagtcgc aagatcctta ctcccacgtc aacgacccct acagcctgaa ccccctgcac | 240 |
| gcccagccgc agccgcagca cccaggctgg cccggccaga gcagagcca ggagtctggg | 300 |
| ctcctgcaca cgcaccgggg gctgcctcac cagctgtcgg gcctggatcc tcgcagggac | 360 |
| tacaggcggc acgaggacct cctgcacggc ccacacgcgc tcagctcagg actcggagac | 420 |
| ctctcgatcc actccttacc tcacgccatc gaggaggtcc cgcatgtaga agacccgggt | 480 |

| | |
|---|---:|
| attaacatcc cagatcaaac tgtaattaag aaaggccccg tgtccctgtc caagtccaac | 540 |
| agcaatgccg tctccgccat ccctattaac aaggacaacc tcttcggcgg cgtggtgaac | 600 |
| cccaacgaag tcttctgttc agttccgggt cgcctctcgc tcctcagctc cacctcgaag | 660 |
| tacaaggtca cggtggcgga agtgcagcgg cggctctcac cacccgagtg tctcaacgcg | 720 |
| tcgctgctgg gcggagtgct ccggagggcg aagtctaaaa atggaggaag atctttaaga | 780 |
| gaaaaactgg acaaaatagg attaaatctg cctgcaggga gacgtaaagc tgccaacgtt | 840 |
| accctgctca catcactagt agagggagaa gctgtccacc tagccaggga ctttgggtac | 900 |
| gtgtgcgaaa ccgaatttcc tgccaaagca gtagctgaat tctcaaccg acaacattcc | 960 |
| gatcccaatg agcaagtgac aagaaaaaac atgctcctgg ctacaaaaca gatatgcaaa | 1020 |
| gagttcaccg acctgctggc tcaggaccga tctcccctgg ggaactcacg cccaacccc | 1080 |
| atcctggagc ccggcatcca gagctgcttg acccacttca acctcatctc ccacggcttc | 1140 |
| ggcagcccg cggtgtgtgc cgcggtcacg gccctgcaga actatctcac cgaggccctc | 1200 |
| aaggccatgg acaaaatgta cctcagcaac aaccccaata gccacacgga caacaacgcc | 1260 |
| aaaagcagtg acaaagagga gaagcacaga aagtga | 1296 |

<210> SEQ ID NO 5
<211> LENGTH: 933
<212> TYPE: DNA
<213> ORGANISM: Artificial Sequence
<220> FEATURE:
<223> OTHER INFORMATION: Synthesized ZFP42 gene

<400> SEQUENCE: 5

| | |
|---|---:|
| atgagccagc aactgaagaa acgggcaaag acaagacacc agaaaggcct gggtggaaga | 60 |
| gccccagtg gggctaagcc caggcaaggc aagtcaagcc aagacctgca ggcggaaata | 120 |
| gaacctgtca gcgcggtgtg ggccttatgt gatggctatg tgtgctatga gcctggccct | 180 |
| caggctctcg gagggatga tttctcagac tgttacatag aatgcgtcat aagggggtgag | 240 |
| ttttctcaac ccatcctgga agaggactca cttttgagt ccttggaata cctaaagaaa | 300 |
| ggatcagaac aacagctttc tcaaaaggtt ttcgaagcaa gctcccttga atgttctttg | 360 |
| gaatacatga aaaagggggt aaagaaagag cttccacaaa agatagttgg agagaattcg | 420 |
| cttgagtatt ctgagtacat gacaggcaag aagcttccgc ctggaggaat acctggcatt | 480 |
| gacctatcag atcctaaaca gctcgcagaa tttgctagaa agaagccccc cataaataaa | 540 |
| gaatatgaca gtctgagcgc aatcgcttgt cctcagagtg gatgcactag gaagttgagg | 600 |
| aatagagctg ccctgagaaa gcatctcctc attcatggtc cccgagacca cgtctgtgcg | 660 |
| gaatgtggga agcgttcgt tgagagctca aaactaaaga acatttcct ggttcatact | 720 |
| ggagagaagc cgtttcggtg cacttttgaa gggtgcggaa agcgcttctc tctggacttt | 780 |
| aatttgcgta cgcacgtgcg catccacacg ggggagaaac gtttcgtgtg tcccttcaa | 840 |
| ggctgcaaca ggaggtttat tcagtcaaat aacctgaaag cccacatcct aacgcatgca | 900 |
| aatacgaaca agaatgaaca agagggaaag tag | 933 |

<210> SEQ ID NO 6
<211> LENGTH: 3855
<212> TYPE: DNA
<213> ORGANISM: Artificial Sequence
<220> FEATURE:
<223> OTHER INFORMATION: Synthesized ZNF423 gene

<400> SEQUENCE: 6

```
atgcataaga agagggttga agaggggag gcctcagact tctcgctggc ctgggattcc      60
tccgtgacag cagcaggagg cctagaagga gagccagagt gcgatcagaa aaccagccgt    120
gcgctggaag acaggaacag cgtgacaagt caagaggaga gaaatgagga tgatgaagac    180
atggaggatg aatcaattta cacctgcgat cactgtcagc aggacttcga gtctctggca    240
gacctgacgg accaccgggc ccaccgctgt cctggagatg gtgatgacga cccacaactc    300
tcctgggtgg cctcgtctcc ctccagcaag gatgttgcgt cacccacgca gatgatcgga    360
gatggttgtg acctcggcct cggcgaggag gaaggggca cgggcctgcc atacccttgc    420
cagttctgcg acaagtcctt catccgcttg agctacttga gaggcacga gcagatccac    480
agcgacaagc tgccgttcaa gtgcacctac tgcagccgcc tcttcaagca caggaggagc    540
cgtgaccgga catcaagct gcatacgggc gacaagaagt atcactgcca cgagtgcgag    600
gcagccttct cccgcagcga ccacctcaag atccacctga gacccacag ctccagcaag    660
cccttcaagt gcactgtgtg caagcgcggc ttctcctcca ccagctcgct gcagagccac    720
atgcaggccc acaaaaagaa caaggagcat ctggccaagt cggagaagga agccaagaag    780
gacgacttca tgtgcgacta ctgcgaggac acccttcagcc agacggagga gctggagaag    840
cacgtgctca cccgccaccc gcagctgtcc gagaaggcgg acctgcagtg cattcactgc    900
cctgaggtct tcgtcgacga gaacacactg ctcgcccata tccaccaagc ccacgccaac    960
cagaaacaca agtgccccat gtgccctgag cagttctcct cagtggaagg tgtctactgc   1020
cacctggaca gccaccggca gcccgactcc agcaaccaca gtgtcagtcc cgaccctgta   1080
ctgggcagcg tggcctccat gagcagcgcc acacccgact ccagcgcctc tgtggagcgt   1140
ggctccaccc cggactccac cttgaagccg ctgcggggc agaagaagat gcgggatgac   1200
gggcagggct ggaccaaggt ggtctatagc tgcccctatt gttccaagcg ggactttaac   1260
agcctggccg tgctggagat ccacctgaag accatccacg cggacaagcc ccagcagagc   1320
cacacatgtc agatctgcct ggactccatg cccacccctct acaacctcaa cgagcacgtt   1380
cgcaagctgc acaagaacca tgcctaccct gtgatgcagt ttggcaacat ctctgccttc   1440
cactgcaact actgccccga tgtgttcgcc gacatcaata gcctgcagga gcacatccgc   1500
gtctcccact gcggccccaa cgccaacccc tctgacggta ataatgcttt cttctgcaac   1560
cagtgctcca tgggtttcct tactgagtcc tccctcaccg agcacatcca gcaggccac   1620
tgcagtgtgg gcagtgccaa actagagtct ccggtggtgc agcccacgca gtccttcatg   1680
gaggtctatt cctgcccta ctgcaccaac tcccccatct ttggctccat cctgaaactc   1740
accaagcaca tcaaggagaa ccacaagaac attccactgg cccacagcaa gaagtccaag   1800
gccgagcaga gcccagtctc gtccgatgtg gaggtgtctt cccgaagcg gcagcggctc   1860
tcagcaagcg ccaactccat ctccaatggg gagtatcctt gcaatcaatg cgacctcaag   1920
ttctccaact tgagagctt ccagacccac ctgaagctgc acctggagct gctgctgcgg   1980
aagcaagcgt gccccagtg caaagaggac tttgactccc aggagtccct cctgcagcac   2040
ctgacagtgc attacatgac cacgtcgacc cactatgtgt gcgagagctg cgacaagcaa   2100
ttttcctcgg tggatgacct gcagaagcac ctgctggaca tgcacaccct tgtgttgtac   2160
cactgcaccc tgtgtcagga ggtcttcgac tccaaggtgt ccatccaggt gcacctggcg   2220
gtgaagcaca gcaatgagaa gaagatgtac cgctgcacgg cctgcaactg ggacttccgc   2280
aaggaggctg acctgcaggt gcacgtcaaa cacagccacc tgggcaaccc ggccaaggct   2340
```

| | |
|---|---:|
| cacaagtgca tcttctgtgg ggagaccttc agcaccgagg tggagctgca gtgccacatc | 2400 |
| accacacaca gcaagaagta taactgtaag ttctgcagca aggccttcca cgccatcatc | 2460 |
| ctgctggaga agcacctgcg ggagaagcac tgtgtgtttg atgctgcgac cgagaacggc | 2520 |
| acggccaatg gggtaccccc aatggccacc aagaaagctg agcctgctga cctgcagggc | 2580 |
| atgctgctta agaaccctga ggcacctaac agccatgagg ccagcgagga tgacgtggac | 2640 |
| gcgtcggagc ccatgtacgg ctgtgacatc tgtggggcgg cctacaccat ggaggtgctg | 2700 |
| ctgcagaatc accggctgcg ggaccacaat atccggccgg gcgaggatga tggctcacgc | 2760 |
| aagaaggctg agtttatcaa gggcagtcac aagtgcaacg tttgttcacg gactttcttc | 2820 |
| tcggagaacg ggctacggga gcacctgcag acgcaccggg gccctgccaa gcactacatg | 2880 |
| tgtcccatct gtggtgagcg cttcccttcg ctgctgacgc tcaccgaaca caaggtgacc | 2940 |
| cacagcaaga gcctggacac gggcacctgt cgcatctgca agatgcccct gcagagcgag | 3000 |
| gaggagttta ttgagcactg ccagatgcac cctgacctgc gcaactcact cacgggcttc | 3060 |
| cgctgtgtgg tctgcatgca gacagtcact tccacgcttg agctcaagat ccatggcacc | 3120 |
| ttccacatgc agaagctggc gggcagctca gcggcgtcct cccccaatgg ccaggggctg | 3180 |
| cagaagctct acaagtgcgc cctgtgcctc aaggagttcc gcagcaagca ggacctggtg | 3240 |
| aagcttgacg tcaatgggct gccctacggc ctctgcgccg gctgcatggc ccgcagcgcc | 3300 |
| aacggacagg tgggtggcct ggccccgccc gagcccgccg accggccctg tgccggcctc | 3360 |
| cgttgccccg agtgcagtgt caagtttgag agtgccgaag acctggagag ccacatgcag | 3420 |
| gtggaccacc gtgacctcac gccggagacc agtgggcccc ggaaaggcac ccagacatcg | 3480 |
| ccagtgcccc ggaaaaagac ataccagtgc atcaagtgcc agatgacctt cgagaacgag | 3540 |
| agagagatcc aaatccacgt tgccaaccac atgattgagg aaggcatcaa ccacgagtgt | 3600 |
| aagctgtgca accagatgtt cgactccccg gccaagctcc tctgtcacct cattgagcac | 3660 |
| agcttcgagg gcatgggcgg cacccttcaaa tgccccgtgt gtttcacagt cttcgtccag | 3720 |
| gccaacaagt tgcagcagca catctttgcc gtgcacgggc aggaggacaa gatctacgac | 3780 |
| tgctcacagt gccctcagaa gttcttcttc cagaccgagc tgcagaacca cacgatgagc | 3840 |
| cagcacgcac agtga | 3855 |

<210> SEQ ID NO 7
<211> LENGTH: 2127
<212> TYPE: DNA
<213> ORGANISM: Artificial Sequence
<220> FEATURE:
<223> OTHER INFORMATION: Synthesized DACH1 gene

<400> SEQUENCE: 7

| | |
|---|---:|
| atggcagtgc cggcggcttt gatccctccg acccagctgg tcccccctca acccccaatc | 60 |
| tccacgtctg cttcctcctc tggcaccacc acctccacct cttcggcgac ttcgtctccg | 120 |
| gctccttcca tcggacccccc ggcgtcctct gggccaactc tgttccgccc ggagcccatc | 180 |
| gcttcggcgg cggcggcggc ggccacagtc acctctaccg gcggcggcgg cggcggcggc | 240 |
| ggcggcggca gcgaggcgg cggcggcagc agcggcaacg aggcggcgg tggcggcggc | 300 |
| ggcggtggca gcaactgcaa ccccaacctg gcggccgcga gcaacggcag cggcggcggc | 360 |
| ggcggcggca tcagcgctgg cggcggcgtc gcttccagca cccccatcaa cgccagcacc | 420 |
| ggcagcagca gcagcagcag tagcagcagc agcagcagca gcagtagtag cagcagcagc | 480 |
| agtagcagca gcagctgcgg cccccctcccc gggaaacccg tgtactcaac cccgtcccca | 540 |

```
gtggaaaaca cccctcagaa taatgagtgc aaaatggtgg atctgagggg ggccaaagtg      600
gcttccttca cggtggaggg ctgcgagctg atctgcctgc cccaggcttt cgacctgttc      660
ctgaagcact tggtggggggg cttgcatacg gtctacacca agctgaagcg gctggagatc      720
acgccggtgg tgtgcaatgt ggaacaagtt cgcatcctga ggggactggg cgccatccag      780
ccaggagtga accgctgcaa actcatctcc aggaaggact tcgagaccct ctacaatgac      840
tgcaccaacg caagttctag acctggaagg cctcctaaga ggactcaaag tgtcacctcc      900
ccagagaact ctcacatcat gccgcattct gtccctggtc tcatgtctcc tgggataatt      960
ccaccaacag gtctgacagc agccgctgca gcagctgctg ctgctaccaa tgcagctatt     1020
gctgaagcaa tgaaggtgaa aaaaatcaaa ttagaagcca tgagcaacta tcatgccagt     1080
aataaccaac atggagcaga ctctgaaaac ggggacatga attcaagtgt cggactggaa     1140 cttccttttta tgatgatgcc ccaccctcta attcctgtca gcctacctcc agcatctgtc     1200
accatggcaa tgagccagat gaaccacctc agcaccattg caaatatggc agcagcagca     1260
caagttcaga gtcccccatc cagagttgag acatcagtta ttaaggagcg tgttcctgat     1320
agcccctcac ctgcccccctc tctggaggag gggagaaggc ctggcagtca cccatcatca     1380
catcgcagca gcagcgtgtc cagctcccct gctcggactg agagctcttc tgacagaatc     1440
ccggtccatc agaatgggtt gtccatgaac cagatgctga tgggcttatc accaaatgta     1500
cttcctgggc ccaaagaggg agatttggcc ggtcatgaca tgggacatga gtcaaaaagg     1560
atgcatattg aaaagatga gacccccgctt tctacaccaa ccgcaagaga cagccttgac     1620
aaactctctc taactgggca tggacaacca ctgcctccag gttttccatc tcctttttctg     1680 tttcctgatg gactgtcttc catcgagact cttctgacta acatacaggg gctgttgaaa     1740
gttgccatag ataatgccag agctcaagag aaacaggtcc aactggaaaa aactgagctg     1800
aagatggatt tttaaggga agagaactaa gggaaacac ttgagaagca gttggctatg     1860
gaacaaaaga atagagccat agttcaaaag aggctaaaga aggagaagaa ggcaaagaga     1920
aaattgcagg aagcacttga gtttgagacg aaacggcgtg aacaagcaga acagacgcta     1980
aaacaggcag cttcaacaga tagtctcagg gtcttaaatg actctctgac cccagagata     2040
gaggctgacc gcagtggcgg cagaacagat gctgaaagga caatacaaga tggaagactg     2100
tatttgaaaa ctactgtcat gtactga                                          2127

<210> SEQ ID NO 8
<211> LENGTH: 1470
<212> TYPE: DNA
<213> ORGANISM: Artificial Sequence
<220> FEATURE:
<223> OTHER INFORMATION: Synthesized FOXG1 gene

<400> SEQUENCE: 8
atgctggaca tggagatag gaaagaggtg aaaatgatcc caagtcctc gttcagcatc        60 aacagcctgg tgcccgaggc ggtccagaac gacaaccacc acgcgagcca cggccaccac      120
aacagccacc accccccagca ccaccaccac caccaccacc atcaccacca cccgccgccg      180
cccgccccgc aaccgccgcc gccgccgcag cagcagcagc gccgccgcc gccgcccccg      240 gcaccgcagc cccccagac gcggggcgcc ccggcgcccg acgacgacaa gggcccccag      300
cagctgctgc tcccgccgcc gccaccgcca ccacgccccg ccgccctgga cggggctaaa      360
gcggacgggc tgggcggcaa gggcgagccg ggcggcgggc cggggagct ggcgcccgtc      420
```

| | |
|---|---|
| gggccggacg agaaggagaa gggcgccggc gccggggggg aggagaagaa ggggcgggc | 480 |
| gagggcggca aggacgggga gggggcaag gagggcgaga agaagaacgg caagtacgag | 540 |
| aagccgccgt tcagctacaa cgcgctcatc atgatggcca tccggcagag ccccgagaag | 600 |
| cggctcacgc tcaacggcat ctacgagttc atcatgaaga acttccctta ctaccgcgag | 660 |
| aacaagcagg gctggcagaa ctccatccgc acaatctgt ccctcaacaa gtgcttcgtg | 720 |
| aaggtgccgc ccactacga cgacccgggc aagggcaact actggatgct ggacccgtcg | 780 |
| agcgacgacg tgttcatcgg cggcaccacg ggcaagctgc ggcgccgctc caccacctcg | 840 |
| cgggccaagc tggccttcaa cgcggtgcg cgcctcacct ccaccggcct caccttcatg | 900 |
| gaccgcgccg gctccctcta ctggcccatg tcgcccttcc tgtccctgca ccaccccgc | 960 |
| gccagcagca ctttgagtta caacggcacc acgtcggcct accccagcca ccccatgccc | 1020 |
| tacagctccg tgttgactca gaactcgctg ggcaacaacc actccttctc caccgccaac | 1080 |
| ggcctgagcg tggaccggct ggtcaacggg agatcccgt acgccacgca ccacctcacg | 1140 |
| gccgccgcgc tagccgcctc ggtgcccctgc ggcctgtcgg tgcccctgctc tgggacctac | 1200 |
| tccctcaacc cctgctccgt caacctgctc gcgggccaga ccagttactt tttccccac | 1260 |
| gtcccgcacc cgtcaatgac ttcgcagagc agcacgtcca tgagcgccag ggccgcgtcc | 1320 |
| tcctccacgt cgccgcaggc ccctcgacc ctgccctgtg agtctttaag accctctttg | 1380 |
| ccaagtttta cgacgggact gtctggggga ctgtctgatt atttcacaca tcaaaatcag | 1440 |
| gggtcttctt ccaacccttt aatacattaa | 1470 |

<210> SEQ ID NO 9
<211> LENGTH: 1395
<212> TYPE: DNA
<213> ORGANISM: Artificial Sequence
<220> FEATURE:
<223> OTHER INFORMATION: Synthesized MYCN gene

<400> SEQUENCE: 9

| | |
|---|---|
| atgccgagct gctccacgtc caccatgccg ggcatgatct gcaagaaccc agacctcgag | 60 |
| tttgactcgc tacagccctg cttctacccg gacgaagatg acttctactt cggcggcccc | 120 |
| gactcgaccc ccccggggga ggacatctgg aagaagtttg agctgctgcc cacgcccccg | 180 |
| ctgtcgccca gccgtggctt cgcggagcac agctccgagc cccgagctg gtcacggag | 240 |
| atgctgcttg agaacgagct gtggggcagc ccggccgagg aggacgcgtt cggcctgggg | 300 |
| ggactgggtg gcctcacccc caacccggtc atcctccagg actgcatgtg gagcggcttc | 360 |
| tccgcccgcg agaagctgga gcgcgccgtg agcgagaagc tgcagcacgg ccgcgggccg | 420 |
| ccaaccgccg gttccaccgc ccagtccccg ggagccggcg ccgccagccc tgcgggtcgc | 480 |
| gggcacggcg gggctgcggg agccggccgc gccggggccg ccctgcccgc cgagctcgcc | 540 |
| cacccggccg ccgagtgcgt ggatcccgcc gtggtcttcc cctttcccgt gaacaagcgc | 600 |
| gagccagcgc ccgtgcccgc agccccgcc agtgccccgg cggcgggccc tgcggtcgcc | 660 |
| tcggggggcgg gtattgccgc cccagccggg gccccggggg tcgcccctcc gcgcccaggc | 720 |
| ggccgccaga ccagcggcgg cgaccacaag gccctcagta cctccggaga ggacaccctg | 780 |
| agcgattcag atgatgaaga tgatgaagag gaagatgaag aggaagaaat cgacgtggtc | 840 |
| actgtggaga gcggcgttc ctcctccaac accaaggctg tcaccacatt caccatcact | 900 |
| gtgcgtccca gaacgcagc cctgggtccc ggagggctc agtccagcga gctgatcctc | 960 |
| aaacgatgcc ttcccatcca ccagcagcac aactatgccg ccccctctcc ctacgtggag | 1020 |

```
agtgaggatg caccccccaca gaagaagata aagagcgagg cgtccccacg tccgctcaag    1080
agtgtcatcc ccccaaaggc taagagcttg agccccgaa actctgactc ggaggacagt     1140
gagcgtcgca gaaaccacaa catcctggag cgccagcgcc gcaacgacct tcggtccagc    1200
tttctcacgc tcagggacca cgtgccgag ttggtaaaga atgagaaggc cgccaaggtg     1260
gtcattttga aaaaggccac tgagtatgtc cactccctcc aggccgagga gcaccagctt    1320
ttgctggaaa aggaaaaatt gcaggcaaga cagcagcagt tgctaaagaa aattgaacac    1380
gctcggactt gctag                                                     1395
```

<210> SEQ ID NO 10
<211> LENGTH: 1245
<212> TYPE: DNA
<213> ORGANISM: Artificial Sequence
<220> FEATURE:
<223> OTHER INFORMATION: Synthesized NR2F2 gene

<400> SEQUENCE: 10

```
atggcaatgg tagtcagcac gtggcgcgac ccccaggacg aggtgcccgg ctcacagggc    60
agccaggcct cgcaggcgcc gcccgtgccc ggccgccgc ccggcgcccc gcacacgcca     120
cagacgcccg gccaaggggg cccagccagc acgccagccc agacggcggc cggtggccag    180
ggcggccctg gcggcccggg tagcgacaag cagcagcagc agcaacacat cgagtgcgtg    240
gtgtgcggag acaagtcgag cggcaagcac tacggccagt tcacgtgcga gggctgcaag    300
agcttcttca gcgcagcgt gcggaggaac ctgagctaca cgtgccgcgc caaccggaac    360
tgtcccatcg accagcacca tcgcaaccag tgccagtact gccgcctcaa aaagtgcctc    420
aaagtgggca tgagacggga gcggtgcag aggggcagga tgccgccgac ccagccgacc    480
cacgggcagt tcgcgctgac caacgggat cccctcaact gccactcgta cctgtccgga    540
tatatttccc tgctgttgcg cgcggagccc tatcccacgt cgcgcttcgg cagccaatgc    600
atgcagccca acaacatcat gggtatcgag aacatttgcg aactggccgc gaggatgctc    660
ttcagcgccg tcgagtgggc ccggaacatc cccttcttcc ccgacctgca gatcacggac    720
caggtggccc tgcttcgcct cacctggagc gagctgtttt gttgaatgc ggcgcagtgc    780 tccatgcccc tccacgtcgc cccgctcctg gccgccgccg gctgcatgc ttcgcccatg    840 tccgccgacc gggtggtcgc ctttatggac acatacgga tcttccaaga gcaagtggag    900
aagctcaagg cgctgcacgt tgactcagcc gagtacagct gcctcaaggc catagtcctg    960
ttcacctcag atgcctgtgg tctctctgat gtagcccatg tggaaagctt gcaggaaaag    1020
tctcagtgtg ctttggaaga atacgttagg agccagtacc ccaaccagcc gacgagattc    1080
ggaaagcttt tgcttcgcct cccttccctc cgcaccgtct cctcctcagt catagagcaa    1140 ttgttttttcg tccgtttggt aggtaaaacc cccatcgaaa ccctcatccg ggatatgtta    1200
ctgtccggca gcagttttaa ctggccgtat atggcaattc aataa                    1245
```

<210> SEQ ID NO 11
<211> LENGTH: 1443
<212> TYPE: DNA
<213> ORGANISM: Artificial Sequence
<220> FEATURE:
<223> OTHER INFORMATION: Synthesized NR6A1 gene

<400> SEQUENCE: 11

```
atggagcggg acgaaccgcc gcctagcgga ggggggaggcg gcgggggctc ggcggggttc    60
```

```
ctggagcctc cgccgcgct ccctccgccg ccgcgcaacg gtttctgtca ggatgaattg    120
gcagagcttg acccaggcac tatttctgtt tcagatgatc gggctgaaca acgaacctgt   180
ctcatttgtg gggaccgcgc tacaggcttg cactatggga tcatctcctg tgagggctgc   240
aaagggtttt tcaagcggag catttgcaac aaacgggtat atcgatgcag tcgtgacaag   300
aactgtgtca tgtctcggaa gcagaggaac aggtgccagt actgccgcct gctcaaatgc   360
ctccagatgg ggatgaaccg gaaggctatc agagaagatg gcatgcctgg aggccggaat   420
aagagcattg ggccagtcca gatatcggaa gaagaaatcg aaaggatcat gtctgggcag   480
gagtttgagg aagaggccaa tcactggagc aaccatggtg atagtgacca cagttcccct   540
gggaacaggg cttcggagag caaccagccc tcaccaggct ccacactgtc ttccagtagg   600
tctgtggaac tgaatggatt catggccttc agggaacagt acatgggaat gtctgtgcct   660
ccacattacc aatatatacc gcacctttt agctattctg ccactcacc acttctgccc    720
caacaagctc gcagcctgga tccccagtca tacagtctga ttcaccagct gttatcagcc   780
gaggacctgg aaccattggg cacgcccatg ttgattgaag atggatacgc tgtgacacag   840
gcagaactat ttgccctgct ttgccgcctg ccgacgagc tgctctttag cagattgcc    900
tggatcaaga aactgccttt cttctgcgag ctctcaatca aggattacac gtgcctcttg   960
agctctacgt ggcaggagct aatcctgctg tcttccctca ccgtttacag caagcagatc  1020
tttgggaac tggctgatgt cactgccaag tactcgccct ccgatgaaga actcacagag  1080
tttagtgatg aagggatgga ggtgatcgag cggctcatct acctctatca caagttccat  1140
cagctaaagg tcagcaacga ggagtatgct tgcatgaaag caattaactt cctaaatcaa  1200
gatatcaggg gtctgaccag tgcctcacag ctggaacaat tgaataaacg atactggtac  1260
atttgccagg attttactga atataaatac acacatcagc cgaaccgctt tcctgatctc  1320
atgatgtgct tacctgagat tcgatatatt gcaggaaaga tggtgaatgt gcccctggag  1380
cagctgcccc tcctctttaa ggtggtgctg cattcctgca agaccagtgt gggcaaggaa  1440
tga                                                                1443
```

```
<210> SEQ ID NO 12
<211> LENGTH: 954
<212> TYPE: DNA
<213> ORGANISM: Artificial Sequence
<220> FEATURE:
<223> OTHER INFORMATION: Synthesized SOX2 gene

<400> SEQUENCE: 12
```

```
atgtacaaca tgatggagac ggagctgaag ccgccgggcc cgcagcaaac ttcgggggc    60
ggcggcggca actccaccgc ggcggcggcc ggcggcaacc agaaaaacag cccgaccgc   120
gtcaagcggc ccatgaatgc cttcatggtg tggtcccgcg ggcagcggcg caagatggcc   180
caggagaacc ccaagatgca caactcggag atcagcaagc gcctgggcgc cgagtggaaa   240
cttttgtcgg agacggagaa gcggccgttc atcgacgagc taagcggct gcgagcgctg   300
cacatgaagg agcacccgga ttataaatac cggccccggc ggaaaaccaa gacgctcatg   360
aagaaggata gtacacgct gccggcgggg ctgctggccc ccggcggcaa tagcatggcg   420
agcggggtcg gggtgggcgc cggcctgggc gcgggcgtga accagcgcat ggacagttac   480
gcgcacatga acggctggag caacggcagc tacagcatga tgcaggacca gctgggctac   540
ccgcagcacc cgggcctcaa tgcgcacggc gcagcgcaga tgcagcccat gcaccgctac   600
gacgtgagcg ccctgcagta caactccatg accagctcgc agacctacat gaacggctcg   660
```

```
cccacctaca gcatgtccta ctcgcagcag ggcacccctg gcatggctct tggctccatg    720
ggttcggtgg tcaagtccga ggccagctcc agcccccctg tggttacctc ttcctcccac    780
tccagggcgc cctgccaggc cggggacctc cgggacatga tcagcatgta tctccccggc    840
gccgaggtgc cggaacccgc cgcccccagc agacttcaca tgtcccagca ctaccagagc    900
ggcccggtgc ccggcacggc cattaacggc acactgcccc tctcacacat gtga          954
```

<210> SEQ ID NO 13
<211> LENGTH: 1326
<212> TYPE: DNA
<213> ORGANISM: Artificial Sequence
<220> FEATURE:
<223> OTHER INFORMATION: Synthesized SOX11 gene

<400> SEQUENCE: 13

```
atggtgcagc aggcggagag cttggaagcg agagcaacc tgccccggga ggcgctggac      60
acggaggagg gcgaattcat ggcttgcagc ccggtggccc tggacgagag cgacccagac    120
tggtgcaaga cggcgtcggg ccacatcaag cggccgatga acgcgttcat ggtatggtcc    180
aagatcgaac gcaggaagat catggagcag tctccggaca tgcacaacgc cgagatctcc    240
aagaggctgg gcaagcgctg gaaaatgctg aaggacagcg agaagatccc gttcatccgg    300
gaggcggagc ggctgcggct caagcacatg gccgactacc ccgactacaa gtaccggccc    360
cggaaaaagc ccaaaatgga cccctcggcc aagcccagcg ccagccagag cccagagaag    420
agcgcggccg gcggcggcgg cgggagcgcg ggcggaggcg cgggcggtgc caagacctcc    480
aagggctcca gcaagaaatg cggcaagctc aaggcccccg cggccgcggg cgccaaggcg    540
ggcgcgggca aggcggccca gtccggggac tacgggggcg cgggcgacga ctacgtgctg    600
ggcagcctgc gcgtgagcgg ctcggcggc ggcggcgcgg gcaagacggt caagtgcgtg    660
tttctggatg aggacgacga cgacgacgac gacgacgacg agctgcagct gcagatcaaa    720
caggagccgg acgaggagga cgaggaacca ccgcaccagc agctcctgca gccgccgggg    780
cagcagccgt cgcagctgct gagacgctac aacgtcgcca agtgcccgc cagccctacg    840 ctgagcagct cggcggagtc ccccgaggga gcgagcctct acgacgaggt gcgggccggc    900
gcgacctcgg gcgccggggg cggcagccgc ctctactaca gcttcaagaa catcaccaag    960
cagcacccgc cgccgctcgc gcagcccgcg ctgtcgcccg cgtcctcgcg ctcggtgtcc    1020
acctcctcgt ccagcagcag cggcagcagc agcggcagca gcggcgagga cgccgacgac   1080
ctgatgttcg acctgagctt gaatttctct caaagcgcgc acagcgccag cgagcagcag   1140
ctggggggcg cgcggcggc cgggaacctg tccctgtcgc tggtggataa ggatttggat   1200
tcgttcagcg agggcagcct gggctcccac ttcgagttcc ccgactactg cacgccggag   1260
ctgagcgaga tgatcgcggg ggactggctg gaggcgaact tctccgacct ggtgttcaca   1320
tattga                                                              1326
```

<210> SEQ ID NO 14
<211> LENGTH: 1599
<212> TYPE: DNA
<213> ORGANISM: Artificial Sequence
<220> FEATURE:
<223> OTHER INFORMATION: Synthesized ZIC2 gene

<400> SEQUENCE: 14

```
atgctcctgg acgcgggtcc gcagttcccg gccatcgggg tgggcagctt cgcgcgccac     60
```

| | |
|---|---:|
| catcaccact ccgccgcggc ggcggcggcg gctgccgccg agatgcagga ccgtgaactg | 120 |
| agcctggcgg cggcgcagaa cggcttcgtt gactccgccg ccgcgcacat gggagccttc | 180 |
| aagctcaacc cgggcgcgca cgagctgtcc ccgggccaga gctcggcgtt cacgtcgcag | 240 |
| ggccccggcg cctaccccgg ctccgctgcg gctgccgctg cggccgcagc gctcgggccc | 300 |
| cacgccgcgc acgttggctc ctactctggg ccgcccttca actccacccg ggacttcctg | 360 |
| ttccgcagcc gcggcttcgg ggactcggcg ccgggcggcg ggcagcacgg gctgttcggg | 420 |
| ccgggcgcgg gcggcctgca ccacgcgcac tcggacgcgc agggccacct cctcttcccg | 480 |
| ggcctgccag agcagcacgg gccgcacggc tcgcagaatg tgctcaacgg gcagatgcgc | 540 |
| ctcgggctgc ccggcgaggt gttcgggcgc tcggagcaat accgccaggt ggccagcccg | 600 |
| cggaccgacc cctactcggc ggcgcaactc cacaaccagt acggcccccat gaatatgaac | 660 |
| atgggtatga acatggcagc agccgcgcc caccaccacc accaccacca ccaccacccc | 720 |
| ggtgccttt ccgctatat gcggcagcag tgcatcaagc aggagctaat ctgcaagtgg | 780 |
| atcgaccccg agcaactgag caatcccaag aagagctgca caaaactttt cagcaccatg | 840 |
| cacgagctgg tgacacacgt ctcggtggag cacgtcggcg gcccggagca gagcaaccac | 900 |
| gtctgcttct gggaggagtg tccgcgcgag ggcaagccct tcaaggccaa atacaaactg | 960 |
| gtcaaccaca tccgcgtgca cacaggcgag aaacccttcc cctgccccctt ccgggctgt | 1020 |
| ggcaaagtct tcgcgcgctc cgagaacctc aagatccaca aaaggaccca cacaggggag | 1080 |
| aagccgttcc agtgtgagtt tgagggctgc gaccggcgct tcgccaacag cagcgacagg | 1140 |
| aagaagcaca tgcacgtcca cacctccgat aagcctatc tctgcaagat gtgcgacaag | 1200 |
| tcctacacgc accccagctc gctgcggaag cacatgaagg tccatgagtc ctccccgcag | 1260 |
| ggctctgaat cctccccggc cgccagctcc ggctatgagt cgtccacgcc ccgggggctg | 1320 |
| gtgtccccca gcgccgagcc ccagagcagc tccaacctgt ccccagcggc ggcggcagcg | 1380 |
| gcggcggcgg ctgcggcggc ggcggccgcg gtgtccgcgg tgcaccgggg cggaggctcg | 1440 |
| ggcagtggcg gcgcgggagg cggctcaggc ggcggcagcg gcagtggcgg gggcggcggc | 1500 |
| ggggcgggcg gcgggggcgg cggcagctct ggcggggca gcgggacagc cggggtcac | 1560 |
| agcggcctct cctccaactt caatgaatgg tacgtgtga | 1599 |

<210> SEQ ID NO 15
<211> LENGTH: 1404
<212> TYPE: DNA
<213> ORGANISM: Artificial Sequence
<220> FEATURE:
<223> OTHER INFORMATION: Synthesized ZIC3 gene

<400> SEQUENCE: 15

| | |
|---|---:|
| atgacgatgc tcctggacgg aggcccgcag ttccctgggc tgggagtggg cagcttcggc | 60 |
| gcgccgcgcc accacgagat gcccaaccgt gagccggcag gcatggggct gaatcccttc | 120 |
| ggggactcaa cccacgccgc cgccgccgcc ccgccgccgc ctgccttcaa gctgagcccct | 180 |
| gccgcggcgc acgatctatc ttcaggccag agctcggctt tcacgccgca gggttcgggc | 240 |
| tacgccaacg ccctgggcca ccatcaccac caccatcacc atcatcacca ccagccag | 300 |
| gtgcccagct acggtggcgc tgcctctgcc gccttcaact caacgcgcga gtttctgttc | 360 |
| cgccagcgca gctccgggct cagtgaggcg gcctcgggtg gcgggcagca cgggctcttc | 420 |
| gccggctcgg cgagcagcct gcatgctcca gctggcatcc ccgagccccc tagctacttg | 480 |
| ctgtttcccg ggctgcatga gcagggcgct gggcacccgt cgcccacagg gcacgtggac | 540 |

```
aacaaccagg tccacctggg gctgcgtggg gagctgttcg gccgtgctga cccataccgc    600
ccagtggcca gcccgcgcac ggaccectac gcggccggcg ctcagtttcc taactacagc    660
cccatgaaca tgaacatggg agtgaacgtg gcggcccacc acgggcccgg cgccttcttc    720
cgttatatgc ggcagcctat caagcaggag ctgtcgtgca agtggatcga cgaggctcag    780
ctgagccggc ccaagaagag ctgcgaccgg accttcagca ccatgcatga gctggtgaca    840
catgtcacca tggagcatgt ggggggcccg gagcagaaca ccacgtctg ctactgggag     900 gagtgccccc gggagggcaa gtcttcaag gcgaagtaca aactggtcaa ccacatccga     960
gtgcacacgg gcgagaagcc cttcccatgc cccttcccgg gctgcgggaa gatcttgcc    1020 cgttctgaga acctcaagat ccacaagagg acccacacag gtgagaaacc ttcaaatgt    1080 gaatttgaag gctgtgacag acgctttgcc aacagcagcg accgtaagaa gcacatgcat   1140
gtgcatacct cggacaagcc ctatatctgc aaagtgtgcg acaagtccta cacgcacccg   1200
agctccctgc gcaaacacat gaaggttcat gaatctcaag ggtcagattc ctcccctgct   1260
gccagttcag gctatgaatc ttccactcca cccgctatag cttctgcaaa cagtaaagat   1320
accactaaaa cccettctgc agttcaaact agcaccagcc acaaccctgg acttcctcct   1380
aattttaacg aatggtacgt ctga                                         1404

<210> SEQ ID NO 16
<211> LENGTH: 1335
<212> TYPE: DNA
<213> ORGANISM: Artificial Sequence
<220> FEATURE:
<223> OTHER INFORMATION: Synthesized GATA3 gene

<400> SEQUENCE: 16
atggaggtga cggcggacca gccgcgctgg gtgagccacc accaccccgc cgtgctcaac     60
gggcagcacc cggacacgca ccacccgggc ctcagccact cctacatgga cgcggcgcag    120
tacccgctgc cggaggaggt ggatgtgctt tttaacatcg acgtcaagg caaccacgtc     180 ccgcccctact acggaaactc ggtcagggcc acggtgcaga ggtaccctcc gacccaccac    240
gggagccagg tgtgccgccc gcctctgctt catggatccc tacctggct ggacggcggc     300 aaagccctgg gcagccacca caccgcctcc cctggaatc tcagcccctt ctccaagacg    360
tccatccacc acggctcccc ggggcccctc tccgtctacc cccgggctc gtcctcctcc    420 ttgtcggggg gccacgccag cccgcacctc ttccttcc cgcccacccc gccgaaggac     480
gtctccccgg acccatcgct gtccacccca ggctcggccg ctcggcccg gcaggacgag    540 aaagagtgcc tcaagtacca ggtgcccctg cccgacagca tgaagctgga gtcgtcccac    600
tcccgtggca gcatgaccgc cctgggtgga gcctcctcgt cgacccacca ccccatcacc    660
acctacccgc cctacgtgcc cgagtacagc tccggactct ccccccccag cagcctgctg    720
ggcggctccc ccaccggctt cggatgcaag tccaggccca aggccggtc cagcacagaa    780 ggcagggagt gtgtgaactg tgggcaacc tcgacccac tgtggcggcg agatggcacg    840
ggacactacc tgtgcaacgc ctgcgggctc tatcacaaaa tgaacggaca gaaccggccc   900
ctcattaagc ccaagcgaag gctgtctgca gccaggagag cagggacgtc ctgtgcgaac   960
tgtcagacca ccacaaccac actctggagg aggaatgcca atgggaccc tgtctgcaat   1020 gcctgtgggc tctactacaa gcttcacaat attaacagac cctgactat gaagaaggaa   1080 ggcatccaga ccagaaaccg aaaaatgtct agcaaatcca aaagtgcaa aaagtgcat    1140
```

```
gactcactgg aggacttccc caagaacagc tcgtttaacc cggccgccct ctccagacac    1200
atgtcctccc tgagccacat ctcgcccttc agccactcca gccacatgct gaccacgccc    1260
acgccgatgc acccgccatc cagcctgtcc tttggaccac caccccctc cagcatggtc     1320 accgccatgg gttag                                                     1335
```

<210> SEQ ID NO 17
<211> LENGTH: 1269
<212> TYPE: DNA
<213> ORGANISM: Artificial Sequence
<220> FEATURE:
<223> OTHER INFORMATION: Synthesized PAX6 gene

<400> SEQUENCE: 17

```
atgcagaaca gtcacagcgg agtgaatcag ctcggtggtg tctttgtcaa cgggcggcca      60
ctgccggact ccacccggca gaagattgta gagctagctc acagcggggc ccggccgtgc    120
gacatttccc gaattctgca ggtgtccaac ggatgtgtga gtaaaattct gggcaggtat    180
tacgagactg gctccatcag acccagggca atcggtggta gtaaaccgag agtagcgact    240
ccagaagttg taagcaaaat agcccagtat aagcgggagt gcccgtccat ctttgcttgg    300
gaaatccgag acagattact gtccgagggg gtctgtacca acgataacat accaagcgtg    360
tcatcaataa acagagttct tcgcaacctg gctagcgaaa agcaacagat gggcgcagac    420
ggcatgtatg ataaactaag gatgttgaac gggcagaccg aagctgggg cacccgccct     480 ggttggtatc cggggacttc ggtgccaggg caacctacgc aagatggctg ccagcaacag    540
gaaggagggg gagagaatac caactccatc agttccaacg agaagattc agatgaggct     600 caaatgcgac ttcagctgaa gcggaagctg caaagaaata aacatccctt tacccaagag    660
caaattgagg ccctggagaa agagtttgag agaacccatt atccagatgt gtttgcccga    720
gaaagactag cagccaaaat agatctacct gaagcaagaa tacaggtatg gttttctaat    780
cgaagggcca atggagaag agaagaaaaa ctgaggaatc agagaagaca ggccagcaac    840
acacctagtc atattcctat cagcagtagt ttcagcacca gtgtctacca accaattcca    900
caacccacca caccggtttc ctccttcaca tctggctcca tgttgggccg aacagacaca    960
gccctcacaa acacctacag cgctctgccg cctatgccca gcttcaccat ggcaaataac    1020
ctgcctatgc aaccccagt ccccagccag acctcctcat actcctgcat gctgcccacc     1080
agcccttcgg tgaatgggcg gagttatgat acctacaccc cccacatat gcagacacac     1140 atgaacagtc agccaatggg cacctcgggc accacttcaa caggactcat ttcccctggt    1200
gtgtcagttc cagttcaagt tcccggaagt gaacctgata tgtctcaata ctggccaaga    1260
ttacagtaa                                                            1269
```

<210> SEQ ID NO 18
<211> LENGTH: 3024
<212> TYPE: DNA
<213> ORGANISM: Artificial Sequence
<220> FEATURE:
<223> OTHER INFORMATION: Synthesized SALL2 gene

<400> SEQUENCE: 18

```
atgtctcggc gaaagcagcg gaaaccccaa cagttaatct cggactgcga aggtcccagc     60
gcgtctgaga acggtgatgc tagcgaggag gatcaccccc aagtctgtgc caagtgctgc    120
gcacaattca ctgacccaac tgaattcctc gcccaccaga acgcatgttc tactgaccct    180
cctgtaatgg tgataattgg gggccaggag aaccccaaca actcttcggc ctcctctgaa    240
```

```
ccccggcctg agggtcacaa taatcctcag gtcatggaca cagagcatag caaccccca      300
gattctgggt cctccgtgcc cacggatccc acctggggcc cagagaggag aggagaggag      360
tctccagggc atttcctggt cgctgccaca ggtacagcgg ctgggggagg cgggggcctg      420
atcttggcca gtcccaagct gggagcaacc ccattacctc cagaatcgac ccctgcaccc      480
cctcctcctc caccaccccc tccgccccca ggggtaggca gtggccactt gaatatcccc      540
ctgatcttgg aagagctacg ggtgctgcag cagcggcaga tccatcagat gcagatgact      600
gagcaaatct gcaggcaggt gctgttgctt ggctccttag ccagacggt gggtgcccct      660
gccagtccct cagagctacc tgggacaggg actgcctctt ccaccaagcc cctactaccc      720
ctcttcagcc ccatcaagcc tgtccaaacc agcaagacac tggcatcttc ctcctcctcc      780
tcctcttcct cttcagggc agaaacgccc aagcaggcct tcttccacct ttaccaccca      840
ctggggtcac agcatccttt ctctgctgga ggggttgggc gaagccacaa acccacccct      900
gcccttccc cagccttgcc aggcagcaca gatcagctga ttgcctcgcc tcatctggca      960
ttcccaagca ccacgggact actggcagca cagtgtcttg gggcagcccg aggccttgag     1020
gccactgcct ccccagggct cctgaagcca agaatggaa gtggtgagct gagctacgga     1080
gaagtgatgg gtcccttgga gaagcctggt ggaaggcaca atgccgctt ctgtgccaaa     1140
gtatttggca gtgacagtgc cctgcagatc caccttcgtt cccacacggg tgagaggccc     1200
tataagtgca atgtctgtgg aaaccgtttt accacccgtg gcaacctcaa agtgcatttc     1260
caccggcatc gtgagaagta cccacatgtg cagatgaacc cacacccagt accagagcac     1320
ctagactatg tcattaccag cagtggcttg ccttatggta tgtccgtgcc accagagaag     1380
gccgaggagg aggcagccac tccaggtgga ggggttgagc gcaagcctct ggtggcctcc     1440
acaacagcac tcagtgccac agagagcctg actctgctct ccaccagtgc aggcacagcc     1500
acggctccag gactcctgc tttcaataag tttgtgctca tgaaagcagt ggaacccaag     1560
aataaagctg atgaaaacac cccccaggg agtgagggct cagccatcag tggagtggca     1620
gaaagtagca cggcaactcg catgcaacta agtaagttgg tgacttcact accaagctgg     1680
gcactgctta ccaaccactt caagtccact ggcagcttcc ccttcccta tgtgctagag     1740
cccttggggg cctcaccctc tgagacatca aagctgcagc aactggtaga aaagattgac     1800
cggcaaggag ctgtggcggt gacctcagct gcctcaggag cccccaccac ctctgcccct     1860
gcaccttcat cctcagcctc ttctggacct aaccagtgtg tcatctgtct ccgagtgctt     1920
agctgtcctc gggccctacg ccttcattat ggccaacatg gaggtgagag gcccttcaaa     1980
tgcaaagtgt gtggcagagc cttctccacc aggggtaatc tgcgtgcaca tttcgtgggc     2040
cacaaggcca gtcagctgc ccgggcacag aattcctgcc ccatctgcca gaagaagttc     2100
accaatgctg tcactctgca gcagcatgtc cggatgcacc tgggggccca gatccccaac     2160
ggtggtactg cactccctga aggtggagga gctgctcagg agaatggctc cgagcaatct     2220
acagtctccg gggcagggag tttcccccag cagcagtccc agcagccatc accggaagag     2280
gagttgtctg aggaggagga agaggaggat gaggaagaag aggaagatgt gactgatgaa     2340
gattccctgg cagggagagg ctcagagagt ggaggtgaga aggcaatatc agtgagaggt     2400
gattcagaag aggcatctgg ggcagaggag gaggtgggga cagtggcggc agcagccaca     2460
gctgggaagg agatggacag taatgagaaa actactcaac agtcttcttt gccaccacca     2520
ccaccacctg acagcctgga tcagcctcag ccaatggagc agggaagcag tggtgtttta     2580
```

```
ggaggcaagg aagagggggg caaaccggag agaagctcaa gtccggcatc agcactcacc    2640
ccagaagggg aagccaccag cgtgaccttg gtagaggagc tgagcctgca ggaggcaatg    2700
agaaaggagc caggagagag cagcagcaga aaggcctgcg aagtgtgtgg ccaggccttt    2760
ccctcccagg cagctctgga ggagcatcag aagacccacc ccaaggaggg gccgctcttc    2820
acttgtgttt tctgcaggca gggctttctt gagcgggcta ccctcaagaa gcatatgctc    2880
ctggcacacc accaggtaca gccctttgcc ccccatggcc ctcagaatat tgctgctctt    2940
tctctagtcc ctggctgttc gccttccatc acctccacag ggctctcccc ctttccccga    3000
aaagatgacc ccacgatccc atga                                           3024
```

<210> SEQ ID NO 19
<211> LENGTH: 1221
<212> TYPE: DNA
<213> ORGANISM: Artificial Sequence
<220> FEATURE:
<223> OTHER INFORMATION: Synthesized LHX2 gene

<400> SEQUENCE: 19

```
atgctgttcc acagtctgtc gggccccgag gtgcacgggg tcatcgacga gatggaccgc      60
agggccaaga gcgaggctcc cgccatcagc tccgccatcg accgcggcga caccgagacg     120
accatgccgt ccatcagcag tgaccgcgcc gcgctgtgcg ccggctgcgg gggcaagatc     180
tcggaccgct actacctgct ggcggtggac aagcagtggc acatgcgctg cctcaagtgc     240
tgcgagtgca agctcaacct ggagtcggag ctcacctgtt tcagcaagga cggtagcatc     300
tactgcaagg aagactacta caggcgcttc tctgtgcagc gctgcgcccg ctgccacctg     360
ggcatctcgg cctcggagat ggtgatgcgc gctcgggact tggtttatca cctcaactgc     420
ttcacgtgca ccacgtgtaa caagatgctg accacgggcg accacttcgg catgaaggac     480
agcctggtct actgccgctt gcacttcgag gcgctgctgc agggcgagta ccccgcacac     540
ttcaaccatg ccgacgtggc agcggcggcc gctgcagccg cggcggccaa gagcgcgggg     600
ctgggcgcag caggggccaa ccctctgggt cttccctact acaatggcgt gggcactgtg     660 cagaagggc ggccgaggaa acgtaagagc ccgggccccg gtgcggatct gcggcctac      720 aacgctgcgc taagctgcaa cgaaaacgac gcagagcacc tggaccgtga ccagccatac     780
ccgagcagcc agaagaccaa gcgcatgcgc acgtccttca gcaccaccca gcttcggacc     840
atgaagtctt actttgccat taaccacaac cccgacgcca aggacttgaa gcagctcgcg     900
caaaagacgg gcctcaccaa gcgggtcctc caggtctggt tccagaacgc ccgagccaag     960
ttcaggcgca acctcttacg gcaggaaaac acgggcgtgg acaagtcgac agacgcggcg    1020
ctgcagacag ggacgccatc gggccccggcc tcggagctct ccaacgcctc gctcagcccc    1080
tccagcacgc ccaccaccct gacagacttg actagcccca cctgccaac tgtgacgtcc     1140 gtcttaactt ctgtgcctgg caacctggag ggccatgagc ctcacagccc ctcacaaacg    1200
actcttacca accttttcta a                                             1221
```

<210> SEQ ID NO 20
<211> LENGTH: 1236
<212> TYPE: DNA
<213> ORGANISM: Artificial Sequence
<220> FEATURE:
<223> OTHER INFORMATION: Synthesized MBD2 gene

<400> SEQUENCE: 20

```
atgcgcgcgc acccgggggg aggccgctgc tgcccggagc aggaggaggg ggagagtgcg      60
```

```
gcgggcggca gcggcgctgg cggcgactcc gccatagagc aggggggcca gggcagcgcg    120
ctcgccccgt ccccggtgag cggcgtgcgc agggaaggcg ctcggggcgg cggccgtggc    180
cgggggcggt ggaagcaggc gggccggggc ggcggcgtct gtggccgtgg ccggggccgg    240
ggccgtggcc ggggacgggg acggggccgg ggccggggcc gcggccgtcc cccgagtggc    300
ggcagcggcc ttggcggcga cggcggcggc tgcggcggcg gcggcagcgg tggcggcggc    360
gccccccggc gggagccggt ccctttcccg tcggggagcg cggggccggg gcccagggga    420
ccccgggcca cggagagcgg gaagaggatg gattgcccgg ccctcccccc cggatggaag    480
aaggaggaag tgatccgaaa atctgggcta agtgctggca agagcgatgt ctactacttc    540
agtccaagtg gtaagaagtt cagaagcaag cctcagttgg caaggtacct gggaaatact    600
gttgatctca gcagttttga cttcagaact ggaaagatga tgcctagtaa attacagaag    660
aacaaacaga gactgcgaaa cgatcctctc aatcaaaata agggtaaacc agacttgaat    720
acaacattgc caattagaca aacagcatca atttttcaaac aaccggtaac caaagtcaca    780
aatcatccta gtaataaagt gaaatcagac ccacaacgaa tgaatgaaca gccacgtcag    840
cttttctggg agaagaggct acaaggactt agtgcatcag atgtaacaga acaaattata    900
aaaaccatgg aactacccaa aggtcttcaa ggagttggtc caggtagcaa tgatgagacc    960
cttttatctg ctgttgccag tgctttgcac acaagctctg cgccaatcac agggcaagtc   1020
tccgctgctg tggaaaagaa ccctgctgtt tggcttaaca catctcaacc cctctgcaaa   1080
gcttttattg tcacagatga agacatcagg aaacaggaag agcgagtaca gcaagtacgc   1140
aagaaattgg aagaagcact gatggcagac atcttgtcgc gagctgctga tacagaagag   1200
atggatattg aaatggacag tggagatgaa gcctaa                             1236
```

<210> SEQ ID NO 21
<211> LENGTH: 2436
<212> TYPE: DNA
<213> ORGANISM: Artificial Sequence
<220> FEATURE:
<223> OTHER INFORMATION: Synthesized DEPDC1 gene

<400> SEQUENCE: 21

```
atggagagtc agggtgtgcc tcccgggcct tatcgggcca ccaagctgtg gaatgaagtt     60
accacatctt ttcgagcagg aatgcctcta gaaaaacaca gacaacactt taaaaaatat    120
ggcaattgtt tcacagcagg agaagcagtg gattggcttt atgaccatt aagaaataat     180 agcaattttg gtcctgaagt tacaaggcaa cagactatcc aactgttgag gaaatttctt    240
aagaatcatg taattgaaga tatcaaaggg aggtggggat cagaaaatgt tgatgataac    300
aaccagctct tcagatttcc tgcaacttcg ccacttaaaa ctctaccacg aaggtatcca    360
gaattgagaa aaacaacat agagaacttt tccaaagata agatagcat ttttaaatta     420 cgaaacttat ctcgtagaac tcctaaaagg catggattac atttatctca ggaaaatggc    480
gagaaaataa agcatgaaat aatcaatgaa gatcaagaaa atgcaattga taatagagaa    540
ctaagccagg aagatgttga agaagtttgg agatatgtta ttctgatcta cctgcaaacc    600 atttaggtg tgccatccct agaagaagtc ataaatccaa acaagtaat tcccaatat      660 ataatgtaca acatggccaa tacaagtaaa cgtggagtag ttatactaca aaacaaatca    720
gatgacctcc ctcactgggt attatctgcc atgaagtgcc tagcaaattg gccaagaagc    780
aatgatatga ataatccaac ttatgttgga tttgaacgag atgtattcag aacaatcgca    840
```

```
gattattttc tagatctccc tgaacctcta cttactttig aatattacga attatttgta    900
aacattttgg ttgtttgtgg ctacatcaca gtttcagata gatccagtgg gatacataaa    960
attcaagatg atccacagtc ttcaaaattc cttcacttaa acaatttgaa ttccttcaaa   1020
tcaactgagt gccttcttct cagtctgctt catagagaaa aaaacaaaga agaatcagat   1080
tctactgaga gactacagat aagcaatcca ggatttcaag aaagatgtgc taagaaaatg   1140
cagctagtta atttaagaaa cagaagagtg agtgctaatg acataatggg aggaagttgt   1200
cataatttaa tagggttaag taatatgcat gatctatcct ctaacagcaa accaaggtgc   1260
tgttctttgg aaggaattgt agatgtgcca gggaattcaa gtaaagaggc atccagtgtc   1320
tttcatcaat ctttttccgaa catagaagga caaaataata aactgttttt agagtctaag   1380
cccaaacagg aattcctgtt gaatcttcat tcagaggaaa atattcaaaa gccattcagt   1440
gctggtttta agagaacctc tactttgact gttcaagacc aagaggagtt gtgtaatggg   1500
aaatgcaagt caaaacagct tgtaggtct cagagtttgc ttttaagaag tagtacaaga   1560
aggaatagtt atatcaatac accagtggct gaaattatca tgaaaccaaa tgttggacaa   1620
ggcagcacaa gtgtgcaaac agctatggaa agtgaactcg gagagtctag tgccacaatc   1680
aataaaagac tctgcaaaag tacaatgaaa cttttcagaaa attctttact tccagcttct   1740
tctatgttga ctggcacaca aagcttgctg caacctcatt tagagagggt tgccatcgat   1800
gctctacagt tatgttgttt gttacttccc ccaccaaatc gtagaaagct tcaactttta   1860
atgcgtatga tttcccgaat gagtcaaaat gttgatatgc ccaaacttca tgatgcaatg   1920
ggtacgaggt cactgatgat acatacctt tctcgatgtg tgttatgctg tgctgaagaa   1980
gtggatcttg atgagcttct tgctggaaga ttagttctt tcttaatgga tcatcatcag   2040
gaaattcttc aagtaccctc ttacttacag actgcagtgg aaaaacatct tgactactta   2100
aaaaagggac atattgaaaa tcctggagat ggactatttg ctccttgcc aacttactca   2160
tactgtaagc agattagtgc tcaggagttt gatgagcaaa agtttctac ctctcaagct   2220
gcaattgcag aacttttaga aatattatt aaaaacagga gtttacctct aaaggagaaa   2280
agaaaaaaac taaacagtt tcagaaggaa tatcctttga tatatcagaa aagatttcca   2340
accacggaga gtgaagcagc acttttggt gacaaaccta caatcaagca accaatgctg   2400
attttaagaa aaccaaagtt ccgtagtcta agataa                             2436
```

<210> SEQ ID NO 22
<211> LENGTH: 1803
<212> TYPE: DNA
<213> ORGANISM: Artificial Sequence
<220> FEATURE:
<223> OTHER INFORMATION: Synthesized MYEF2 gene

<400> SEQUENCE: 22

```
atggcggacg ccaacaaggc cgaggtgccc ggggccactg gtggcgacag cccgcacctg     60
cagcccgcag agccgccggg cgagccgcgg cgagagccgc accccgcgga ggcggagaag    120
cagcagccgc agcacagcag cagctccaat ggcgttaaaa tggagaatga tgaatcagca    180
aaagaagaga atctgacttt aaaggaaaaa tctacaggaa gtaagaaggc caatagattt    240
catccttatt caaaagacaa gaattcgggc gctggagaaa agaagggtcc aaatcgtaac    300
agagttttca ttagcaacat cccatatgac atgaaatggc aagctattaa agatctaatg    360
agagagaaag ttggtgaggt tacatacgtg agctctttta aggatgcgga aggaaaatca    420
aggggttgtg gtgtggttga attcaaagat gaagaatttg taaagaaagc cctagaaact    480
```

```
atgaacaaat atgatcttag tggaagaccc cttaatatta aagaggatcc tgatggagaa    540
aatgctcgta gggcattgca gcgaacagga ggatcatttc caggaggaca cgtccctgat    600
atgggatcag ggttgatgaa tttaccacct tccatactca ataatccaaa cattcctcct    660
gaagtcatca gtaatttgca ggccggtaga cttggttcca caattttgt tgccaatctt     720 gacttcaaag ttggttggaa gaagctaaag gaagtgttca gcatagctgg aactgtgaag    780
cgggcagata ttaaagaaga caaagatggc aagagcagag gaatgggcac tgtcactttt    840
gagcaagcaa ttgaagcagt tcaagcaatt tctatgttca atgggcagtt tttatttgat    900
agacctatgc atgtgaaaat ggatgacaag tctgttcctc atgaagagta ccgttcacat    960
gatggtaaaa caccacaatt accacgtggt cttggaggca ttgggatggg acttggtccg   1020
ggtggacagc ctattagtgc cagccagttg aacataggtg gagtaatggg aaatttaggt   1080
ccaggtggta tgggaatgga tggtccaggt tttggaggaa tgaatagaat tggaggagga   1140
ataggttttg gtggtctgga agcaatgaat agcatgggag gatttggagg agttggccga   1200
atgggagagc tgtaccgtgg tgcgatgact agtagcatgg agcgagattt tggacgtggt   1260
gatattggaa taaatcaagg ctttggagat tcctttggta gacttggcag tgcaatgatt   1320
ggagggtttg caggaagaat aggatcttct aacatgggtc cagtaggatc tggaataagt   1380 ggtgaatgg gtagcatgaa cagtgtgact ggaggaatgg ggatgggact ggaccggatg    1440
agttccagct ttgatagaat gggaccaggt ataggagcta tactggaaag gagcatcgat   1500
atggatcgag gatttttatc gggtccaatg ggaagcggaa tgagagagag aataggctcc   1560
aaaggcaacc agatatttgt cagaaatcta cctttgact tgacttggca gaaactaaaa    1620
gagaaattca gtcagtgtgg tcatgtaatg ttgcagaaa taaaatgga gaatggaaag     1680 tcaaaggct gtgaacagt cagatttgac tccccagaat cagctgaaaa agcctgcaga    1740
ataatgaatg gcataaaaat cagtggcaga gaaattgatg ttcgcttgga tcgtaatgca  1800
taa                                                                1803
```

<210> SEQ ID NO 23
<211> LENGTH: 870
<212> TYPE: DNA
<213> ORGANISM: Artificial Sequence
<220> FEATURE:
<223> OTHER INFORMATION: Synthesized OTX2a gene

<400> SEQUENCE: 23

```
atgatgtctt atcttaagca accgccttac gcagtcaatg ggctgagtct gaccacttcg     60
ggtatggact tgctgcaccc ctccgtgggc tacccggcca ccccccggaa cagcgccgg    120 gagaggacga cgttcactcg ggcgcagcta gatgtgctgg aagcactgtt tgccaagacc    180
cggtacccag acatcttcat gcgagaggag gtggcactga aaatcaactt gcccgagtcg    240
agggtgcagg tatggtttaa gaatcgaaga gctaagtgcc gccaacaaca gcaacaacag    300
cagaatggag gtcaaaacaa agtgagacct gccaaaaaga agacatctcc agctcgggaa    360
gtgagttcag agagtggaac aagtggccaa ttcactcccc cctctagcac ctcagtcccg    420
accattgcca gcagcagtgc tcctgtgtct atctggagcc cagcttccat ctccccactg    480
tcagatccct tgtccacctc ctcttcctgc atgcagaggt cctatcccat gacctatact    540
caggcttcag gttatagtca aggatatgct ggctcaactt cctactttgg gggcatggac    600
tgtggatcat atttgacccc tatgcatcac cagcttcccg gaccagggc cacactcagt    660
```

```
cccatgggta ccaatgcagt caccagccat ctcaatcagt ccccagcttc tctttccacc      720
cagggatatg agcttcaag cttgggtttt aactcaacca ctgattgctt ggattataag       780
gaccaaactg cctcctggaa gcttaacttc aatgctgact gcttggatta taaagatcag     840
acatcctcgt ggaaattcca ggttttgtga                                     870
```

<210> SEQ ID NO 24
<211> LENGTH: 999
<212> TYPE: DNA
<213> ORGANISM: Artificial Sequence
<220> FEATURE:
<223> OTHER INFORMATION: Synthesized SIX3 gene

<400> SEQUENCE: 24

```
atggtattcc gctccccct agacctctat tcctcccact tcttgttgcc aaacttcgcc       60
gattctcacc accgctccat acttctggcg agtagcggcg cgggaacgg tgcgggaggc      120 ggcggcggcg cgggaggcgg cagcggcggc gggaacggtg cgggaggcgg cggtgctggc    180
ggagcaggcg gcggcggcgg cggcggctcc agggcccccc cggaagagtt gtccatgttc    240
cagctgccca ccctcaactt ctcgccggag caggtggcca gcgtctgtga cgctggag      300 gagacgggcg acatcgagcg gctgggccgc ttcctctggt cgctgcccgt ggccccggg    360 gcgtgcgagg ccatcaacaa acacgagtcg atcctgcgcg cgcgcgccgt ggtcgccttc   420
cacacgggca acttccgcga cctctaccac atccttgaga ccacaagtt caccaaggag    480 tctcacggca agctgcaggc catgtggctc gaggcgcact accaggaggc cgagaagctg    540
cgcggccgcc cactcggccc ggtggacaag taccgcgtgc gcaagaagtt cccgctgcca   600
cgcaccatct gggacggcga gcagaagacg cattgcttca aggagcggac tcggagcctg   660
ttgcgggagt ggtacctaca ggaccccta cccaaccca gcaagaaacg cgaactggcg    720
caggccaccg gcctcactcc cacacaagta ggcaactggt ttaagaaccg gcggcagcgc    780
gaccgcgccg cggcggccaa gaacaggctc cagcaccagg ccattggacc gagcggcatg   840
cgctcgctgg ccgagcccgg ctgccccacg cacggctcgg cagagtcgcc gtccacggcg    900
gccagcccga ccaccagcgt gtccagcctg acggagcgcg cagacaccgg cacctccatc    960
ctctcggtaa cctccagcga ctcggaatgt gatgtatga                          999
```

<210> SEQ ID NO 25
<211> LENGTH: 1176
<212> TYPE: DNA
<213> ORGANISM: Artificial Sequence
<220> FEATURE:
<223> OTHER INFORMATION: Synthesized SOX1 gene

<400> SEQUENCE: 25

```
atgtacagca tgatgatgga gaccgacctg cactcgcccg gcggcgccca ggcccccacg      60
aacctctcgg ccccgccggg ggcgggcggc ggcggggggcg gaggcggggg cggcggcggc    120 ggcggggggcg ccaaggccaa ccaggaccgg gtcaaacggc ccatgaacgc cttcatggtg   180
tggtcccgcg gcagcggcg caagatggcc caggagaacc ccaagatgca caactcggag    240
atcagcaagc gctgggggc cgagtggaag gtcatgtccg aggccgagaa gcggccgttc    300
atcgacgagg ccaagcggct gcgcgcgctg cacatgaagg agcacccgga ttacaagtac    360
cggccgcgcc gcaagaccaa gacgctgctc aagaaggaca gtactcgct ggccggcggg    420 ctcctgcgcg ccggcgcggg tggcggcggc ggctgtgg ccatgggcgt gggcgtgggc    480
gtgggcgcgg cggccgtggg ccagcgcctg gagagcccag gcgcgcggc gggcggcggc   540
```

```
tacgcgcacg tcaacggctg ggccaacggc gcctacccg gctcggtggc ggcggcggcg      600
gcggccgcgg ccatgatgca ggaggcgcag ctggcctacg gcagcaccc gggcgcgggc      660 ggcgcgcacc cgcacgcgca ccccgcgcac ccgcacccgc accaccccgca cgcgcacccg     720 cacaacccgc agcccatgca ccgctacgac atgggcgcg tgcagtacag ccccatctcc      780
aactcgcagg gctacatgag cgcgtcgccc tcgggctacg gcggcctccc ctacggcgcc     840
gcggccgccg ccgccgccgc tgcgggcggc gcgcaccaga actcggccgt ggcggcggcg     900
gcggcggcgg cggccgcgtc gtcgggcgcc ctgggcgcgc tgggctctct ggtgaagtcg     960
gagcccagcg gcagcccgcc cgccccagcg cactcgcggg cgccgtgccc cggggacctg     1020
cgcgagatga tcagcatgta cttgcccgcc ggcgaggggg cgacccggc ggcggcagca      1080 gcggccgcgc gcagagccg gctgcactcg ctgccgcagc actaccaggg gcgggcgcg      1140 ggcgtgaacg gcacggtgcc cctgacgcac atctag                               1176
```

<210> SEQ ID NO 26
<211> LENGTH: 2004
<212> TYPE: DNA
<213> ORGANISM: Artificial Sequence
<220> FEATURE:
<223> OTHER INFORMATION: Synthesized PAX6:EGFP gene

<400> SEQUENCE: 26

```
tgaggtgtgt cctaatcgtg cggcattcaa caaatggact tctggtgtgt ggtcagaaga      60
gaaaagccat ttacttactt tcctccccgg ttttctggca acagctgaag gggagctgcc     120
tccgtggact gagcagaccc aggagaggga gtcgtggtgc ggagacacac gcaccacaca     180
cagatgaccg gtggcacaca cgacacacgc tgacataccg acatcgccag tgggacacac     240
acacacacac acacacacac acacacacac acagagagag agagaatccc tcccagcatt     300
ggtcatccgc cccccaccc aggcttccac tcccccctccc ctcttatctc ccctggcttc      360
ccctcctctc gggcgctgcg aaaagcagcc gcacttagtc aacaaatggc acgtgggaga     420
agttggtgag tgtttggtga ggactcttca gggcttttca caagaaccct ctgtacacaa     480
agtaagtggc gtgtttactc gggcctctcc agccagagct gtgcctctgc tccgctgcgc     540
accgcggctt ccgaaaggag aaaggagaga agaaagggcg gggagagcgg ggtggaggat     600
ttggacaggc cctggaggct tgggctgggg aggcctctgg cctcgtttag ttctcggccc     660
ggcaacctcc tctcggccta ggcttcgccg cggcctccgc agctggaatg gagctgccag     720
gacccagtga cgctcccgcc cctttcctct tcttccaagg ggccaggtgg gctggggtgc     780
ggccgccgct gtgctctgtg tcttggggcc ccggctggga tggggtgggg gcgggcgggg    840 gcggggcgg aggccacgct gtcctggagt tggcaagaaa ggacagcaca gaaacttgca     900
ccctccgagg actgggagtc ccgagtccag cttaggggga gtggggcgc gacccccaac     960 ccagaaacct tcacttgacc gctcaagttc gcggcagcag ggcgggccgc gccgaatctc     1020
ggcgtgcgcg gagcggggag atgcaggcga cgcccagagc ccgggctcgg gggccctgcg     1080
ccggggagag gagccgggac ccaccggcgg agccgaaaac aagtgtattc atattcaaac     1140
aaacggacca attgcaccag gcggggagag ggagcatcca atcggctggc gcgaggcccc     1200
ggcgctgctt tgcataaagc aatatttttgt gtgagagcga gcggtgcatt tgaagcttag     1260
atctggatcc cctctagagt cgagatggtg agcaagggcg aggagctgtt caccggggtg     1320
gtgcccatcc tggtcgagct ggacggcgac gtaaacggcc acaagttcag cgtgtccggc     1380
```

```
gagggcgagg gcgatgccac ctacggcaag ctgaccctga agttcatctg caccaccggc    1440
aagctgcccg tgccctggcc caccctcgtg accaccctga cctacggcgt gcagtgcttc    1500
agccgctacc ccgaccacat gaagcagcac gacttcttca gtccgccat gcccgaaggc     1560 tacgtccagg agcgcaccat cttcttcaag gacgacggca actacaagac ccgcgccgag    1620
gtgaagttcg agggcgacac cctggtgaac cgcatcgagc tgaagggcat cgacttcaag    1680
gaggacggca acatcctggg gcacaagctg gagtacaact acaacagcca caacgtctat    1740
atcatggccg acaagcagaa gaacggcatc aaggtgaact tcaagatccg ccacaacatc    1800
gaggacggca gcgtgcagct cgccgaccac taccagcaga cacccccat cggcgacggc     1860 cccgtgctgc tgcccgacaa ccactacctg agcacccagt ccgccctgag caaagacccc    1920
aacgagaagc gcgatcacat ggtcctgctg gagttcgtga ccgccgccgg gatcactctc    1980
ggcatggacg agctgtacaa gtaa                                           2004

<210> SEQ ID NO 27
<211> LENGTH: 1810
<212> TYPE: DNA
<213> ORGANISM: Artificial Sequence
<220> FEATURE:
<223> OTHER INFORMATION: Synthesized SOX1:EGFP gene

<400> SEQUENCE: 27
caacccaatc gttaatcatt cggaacgcgc gggcggggag cggcgaggag ggcgagctcg      60
gggttcgccg ccgccgccgc cgccgcgcgc gcgcgctcag gaagcggtgt ggctgtcacc    120
ccctcccggg cctcctcccc cctccttcct gctttgctcc ccctccttcc tcccctcctc    180
cccgctccgc cgcccgcgcc cagtgtatct actccctccc cacgtcactc gccagcgcgc    240
catgcaaatc accgccgccg ccggctccca ttggccgcgg cgcgctcatt taatggcagc    300
ccgggcccgg cgtatggctg ctgggccccg cgcgccgccg ccccgcgtg cgcctccgct     360 ccgagcgcac ggccccgggc aggcagcggg cagcccatcc cgggctcggc ggccccggct    420
ctccggccct ctccgcgagc ccgcgctcct cccgctgtcc ccgggcccct cctggctgc     480 accgtaatcg ccccctgcag gccccccctgc gcctccccccc cccgccact ggcgcctggc    540 ttcccccggg cacctgggac cagcacatgc ccagcgcacg cggcgcgccg ccctgctaga    600
agttgcagcc tccgagttgg aggccgctga ggaccgagcg caggaggaag gagacagcgc    660
gcagcggcgg ccggcgagga gacagcacac cccgggccgg gccagcgca ccgctcccgg     720 ccccaaaagc ggagctgcaa cttggccacg actgcacctg tttgcaccgc tccgccgagg    780
gcgcctgggc tgcggtggcg gcgaagacgg cgaccccgac cgtcggcctc tttggcaagt    840
ggtttgtgca tcaggagaaa cttttccacct cgagccgaa ccggcgccga gtgcgtgtgt     900
ttctgccttt ttttgttgtc gttgcctcca cccctcccca ttcttctctc cgctaggacc    960
cccccgcccc cgtctcactc cgtctgaatt cctctccgtc tccctcccac cccggccgtc    1020
tatgctccag gccctctcct cgcggtgccg gtgaacccgc cagccgcccc gggatccacc    1080
ggtcgccacc atggtgagca agggcgagga gctgttcacc ggggtggtgc ccatcctggt    1140
cgagctggac ggcgacgtaa acggccacaa gttcagcgtg tccggcgagg gcgagggcga    1200
tgccacctac ggcaagctga ccctgaagtt catctgcacc accggcaagc tgcccgtgcc    1260
ctggcccacc ctcgtgacca ccctgaccta cggcgtgcag tgcttcagcc gctacccga     1320 ccacatgaag cagcacgact tcttcaagtc cgccatgccc gaaggctacg tccaggagcg    1380
caccatcttc ttcaaggacg acggcaacta caagacccgc gccgaggtga agttcgaggg    1440
```

```
cgacaccctg gtgaaccgca tcgagctgaa gggcatcgac ttcaaggagg acggcaacat    1500
cctggggcac aagctggagt acaactacaa cagccacaag gtctatatca tggccgacaa    1560
gcagaagaac ggcatcaagg tgaacttcaa gatccgccac aacatcgagg acggcagcgt    1620
gcagctcgcc gaccactacc agcagaacac ccccatcggc gacggccccg tgctgctgcc    1680
cgacaaccac tacctgagca cccagtccgc cctgagcaaa gaccccaacg agaagcgcga    1740
tcacatggtc ctgctggagt tcgtgaccgc cgccgggatc actctcggca tggacgagct    1800
gtacaagtaa                                                          1810
```

KIT AND METHOD FOR PRODUCING INDUCED EMBRYONIC NEURAL PROGENITORS

CROSS-REFERENCE TO RELATED APPLICATIONS

This application relates to and claims the benefit of U.S. Provisional Application No. 62/484,409, filed Apr. 12, 2017; the content of the application is incorporated herein by reference in its entirety.

BACKGROUND OF THE INVENTION

1. Field of the Invention

The present disclosure in general relates to the treatment of neurological diseases. More particularly, the present disclosure relates to kits comprising specified differentiation factors, and their uses as a platform for selecting a drug candidate to treat neurological diseases.

2. Description of Related Art

Certain progressive, degenerative, and ultimately fatal, neurological diseases, like Huntington's Disease (HD) and Alzheimer's disease (AD), cannot be effectively treated; as such, there remains a need to elucidate the pathological progress behind these disorders, and further effective clinical interventions. By taking advantage of pluripotency reprogramming technology, researchers can readily reprogram disease-specific induced pluripotent stem cells (iPSCs) from patients' somatic cells, and subject them to in vitro differentiation for generation of various disease-relevant cell types for disease modeling and drug development. However, tumorigenic and spontaneous differentiation of iPSCs remains a concern. In addition to iPSCs, induced neurons (iNs), which can be directly converted from fibroblasts (FBs) by defined transcription factors (TFs), provide another source of neuronal cells for in vitro disease modeling and drug testing. The advantages of iN technology are that it can provide a fast and simple method for the generation of specific neuronal subtypes, and its use may avoid certain problems, such as uncontrolled cell differentiation and tumor formation, which are associated with hiPSCs. However, the induction of each neuronal subtype requires different combination of defined factors and the yield of such iNs is still too low for meaningful clinical applications. Therefore, developing strategies that allow direct conversion of somatic cells into expandable neural stem cell/progenitor (NSC/NP) populations which possess multiple neural differentiation potentials is an important step towards the generation of patient-specific neural cell types on a scalable level.

Previously, it was demonstrated that induced NP (iNPs) can be directly converted from mouse somatic cells by overexpressing various TF combinations. According to previous report, expandable iNPs could be generated from FBs via a modified pluripotency reprogramming procedure, and the resulting iNPs were able to differentiate into neurons and glial cells. Subsequently, several studies reported the generation of iNPs through the introduction of neural-enriched factors with/without iPSC factors, and the resulting iNPs were able to differentiate into all three major neural cell types of central nervous system (CNS). Meanwhile, reports show that human iNPs can also be converted from somatic cells via the introduction of TFs. In these studies, several TF combinations, including at least one of the iPS factors, were used for hiNP generation, and the differentiation propensity of the iNPs described in the aforementioned studies was mainly restricted to CNS neurons.

Human embryonic stem cells (hESCs) can be used as an in vitro differentiation model to generate neural phenotypes of various developmental stages, including embryonic NPs (ENPs) populations, and the critical neural genetic factors that contribute to the neural fate acquisition have begun to be uncovered. Given that hESC-ENP populations possess broad differentiation potential to give rise to both CNS and peripheral nervous system (PNS) neural cell types, it may be possible to directly convert FBs into iNPs resembling hESC-ENPs through the use of TFs highly expressed in hESC-ENP population.

Here, we identified a panel of neural TFs (nTFs) highly enriched in hESC-ENPs as compared to FBs, through comparative gene expression profiling. We defined two TF combinations, the overexpression of which can efficiently convert human FBs into multipotent iENPs. The iENP populations generated in this manner resemble hESC-ENPs in many respects, including their pattern of proliferation, gene expression profile, and in vitro and in vivo differentiation propensity. Importantly, we found that different combinations of TFs can induce iENP populations with varying proliferative features and regional differentiation preferences. We also demonstrated that neurons derived from AD- and HD-iENP, recapitulated the major disease pathological features in vitro. Taken together, our results point toward a promising and reproducible strategy for generating iENPs from somatic cells for disease modeling and future clinical intervention.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a first kit useful in selecting a drug candidate in the purpose of treating a neurological disease. According to embodiments of the present disclosure, the first kit comprises six polynucleotides respectively comprising the genes of CBX2 (SEQ ID NO: 1), HES1 (SEQ ID NO: 2), ID1 (SEQ ID NO: 3), TFAP2A (SEQ ID NO: 4), ZFP42 (SEQ ID NO: 5) and ZNF423 (SEQ ID NO: 6).

According to optional embodiments of the present disclosure, in addition to the six polynucleotides, the first kit further comprises additional polynucleotides. In one embodiment, the first kit further comprises nine polynucleotides respectively comprising the genes of DACH1 (SEQ ID NO: 7), FOXG1 (SEQ ID NO: 8), MYCN (SEQ ID NO: 9), NR2F2 (SEQ ID NO: 10), NR6A1 (SEQ ID NO: 11), SOX2 (SEQ ID NO: 12), SOX11 (SEQ ID NO: 13), ZIC2 (SEQ ID NO: 14) and ZIC3 (SEQ ID NO: 15). In another embodiment, the first kit further comprises nineteen polynucleotides respectively comprising the genes of DACH1 (SEQ ID NO: 7), FOXG1 (SEQ ID NO: 8), MYCN (SEQ ID NO: 9), NR2F2 (SEQ ID NO: 10), NR6A1 (SEQ ID NO: 11), SOX2 (SEQ ID NO: 12), SOX11 (SEQ ID NO: 13), ZIC2 (SEQ ID NO: 14), ZIC3 (SEQ ID NO: 15), GATA3

(SEQ ID NO: 16), PAX6 (SEQ ID NO: 17), SALL2 (SEQ ID NO: 18), LHX2 (SEQ ID NO: 19), MBD2 (SEQ ID NO: 20), DEPDC1 (SEQ ID NO: 21), MYEF2 (SEQ ID NO: 22), OTX2a (SEQ ID NO: 23), SIX3 (SEQ ID NO: 24) and SOX1 (SEQ ID NO: 25).

Optionally, the first kit may further comprise a reporter polynucleotide, which comprises the sequence of SEQ ID NO: 26.

The second aspect of the present disclosure is directed to a second kit useful in selecting a drug candidate in the purpose of treating a neurological disease. According to embodiments of the present disclosure, the second kit comprises seven polynucleotides respectively comprising the genes of TFAP2A (SEQ ID NO: 4), ZFP42 (SEQ ID NO: 5), FOXG1 (SEQ ID NO: 8), NR2F2 (SEQ ID NO: 10), GATA3 (SEQ ID NO: 16), PAX6 (SEQ ID NO: 17) and SALL2 (SEQ ID NO: 18).

In addition to the seven polynucleotides, the second kit may further comprise additional polynucleotides. In one embodiment, the second kit further comprises six polynucleotides respectively comprising the genes of CBX2 (SEQ ID NO: 1), HES1 (SEQ ID NO: 2), NR6A1 (SEQ ID NO: 11), SOX11 (SEQ ID NO: 13), ZIC2 (SEQ ID NO: 14) and LHX2 (SEQ ID NO: 19). In another embodiment, the second kit further comprises eighteen polynucleotides, including CBX2 (SEQ ID NO: 1), HES1 (SEQ ID NO: 2), ID1 (SEQ ID NO: 3), ZNF423 (SEQ ID NO: 6), DACH1 (SEQ ID NO: 7), MYCN (SEQ ID NO: 9), NR6A1 (SEQ ID NO: 11), SOX2 (SEQ ID NO: 12), SOX11 (SEQ ID NO: 13), ZIC2 (SEQ ID NO: 14), ZIC3 (SEQ ID NO: 15), LHX2 (SEQ ID NO: 19), MBD2 (SEQ ID NO: 20), DEPDC1 (SEQ ID NO: 21), MYEF2 (SEQ ID NO: 22), OTX2a (SEQ ID NO: 23), SIX3 (SEQ ID NO: 24) and SOX/(SEQ ID NO: 25).

Optionally, the second kit may further comprise a reporter polynucleotide, which comprises the sequence of SEQ ID NO: 27.

According to one embodiment of the present disclosure, the first or the second kit further comprises an enhancer selected from the group consisting of, RepSox, PP242, DZNep, vitamin C and a combination thereof.

The third aspect of the present disclosure pertains to a method of selecting a drug candidate suitable for treating a neurological disease (e.g., a neurodevelopment disease, a neurodegenerative disease or a motor neuron disease). According to embodiments of the present disclosure, the method comprises the steps of, (a) introducing the polynucleotides of the first or second kit into a fibroblast cell thereby inducing the fibroblast cell into an induced embryonic neural progenitor (iENP) cell;

(b) incubating the iENP cell of step (a) in a differentiation medium thereby inducing the iENP cell into an astrocyte, an oligodendrocyte or a neuron;

(c) exposing the astrocyte, the oligodendrocyte or the neuron of step (b) to one or more candidate drugs; and (d) selecting the drug candidate from the one or more candidate drugs, wherein the drug candidate changes the phenotype or the gene expression of the astrocyte, the oligodendrocyte or the neuron.

Basically, the fibroblast cell can be derived from a healthy subject or a subject having the neurological disease. According to one preferred example, the fibroblast cell is derived from a subject having a neurodegenerative disease.

Another aspect of the present disclosure is directed to a method of treating a subject having or suspected of having a neurological disease. The method comprises the steps of, (a) isolating a fibroblast cell from the subject;

(b) introducing the polynucleotides of the first or second kit into the fibroblast cell thereby inducing the fibroblast cell into an iENP cell;

(c) optionally, incubating the iENP cell of step (b) in a differentiation medium thereby inducing the iENP cell into an astrocyte, an oligodendrocyte or a neuron; and (d) administering to the subject an effective amount of the iENP cell of step (b), or an effective amount of the astrocyte, the oligodendrocyte or the neuron of step (c) so as to alleviate or ameliorate the symptoms associated with the neurological disease.

In general, the neurological disease may be a neurodevelopment disease, a neurodegenerative disease or a motor neuron disease.

Also disclosed are the cells induced by the present kit, including an iENP cell, an astrocyte, an oligodendrocyte and a neuron. The induced cell may be applied to treat a neurological disease; for example, a neurodevelopment disease, a neurodegenerative disease or a motor neuron disease.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where:

(FIG. 1A) Identification of hESC-ENP-enriched neural TFs by comparative gene expression profiling of FBs and hESC-ENPs. (Panel a) Heatmap analysis of the global gene expression profiles of hESC-ENPs [NP1 (E-MEXP-2668, ArrayExpress database); NP2 from H9-SOX1:EGFP sorted ND day 18-NP] and FBs (FB1, -2, and -3)]. (Panel b) Selected TFs with higher expression in hESC-ENPs than in FBs. (FIG. 1B) Infection of FBs with lentivirus encoding hESC-ENP TFs (25TF) and neural reporter, and the growth of FACS-sorted cells. Cells infected with UbC:EGFP were used as controls. (FIG. 1C) ICC analysis of iENP-25F clusters resembling NP colonies/spheres using antibodies against the indicated antigen. (FIG. 1D) RT-PCR analysis of the indicated genes in iENP-25F. FB, fibroblast; NC, negative control ($H_2O$).

(FIGS. 2A and 2B) Step-wise selection of potent iENP factors for iENP-6F generation by single TF dropouts from the original 25-TF set (FIG. 2A) and the 15-TF set (FIG. 2B). The results are expressed as the relative percentage of PAX6:EGFP$^+$ cells after each TF was removed from the 25-TF or 15-TF combinations. (FIG. 2C) Comparison of the efficiency of induction of PAX6:EGFP$^+$ cells from FBs by 25-, 15-, and 6-TF combinations. (FIG. 2D) Global gene expression heatmap of FB, hESC-ENP, iENP-6F, and iENP-15F as determined by microarray analysis. (FIG. 2E) ICC staining of iENPs-6F using antibodies against the indicated NP markers. (FIG. 2F) RT-PCR analysis of endogenous and exogenous expression of the 6 TFs using mRNA isolated from iENP-6F. (FIG. 2G) RT-PCR analysis of the indicated neural genes using mRNA isolated from iENP-6F. FB, fibroblast;

NC, negative control (H$_2$O); plasmid, expression plasmids for the indicated genes. All quantitative data were obtained from three independent experiments and are presented as means±SD. See also FIGS. 8-10.

Figure 3A:
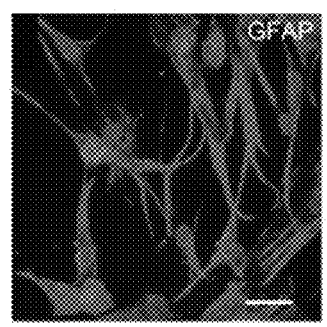
Figure 3B:
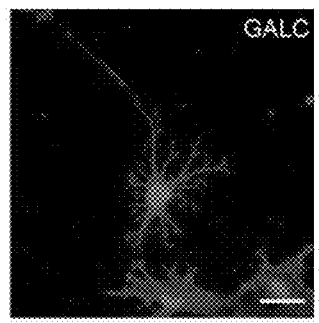
Figure 3C:
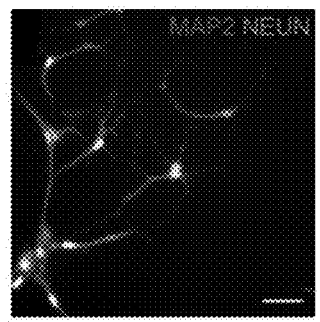
Figure 3D:
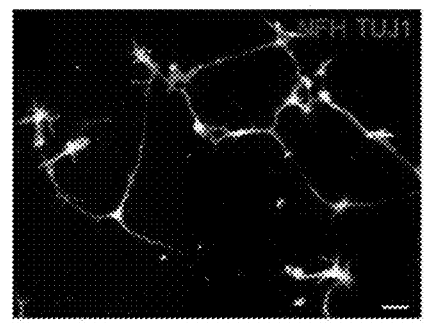
Figure 3E:
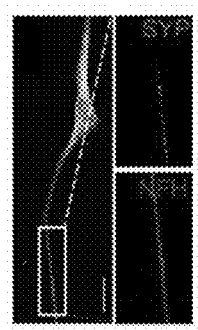
Figure 3F:
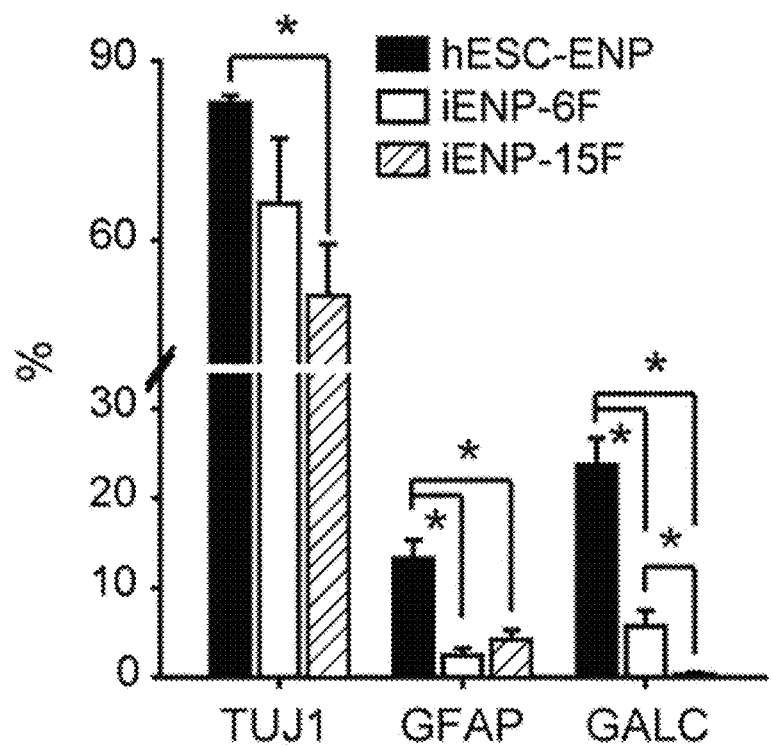
Figure 3G:
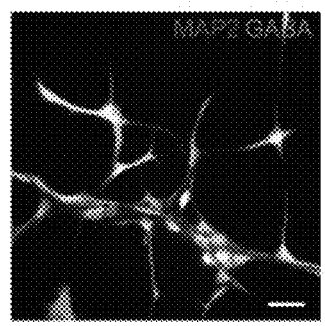
Figure 3H:
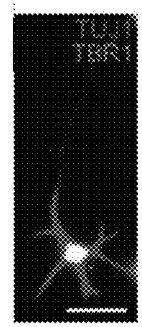
Figure 3I:
Figure 3J:
Figure 3K:
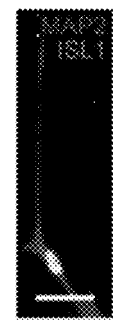
Figure 3L:
Figure 3M:
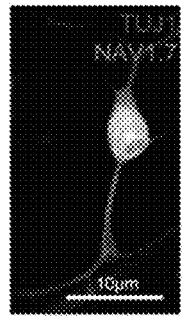
Figure 3N:
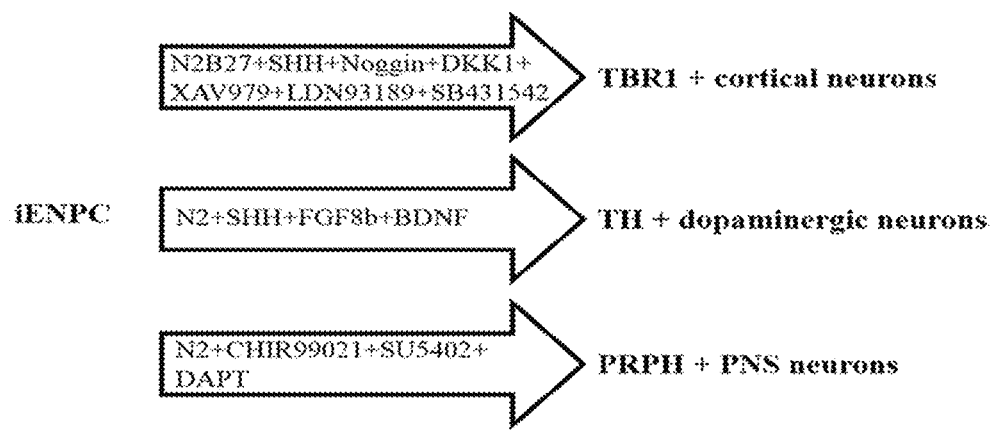
Figure 3N:
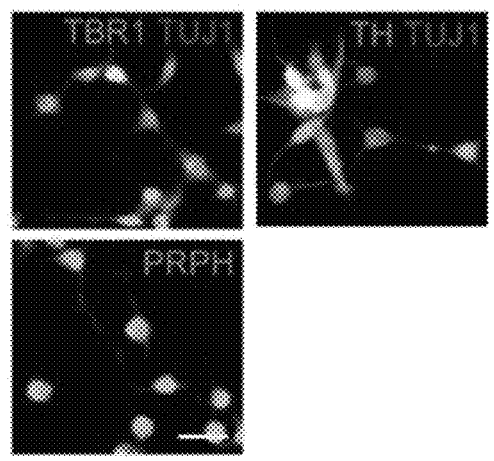
Figure 3N:
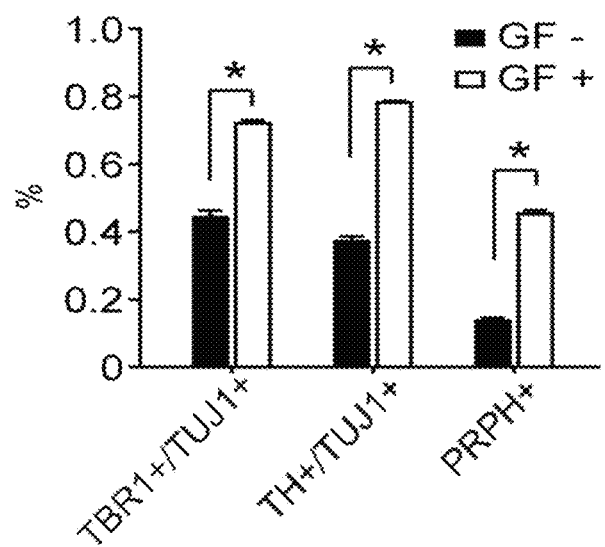
Figure 3O:
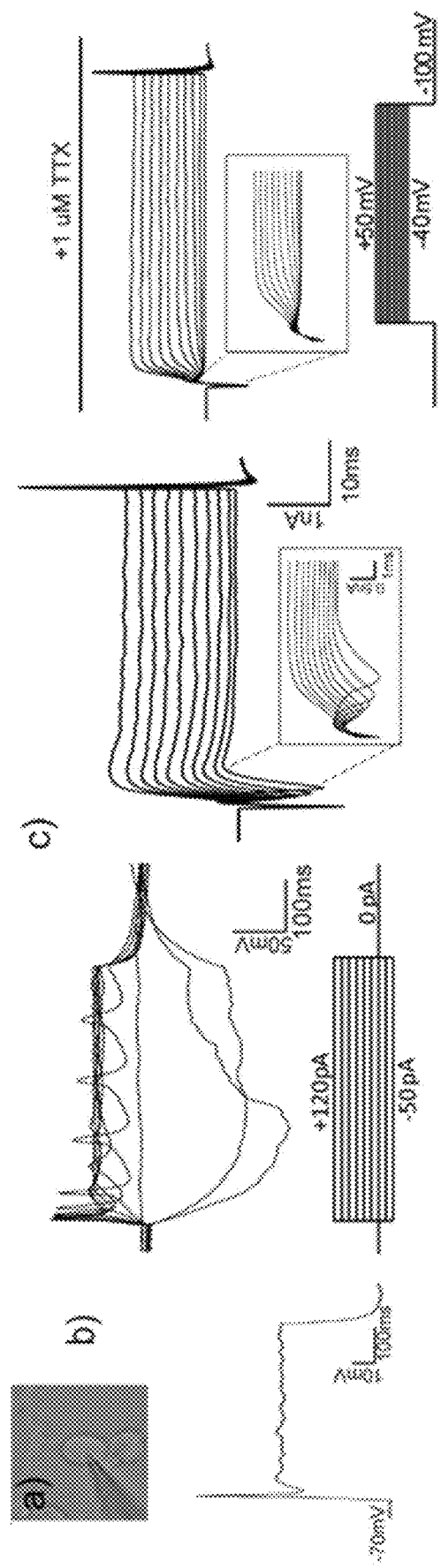
Figure 3P:
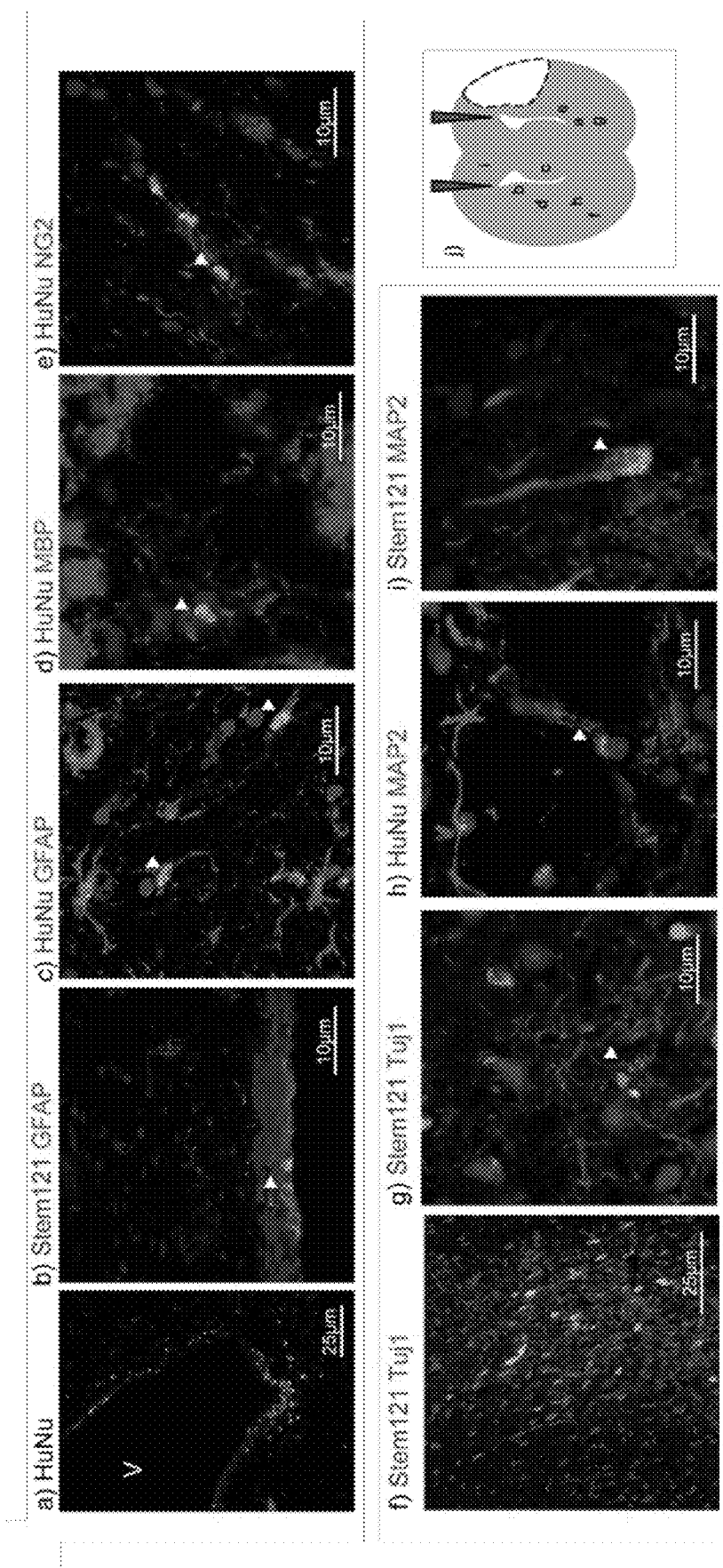

FIGS. 3A-3P. Multipotency of iENP-6F in vitro and in vivo. (FIGS. 3A-3E) ICC staining of differentiated iENP-6F using antibodies against the glial marker GFAP (FIG. 3A), oligodendrocyte marker GALC (FIG. 3B), and neuronal markers, as indicated (FIGS. 3C and 3D), and synapse marker SYN (FIG. 3E). (FIG. 3F) Quantification and comparison of TUJ1$^+$, GFAP$^+$, and GALC$^+$ cells in differentiated hESC-NPs, iENP-6F, and iENP-15F. (FIGS. 3G-3M) ICC staining of differentiated iENP-6F using antibodies against CNS and PNS neuronal antigens, as indicated. (FIG. 3N) Lineage-specific cues promote the generation of specific neuronal subtypes from iENP-6F. (Panel a) Schematic depiction of the experimental procedure used to induce specific neuronal subtypes from iENP-6F. (Panel b) ICC characterization of differentiated iENP-6F under neuronal subtype-specific differentiation conditions by ICC using antibodies against CNS and PNS neuronal antigens, as indicated. (Panel c) Quantification of the indicated neuronal subtypes induced by the conditions described in FIG. 3N, Panel a. GF−, without inducers; GF$^+$, with inducers. (FIG. 3O) Whole-cell patch-clamp recording of iENP-6F-derived neurons. (Panel a) Current recording of a neuron at 4 to 6 weeks post differentiation. (Panel b) Action potentials were induced by current steps from −50 to +120 pA. (Panel c) Inward Na$^+$ currents and outward Ca' currents were induced by voltage steps from −40 to +50 mV. The inward Na$^+$ currents could be blocked with tetrodotoxin (TTX). (FIG. 3P) In vivo transplantation of iENP-6F. (Panel a) IHC staining of the corpus callosum containing iENP-6F transplants using an antibody against human nuclear antigen (HuNu). (Panels b-i) IHC analysis of brain cryosections at 12 weeks post-transplantation using antibodies against HuNu or Stem121 and the indicated neural antigens. (Panel j) Scheme showing the relative position of the indicated cells after transplantation. All quantitative data were obtained from three independent experiments and are presented as means±SD. See also FIG. 9.

Figure 4A:
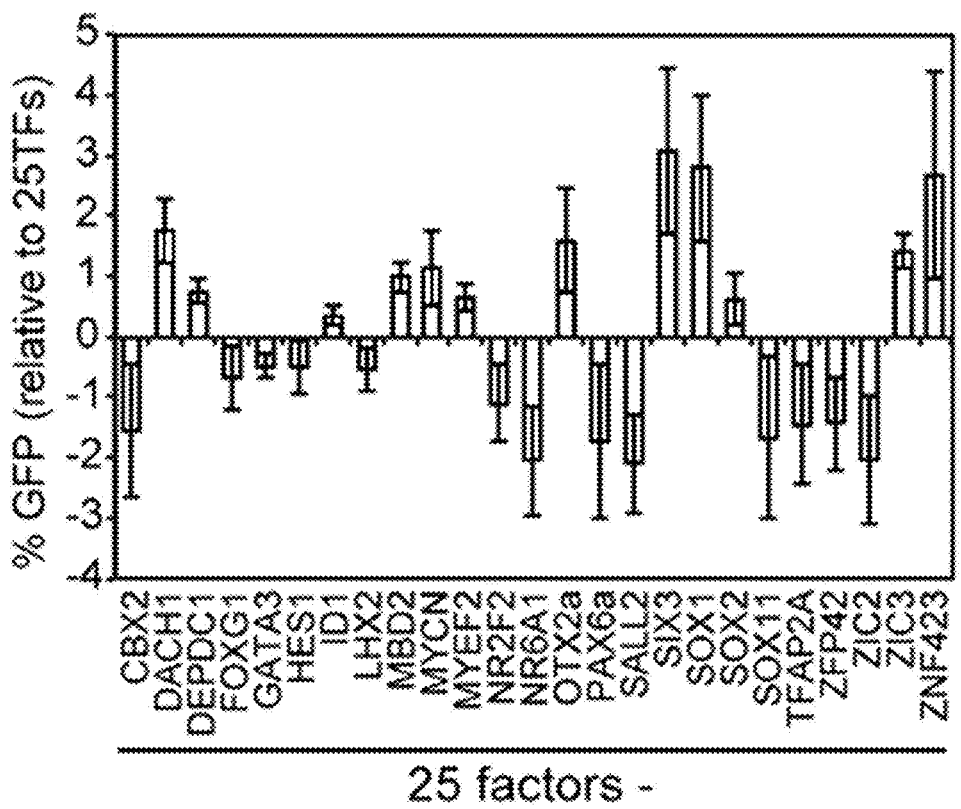
Figure 4B:
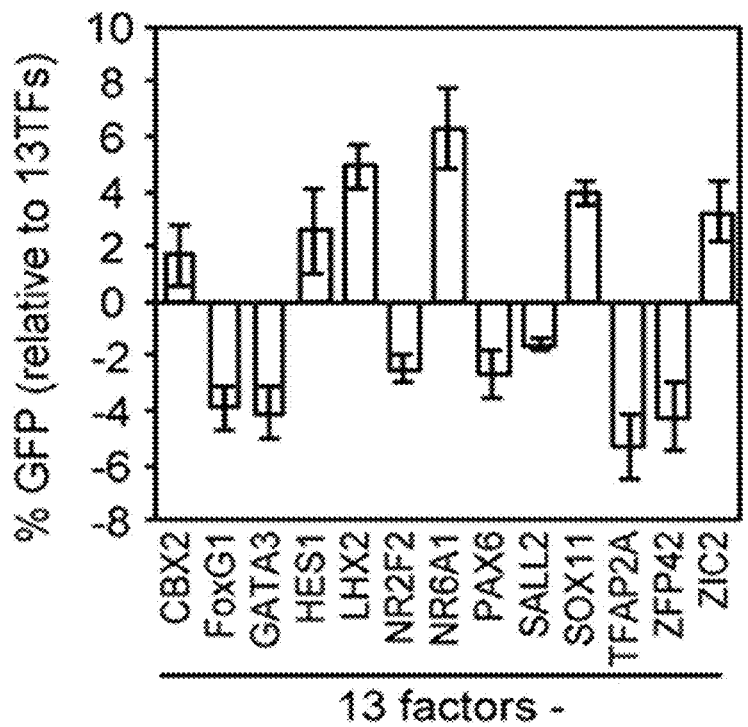

FIGS. 4A-G. Induction of FBs into iENPs by the seven TFs selected using the SOX1:EGFP neural reporter. (FIGS. 4A and 4B) Step-wise selection of potent iENP factors for iENP-7F generation by single TF dropouts from the original 25-TF set (FIG. 4A) and 13-TF set (FIG. 4B). The results are expressed as the relative percentage of SOX1:EGFP$^+$ cells after each TF was removed from the TF combination. (FIG. 4C) Comparison of the efficiency of induction of SOX1:EGFP$^+$ cells from FBs by the 25-, 13-, and 7-TF combinations. (FIG. 4D) Global gene expression heatmap of FBs, hESC-ENP, iENP-7F, and -13F, as determined by microarray analysis. (FIG. 4E) ICC staining of iENPs-7F using antibodies against the indicated NP markers. (FIG. 4F) RT-PCR analysis of endogenous and exogenous expression of the seven TFs using mRNA isolated from iENP-7F. (FIG. 4G) RT-PCR analysis of the indicated neural genes using mRNA isolated from iENP-7F. FB, fibroblasts; NC, negative control (H$_2$O); plasmid: expression plasmids for the indicated genes. All quantitative data were obtained from three independent experiments and are presented as means±SD. See also FIGS. 8-10.

Figure 5A:
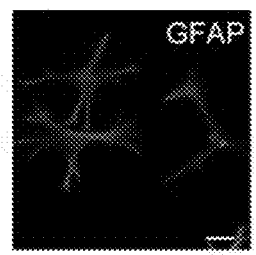
Figure 5B:
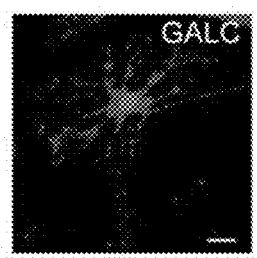
Figure 5C:
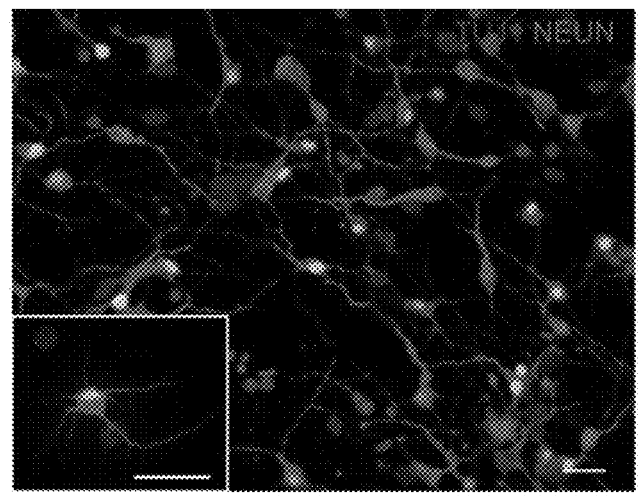
Figure 5D:
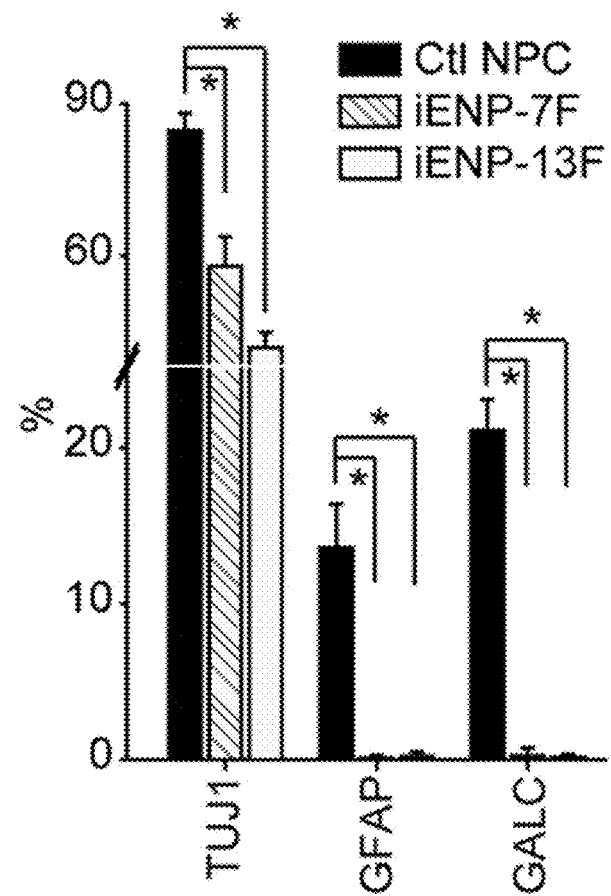
Figure 5E:
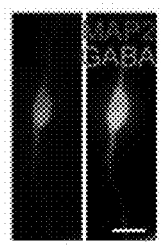
Figure 5F:
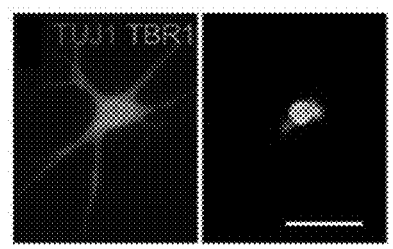
Figure 5G:
Figure 5H:
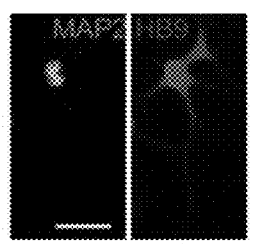
Figure 5I:
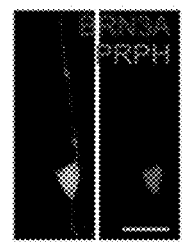
Figure 5J:
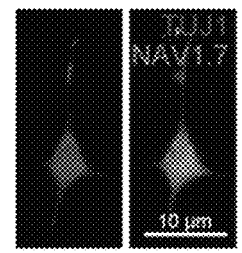

FIGS. 5A-5M. Multipotency of differentiating iENP-7F in vitro and in vivo. (FIG. 5A-5C) ICC staining of differentiated iENP-7F using antibodies against the glial marker GFAP (FIG. 5A), oligodendrocyte marker GALC (FIG. 5B), and neuronal markers, as indicated (FIG. 5C). (FIG. 5D) Quantification and comparison of TUJ1$^+$, GFAP$^+$, and GALC$^+$ cells in differentiated hESC-ENPs, iENP-7F, and iENP-13F. (FIGS. 5E-5J) ICC staining of differentiated iENP-7F with antibodies against CNS and PNS neuronal antigens, as indicated. (FIG. 5K) Lineage-specific cues promote the generation of specific neuronal subtypes from iENP-7F. (Panel a) ICC characterization of differentiated iENP-7F under neuronal subtype-specific differentiation conditions using antibodies against CNS and PNS neuronal antigens, as indicated. (Panel b) Quantification of iENP-7F-derived neuronal subtypes induced by the conditions described in FIG. 3N, Panel a. GF−, without inducers; GF$^+$, with inducers. (FIG. 5L) Whole-cell patch-clamp recordings of iENP-7F-derived neurons. (Panel a) Current recording from a neuron at 4 to 6 weeks. (Panel b) Action potentials were induced by current steps from −80 to +60 pA. (Panel c) Spontaneously firing action potentials were recorded at a subthreshold oscillatory potential of −40 mV. (Panel d) Inward Na$^+$ currents and outward Ca$^{2+}$ currents were induced by voltage steps from −40 to +50 mV. The inward Na$^+$ currents could be blocked by tetrodotoxin (TTX). (FIG. 5M) In vivo transplantation of iENP-7F. (Panel a) IHC staining of the corpus callosum containing iENP-7F transplants using an antibody against human nuclear antigen (HuNu), revealing migration of iENPs into ventricular zones. (Panels b-i) IHC analysis of brain cryosections at 12 weeks post-transplantation using antibodies against HuNu or Stem121 and the indicated neural antigens. All quantitative data were obtained from three independent experiments and are presented as means±SD. See also FIG. 9.

FIGS. 6A-6F. The differential properties of iENP-6F and iENP-7F. (FIG. 6A) Heatmap analysis of global gene expression profiles of undifferentiated iENP-6F, iENP-7F, and FBs. (FIG. 6B) (Panel a) Dynamic changes in the expression of genes characterized by the indicated GO terms. Red, up-regulated; blue, down-regulated. (Panel b) IPA analysis of the activated pathways associated with cell death. (Panel c) Growth curve analysis of the indicated cell populations. (Panel d) ICC staining and quantification of iENPs by BrdU incorporation and TUNEL assays. Nuclei were counterstained with DAPI (blue). (FIG. 6C) Preferential expression of brain regional markers in iENPs. (Panel a) ICC staining of iENPs with antibodies against brain regional antigens, as indicated. (Panel b) Quantification of the percentage of cells expressing brain regional markers, as indicated, in iENPs. (FIG. 6D) Quantification of the percentage of cells expressing the indicated brain regional markers in iENP-derived neurons. (FIG. 6E) Pie chart depicting the proportion of brain regional subtype-associated genes up- and down-regulated between iENP-7F and -6F. (FIG. 6F) Relative expression of brain regional-associated genes in iENP-7F and -6F, as measured by RT-qPCR analysis. FB, forebrain; MB, midbrain; HB, hindbrain; SC, spinal cord. All quantitative data were obtained from three independent experiments and are presented as means±SD.

FIGS. 7A-7E. Recapitulation of disease phenotypes in the diseased iENPs and their neuronal derivatives. (FIG. 7A) Representative images of the morphology and ICC staining for Nestin in (Panel a) AD-iENPs and (Panel b) HD-iENPs. (FIG. 7B) Phase-contrast image of AD-iENP-derived (Panel a) and HD-iENP-derived (Panel b) neurons and ICC staining of AD-iENP (Panel a) and HD-iENP (Panel b) derivatives using antibodies against GFAP, GALC, and TUJ1. (FIG. 7C) Secreted Aβ42/40 ratio; Aβ42 and Aβ40 from AD-iENP-derived neurons. AD2 and AD3, patients carrying PSEN1 mutations. (FIG. 7D) (Panel a) ICC staining analysis of pTAU-expression in AD-iENP-derived neurons using antibodies against TUJ1 and pTAU (AT8). (Panel b) Quantification of the effect of 1-Aza and SB415286 on the reduction in pTAU expression in AD-iENP-derived neurons. AD1, patient carrying the APOE4/E4 mutation. Controls were treated with DMSO. (FIG. 7E) ICC staining (Panel a) and quantification (Panel b) of $\gamma H_2AX^+$ cells in vehicle (DMSO)- and CGS 21680-treated control and HD-iENPs. (Panel c) ICC staining and (Panel d) quantification of $\gamma H_2AX^+$ cells in vehicle (DMSO)- and CGS 21680-treated controls and HD-iENP-derived neurons. All quantitative data were obtained from three independent experiments and are expressed as means±SD. See also FIGS. 12A-12C.

FIGS. 8A-8E. Characterization of iENP-15F and iENP-13F. (FIG. 8A) ICC staining of iENPs induced by the 15 (selected by PAX6:EGFP) and 13 (selected by SOX1:EGFP) TF combinations, using antibodies against the indicated NP markers. Nuclei were counterstained with DAPI (blue). (FIG. 8B) RT-PCR analysis of the indicated genes using mRNA isolated from undifferentiated iENP-15F and -13F. hESC-ENPs and FBs were used as positive and negative controls, separately. (FIG. 8C) PCR analysis of the integration of the indicated exogenous transgenes using genomic DNA isolated from undifferentiated iENP-15F, iENP-6F, iENP-13F, and iENP-7F. The plasmids of indicated genes were used as positive controls. (FIG. 8D) RT-PCR analysis of the indicated endogenous genes using mRNA isolated from undifferentiated iENP-15F and iENP-13F after doxycycline withdrawal. hESC-ENP was used as a positive control. (FIG. 8E) ICC staining of differentiating iENP-15F and iENP-13F with antibodies against TUJ1, GFAP and GALC. Scale bar=10 μm. NC: negative control ($H_2O$). Nuclei were counterstained with DAPI (blue).

Figure 9:
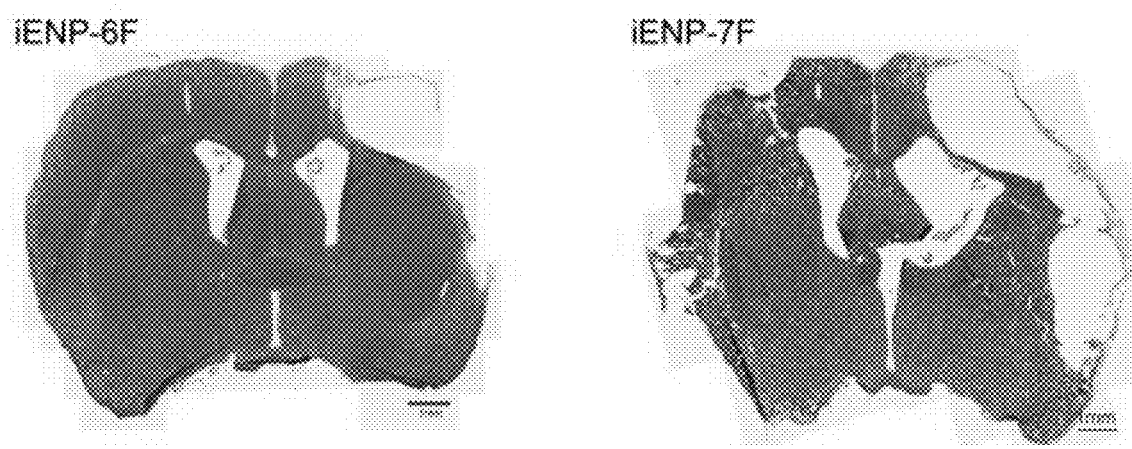

FIG. 9. iENP-6F and iENP-7 do not result in tumor generation after transplantation into the MCAO injured adult rat brain. HE staining of rat brains at 12 weeks after iENP-6F and iENP-7F transplantation.

Figure 10A:
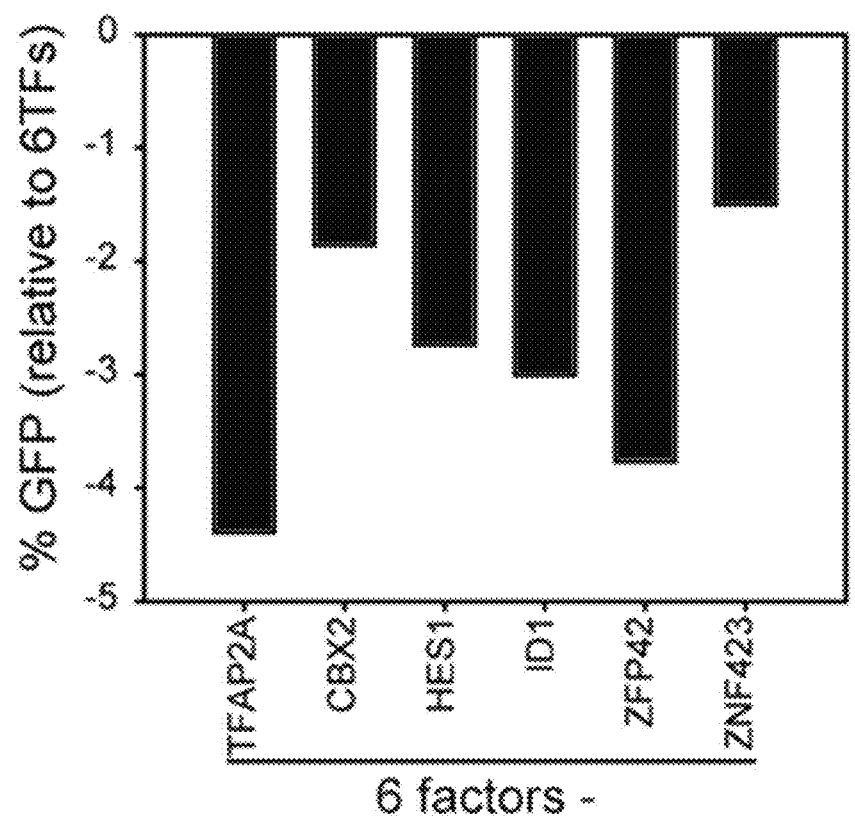
Figure 10B:
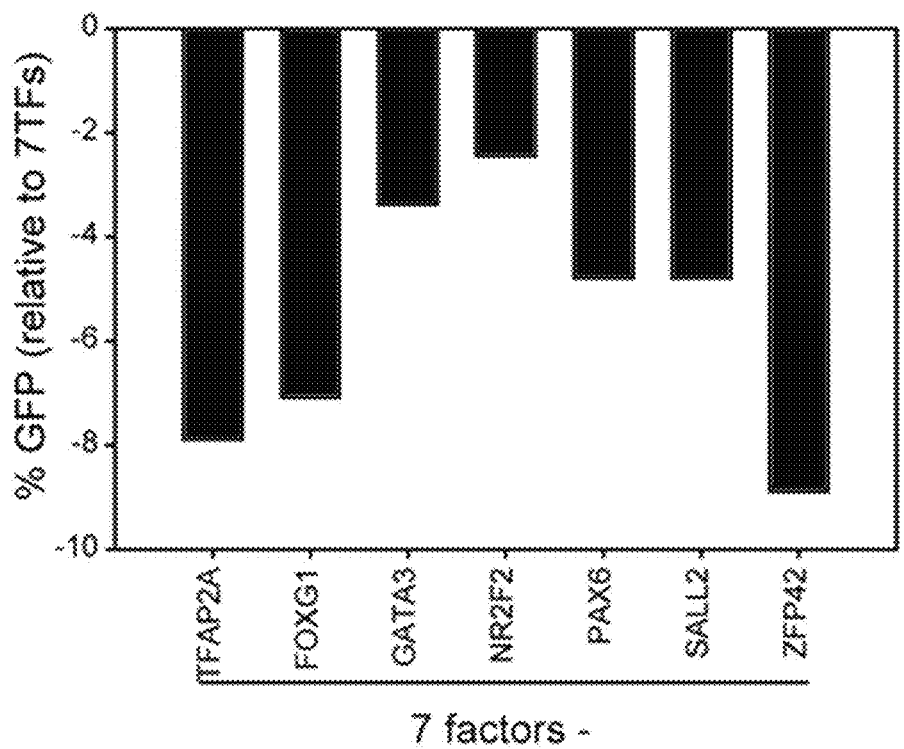
Figure 10C:
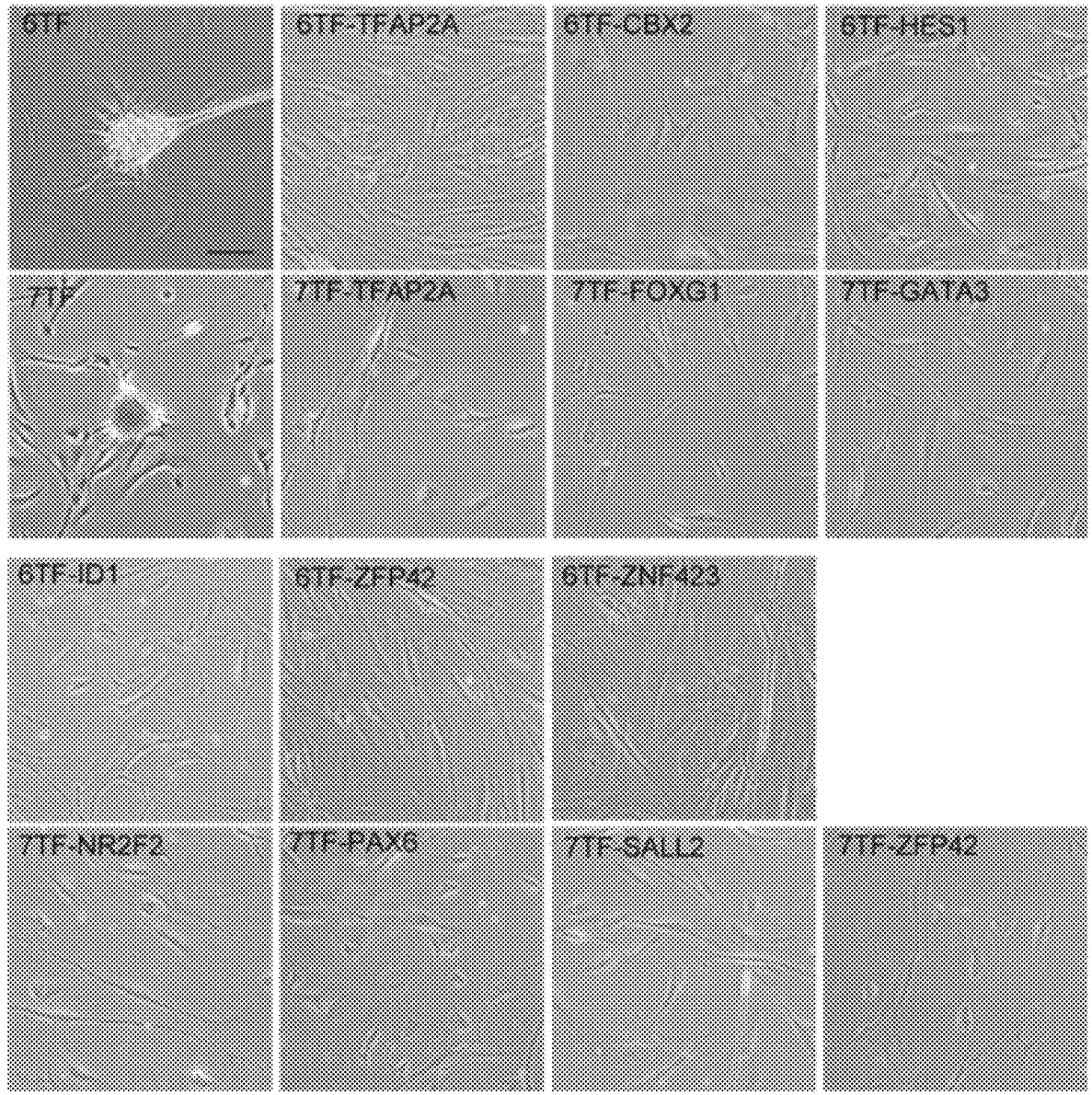

FIGS. 10A-10C. Essential transcription factor combinations for iENP generation. (FIGS. 10A and 10B) Effect of single TF dropouts from (FIG. 10A) the 6TF-set on the induction of PAX6:EGFP+ cells and (FIG. 10B) 7 TF-set on the induction of SOX1:EGFP+ cells. (FIG. 10C) Phase contrast image showing iENP-like colony formation during induction with the transfected TF combination. No colony formation was observed after individual TFs were removed from the original 6 TF or 7 TF combinations.

Figure 11A:
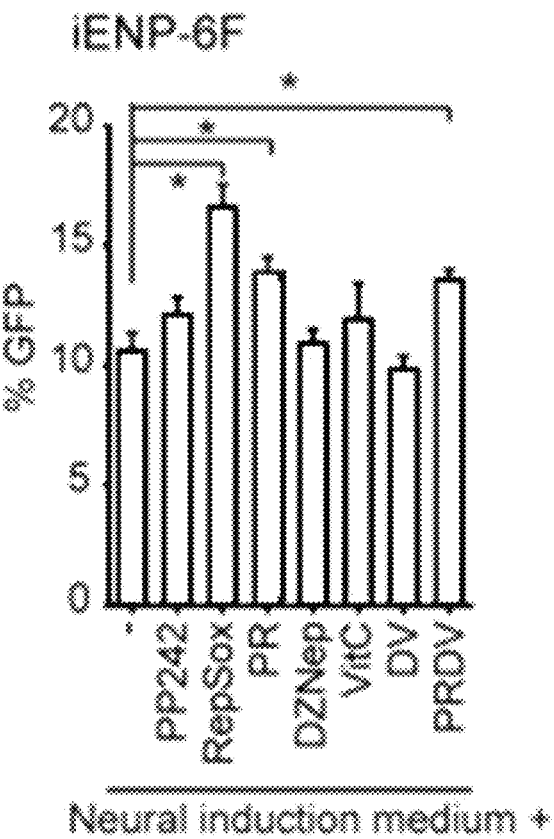
Figure 11B:
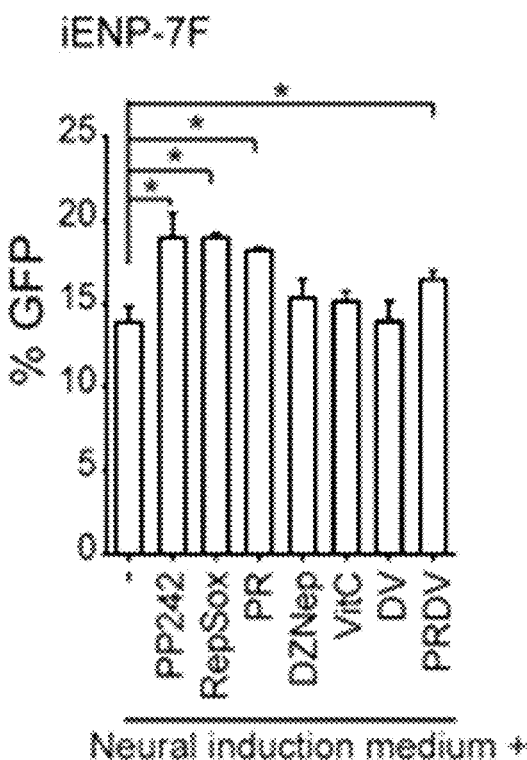

FIGS. 11A and 11B. Small molecule treatment improves iENP generation. Effect of the indicated small molecules on (FIG. 11A) iENP-6F and (FIG. 11B) iENP-7F generation efficiency. Error bars represent the mean±SD. Significance: *P<0.05. (VitC: Vitamin C; PR: PP242+RepSox; DV: DZNep+Vitamin C; PRDV: PP242+RepSox+DZNep+Vitamin C).

Figure 12A:
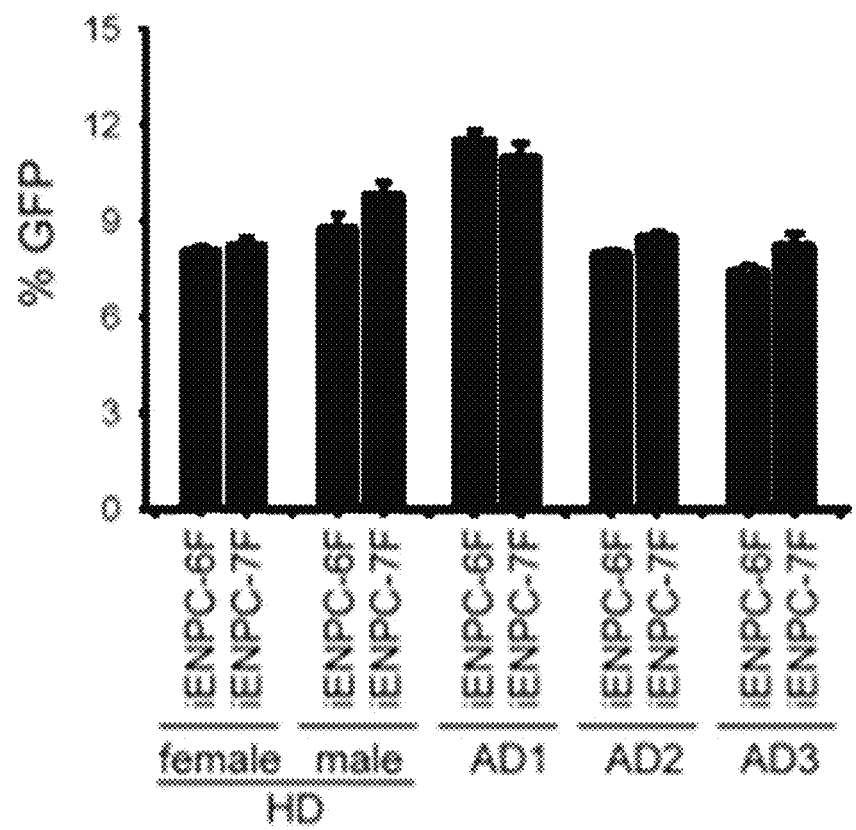
Figure 12B:
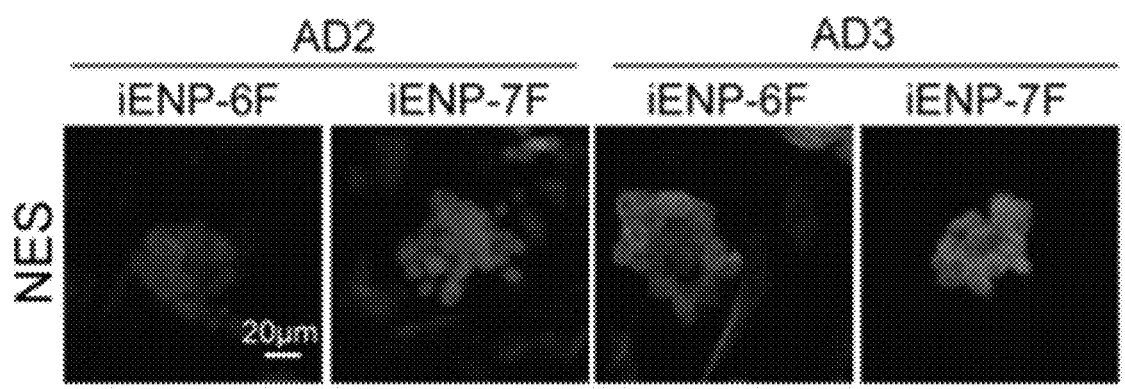
Figure 12C:
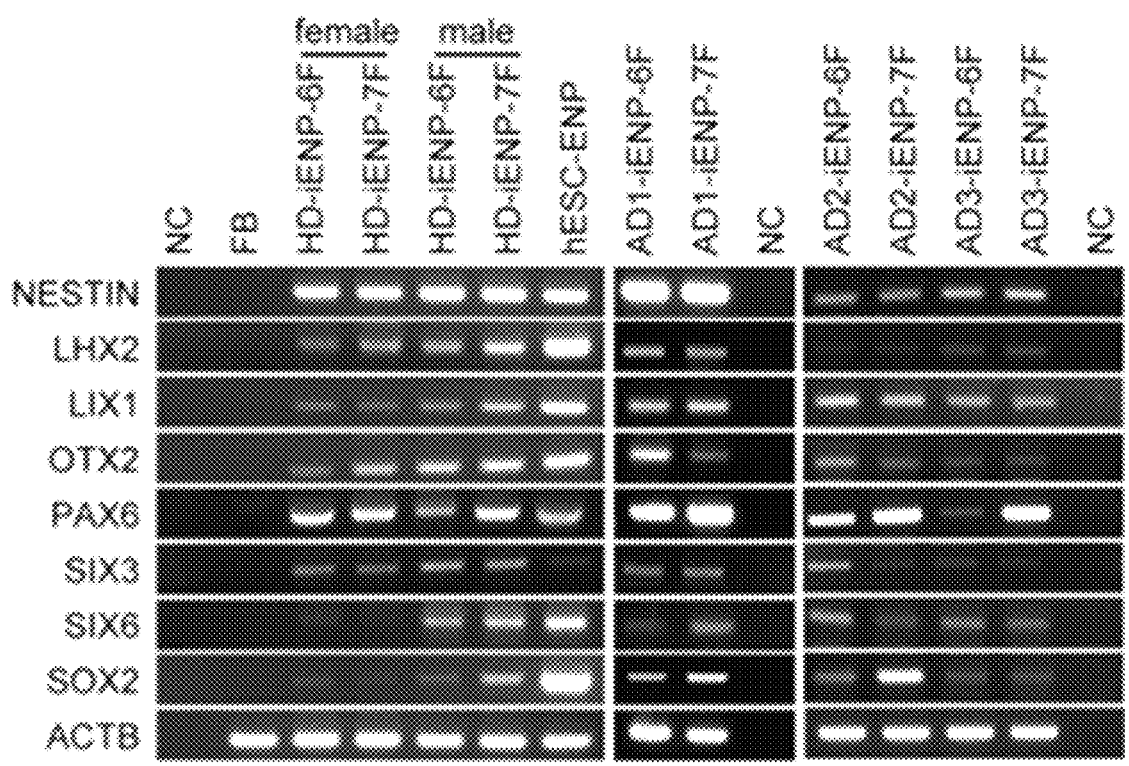

FIGS. 12A-12C. Generation and characterization of HD-iENP and AD-iENP. (FIG. 12A) Induction rate of SOX1:EGFP+(putative iENP-6F) and PAX6:EGFP+(putative iENP-7F) from HD and AD FBs. Error bars represent the mean±SD. (FIG. 12B) ICC staining of AD2- and AD3-iENPs using an antibody specifically against neural marker NES. (FIG. 12C) RT-PCR analysis of the indicated genes using mRNA isolated from undifferentiated HD-iENP-6F, HD-iENP-7F, AD-iENP-6F, and AD-iENP-7F. hESC-ENPs and parental FBs were used as positive and negative controls.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "introduce" refers to the introduction of a polynucleotide (e.g., the polynucleotide of the present kit) into a cell or organism. The nucleic acid of the polynucleotide may be in the form of naked DNA or RNA, associated with various proteins, or incorporated into a vector. The term "introduce" as used herein is intended to convey the broadest possible meaning and encompass the introduction, for example by transfection method (introducing a polynucleotide into eukaryotic cells by physical and/or chemical treatment), transformation method (introducing a polynucleotide into prokaryotic cells by physical and/or chemical treatment), viral method/viral transduction method (introducing a polynucleotide into eukaryotic and/or prokaryotic cells by a virus or a viral vector), conjugation method (introducing a polynucleotide from one cell to another cell by direct cell-to-cell contact or by a cytoplasmic bridge between the cells), and fusion method (fusing two cells, including homotypic cell fusion and heterotypic cell fusion).

As used herein, the term "neurological disease" refers to diseases or disorders that may cause a disturbance in the structure or function of the nervous system resulting from developmental abnormalities, disease, genetic defects, injury or toxin. These diseases or disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems). Examples of the neurological disease include, but are not limited to, neurodevelopment diseases, neurodegenerative diseases or motor neuron diseases.

The term "subject" refers to an animal including the human species that is treatable with the compounds of the present disclosure. The term "subject" is intended to refer to both the male and female gender unless one gender is specifically indicated, and may be any age, e.g., a child or adult.

The present disclosure provides three kits, each of which is useful in inducing the fibroblast cell into an iENP cell thereby selecting a drug candidate suitable for treating a neurological disease (for example, a neurodevelopment, a neurodegenerative disease or a motor neuron disease).

The first kit comprises six polynucleotides (i.e., a first to a six polynucleotides) respectively comprising the genes of CBX2 (SEQ ID NO: 1), HES1 (SEQ ID NO: 2), ID1 (SEQ ID NO: 3), TFAP2A (SEQ ID NO: 4), ZFP42 (SEQ ID NO: 5) and ZNF423 (SEQ ID NO: 6); such a kit is designated as 6TF (6-transcription factor).

Depending on the desired purpose, the first kit may further comprise at least one genes selected from the group consisting of, DACH1 (SEQ ID NO: 7), FOXG1 (SEQ ID NO: 8), MYCN (SEQ ID NO: 9), NR2F2 (SEQ ID NO: 10), NR6A1 (SEQ ID NO: 11), SOX2 (SEQ ID NO: 12), SOX11 (SEQ ID NO: 13), ZIC2 (SEQ ID NO: 14), ZIC3 (SEQ ID NO: 15), GATA3 (SEQ ID NO: 16), PAX6 (SEQ ID NO: 17), SALL2 (SEQ ID NO: 18), LHX2 (SEQ ID NO: 19), MBD2 (SEQ ID NO: 20), DEPDC1 (SEQ ID NO: 21), MYEF2 (SEQ ID NO: 22), OTX2a (SEQ ID NO: 23), SIX3 (SEQ ID NO: 24) and SOX1 (SEQ ID NO: 25).

According to some embodiments of the present disclosure, the first kit further comprises nine polynucleotides (i.e., a seventh to a fifteenth polynucleotides), which respectively comprise the genes of DACH1 (SEQ ID NO: 7), FOXG1 (SEQ ID NO: 8), MYCN (SEQ ID NO: 9), NR2F2 (SEQ ID NO: 10), NR6A1 (SEQ ID NO: 11), SOX2 (SEQ ID NO: 12), SOX11 (SEQ ID NO: 13), ZIC2 (SEQ ID NO: 14) and ZIC3 (SEQ ID NO: 15). In the present disclosure, the kit comprising fifteen polynucleotides (i.e., the first to the fifth polynucleotides) is designated as 15TF.

The second kit comprises seven polynucleotides (i.e., a first to a seventh polynucleotides) respectively comprising the genes of TFAP2A (SEQ ID NO: 4), ZFP42 (SEQ ID NO: 5), FOXG1 (SEQ ID NO: 8), NR2F2 (SEQ ID NO: 10), GATA3 (SEQ ID NO: 16), PAX6 (SEQ ID NO: 17) and SALL2 (SEQ ID NO: 18); such a kit is designated as 7TF.

In general, the second kit may further comprise at least one genes selected from the group consisting of, CBX2 (SEQ ID NO: 1), HES1 (SEQ ID NO: 2), ID1 (SEQ ID NO: 3), ZNF423 (SEQ ID NO: 6), DACH1 (SEQ ID NO: 7), MYCN (SEQ ID NO: 9), NR6A1 (SEQ ID NO: 11), SOX2 (SEQ ID NO: 12), SOX11 (SEQ ID NO: 13), ZIC2 (SEQ ID NO: 14), ZIC3 (SEQ ID NO: 15), LHX2 (SEQ ID NO: 19), MBD2 (SEQ ID NO: 20), DEPDC1 (SEQ ID NO: 21), MYEF2 (SEQ ID NO: 22), OTX2a (SEQ ID NO: 23), SIX3 (SEQ ID NO: 24) and SOX1 (SEQ ID NO: 25).

According to certain embodiments of the present disclosure, the second kit further comprises six polynucleotides (i.e., an eighth to a thirteenth polynucleotides), which respectively comprise the genes of CBX2 (SEQ ID NO: 1), HES1 (SEQ ID NO: 2), NR6A1 (SEQ ID NO: 11), SOX11 (SEQ ID NO: 13), ZIC2 (SEQ ID NO: 14) and LHX2 (SEQ ID NO: 19). In the present disclosure, the kit comprising thirteenth polynucleotides (i.e., the first to the thirteenth polynucleotides) is designated as 13TF.

The third kit comprises twenty-five polynucleotides respectively comprising the genes of CBX2 (SEQ ID NO: 1), HES1 (SEQ ID NO: 2), ID1 (SEQ ID NO: 3), TFAP2A (SEQ ID NO: 4), ZFP42 (SEQ ID NO: 5), ZNF423 (SEQ ID NO: 6), DACH1 (SEQ ID NO: 7), FOXG1 (SEQ ID NO: 8), MYCN (SEQ ID NO: 9), NR2F2 (SEQ ID NO: 10), NR6A1 (SEQ ID NO: 11), SOX2 (SEQ ID NO: 12), SOX11 (SEQ ID NO: 13), ZIC2 (SEQ ID NO: 14), ZIC3 (SEQ ID NO: 15), GATA3 (SEQ ID NO: 16), PAX6 (SEQ ID NO: 17), SALL2 (SEQ ID NO: 18), LHX2 (SEQ ID NO: 19), MBD2 (SEQ ID NO: 20), DEPDC1 (SEQ ID NO: 21), MYEF2 (SEQ ID NO: 22), OTX2a (SEQ ID NO: 23), SIX3 (SEQ ID NO: 24) and SOX1 (SEQ ID NO: 25). In the present disclosure, the third kit that comprises twenty-five polynucleotides (i.e., the first to the twenty-fifth polynucleotides) is designated as 25TF.

According to some optional embodiments of the present disclosure, the present kit (i.e., 6TF, 7TF, 13TF, 15TF or 25TF) may further comprise a reporter polynucleotide, for example, PAX6:EGFP or SOX1:EGFP. In one embodiment, the kit 6TF or 15TF further comprises PAX6:EGFP, which comprises the sequence of SEQ ID NO: 26. In another embodiment, the kit 7TF or 13TF further comprises SOX1: EGFP, which comprises the sequence of SEQ ID NO: 27.

According to embodiments of the present disclosure, the present kit (i.e., 6TF, 7TF, 13TF, 15TF or 25TF) is useful in inducing the fibroblast cells into iENP cells, which then differentiates into astrocytes, oligodendrocytes and/or neurons (including CNS and PNS neural subtypes) under appropriate conditions.

The method for inducing a fibroblast cell into an iENP cell, comprising exposing the fibroblast cell to the present kit in according to any aspects or embodiments disclosed herein.

Optionally, the present kit (i.e., 6TF, 7TF, 13TF, 15TF or 25TF) may further comprise an enhancer, which enhances the effect of the present kit on the production of iENP cells. According to one embodiment of the present disclosure, the enhancer is selected from the group consisting of, RepSox (a transforming growth factorβ (TGFβ) inhibitor), PP242 (an autophage activator), DZNep (a histone methyltransferase inhibitor), vitamin C (a DNA demethylation activator) and a combination thereof. According to one embodiment of the present disclosure, the enhancer is RepSox. According to another embodiment of the present disclosure, the enhancer is the combination of RepSox and PP242. According to still another embodiment of the present disclosure, the enhancer is the combination of RepSox, PP242, DZNep and vitamin C.

As would be appreciated, the polypeptides respectively encoded by the polynucleotides comprised in 6TF, 7TF, 13TF, 15TF or 25TF are also in the scope of the present invention. For example, the present kit may comprise a first to a sixth polypeptides respectively encoded by the genes of CBX2 (SEQ ID NO: 1), HES1 (SEQ ID NO: 2), ID1 (SEQ ID NO: 3), TFAP2A (SEQ ID NO: 4), ZFP42 (SEQ ID NO: 5) and ZNF423 (SEQ ID NO: 6) of 6TF. Alternatively, the present kit may comprises a first to a seventh polypeptides respectively encoded by the genes of TFAP2A (SEQ ID NO: 4), ZFP42 (SEQ ID NO: 5), FOXG1 (SEQ ID NO: 8), NR2F2 (SEQ ID NO: 10), GATA3 (SEQ ID NO: 16), PAX6 (SEQ ID NO: 17) and SALL2 (SEQ ID NO: 18).

Another aspect of the present disclosure is directed to a method of selecting a drug candidate suitable for treating a neurological disease by use of the present kit according to any aspects and embodiments of the present disclosure. The method comprises the steps of, (a) introducing the polynucleotides of the present kit into a fibroblast cell thereby inducing the fibroblast cell into an iENP cell;

(b) incubating the iENP cell of step (a) in a differentiation medium thereby inducing the iENP cell into an astrocyte, an oligodendrocyte or a neuron;

(c) exposing the astrocyte, the oligodendrocyte or the neuron of step (b) to one or more candidate drugs; and (d) selecting the drug candidate from the one or more candidate drugs, wherein the drug candidate changes the phenotype or the gene expression of the astrocyte, the oligodendrocyte or the neuron.

In the step (a), the polynucleotides of the present kit (i.e., 6TF, 7TF, 13TF, 15TF or 25TF) is introduced into a fibroblast cell. Non-limiting examples of introducing polynucleotides into a cell including, but not limited to, calcium phosphate co-precipitation, electroporation, nucleofection, cell squeezing (gently squeezing the cell membrane), sonoporation (inducing pore formation in cell membrane by high-intensity ultrasound), optical transfection (generating a tiny hole in cell membrane by highly focused laser), impalefection (inserting into a cell DNA bound to the surface of a nanofiber), gene gun ("shooting" into the cell nucleus DNA coupled to a nanoparticle of an inert solid), magnetofection (using magnetic force to deliver DNA into target cells), viral transduction (using viruses as a carrier to deliver DNA into target cells), or transfection via a dendrimer, a liposome, or a cationic polymer. In one example, the polynucleotides are introduced into the fibroblast cell via viral transduction (e.g., lentiviral transduction). According to embodiments of the present disclosure, the expression of the polynucleotides induces the introduced fibroblast cell to form an iENP cell. Alternatively, when the kit comprises the polypeptides respectively encoded by the polynucleotides of 6TF, 7TF, 13TF, 15TF or 25TF as mentioned above, then the polypeptides are co-incubated with the fibroblast cell so as to achieve the same effect.

In the step (b), the iENP cell of step (a) is incubated in a differentiation medium. Depending on the desired purpose, the differentiation medium may comprise specified differentiation factors (e.g., ascorbic acid, nerve growth factor (NGF), brain-derived neurotrophic factor (BDNF), fibroblast growth factor (FGF), sonic hedgehog (SHH), and N—[N-(3,5-difluorophenacetyl)-Lalanyl]-(S)-phenylglycine tert-butyl ester (DAPT)) so that the iENP cell would differentiate into an astrocyte, an oligodendrocyte or a neuron (either as a CNS neuron or as a PNS neuron).

The differentiated cell (i.e., differentiated astrocyte, oligodendrocyte or neuron) may serve as a screening model for investigating novel mechanisms involved in the neural signal pathway and/or for selecting a drug candidate. For investigating novel mechanisms, the differentiated cell may be treated with testing molecules so as to discover the potential molecules participating in the regulation of the neural signal pathway. Alternatively, the differentiated cell may be exposed to one or more candidate drugs in the purpose of selecting a drug candidate therefrom that has an effect on the phenotype or the gene expression of the differentiated cell as described in the steps (c) and (d).

According to some embodiments of the present disclosure, the fibroblast cell of step (a) is derived from a healthy subject.

According to other embodiments of the present disclosure, the fibroblast cell of step (a) is derived from a subject having a neurological disease; for example, a neurodevelopment disease, a neurodegenerative disease or a motor neuron disease. Non-limiting examples of the neurodevelopment disease include, but are not limited to, autism spectrum disorder (ASD), fetal alcohol spectrum disorder, Down syndrome, attention deficit hyperactivity disorder, Mendelsohn's syndrome, schizophrenia and fragile-X syndrome. Exemplary neurodegenerative diseases include, but are not limited to, Alzheimer's disease (AD), Parkinson disease (PD), Huntington's disease (HD), frontotemporal dementia (FTD), Friedreich's ataxia, age-related macular degeneration, and Creutzfeldt-Jakob disease. The motor neuron diseases include, but are not limited to, amyotrophic lateral sclerosis (ALS), primary lateral sclerosis (PLS), spinal muscular atrophy (SMA), progressive muscular atrophy (PMA), progressive bulbar palsy (PBP), pseudobulbar palsy, hereditary spastic paraplegia (HSP), Kugelberg-Welander syndrome, Lou Gehrig's disease, Duchenne's paralysis, Werdnig-Hoffmann disease, and benign focal amyotrophy. According to the embodiments, both the iENP and the differentiated cell derived from the fibroblast cell exhibit pathological features as observed in the subject having the neurological disease; and accordingly, the iENP and the differentiated cell provide a treatment model for investigating the potential drug useful in treating the neurological disease.

Another aspect of the present disclosure pertains to a method of treating a subject having or suspected of having a neurological disease. The present method comprises administering to the subject an effective amount of the drug candidate selected by the present kit and/or method in accordance with any aspects and embodiments of the present disclosure.

The present disclosure further provides a method of treating a subject having or suspected of having a neurological disease by use of the present kit (i.e., 6TF, 7TF, 13TF, 15TF or 25TF). The method comprises the steps of, (a) isolating a fibroblast cell from the subject;

(b) introducing the polynucleotides of the present kit into the fibroblast cell thereby inducing the fibroblast cell into an iENP cell;

(c) optionally, incubating the iENP cell of step (b) in a differentiation medium thereby inducing the iENP cell into an astrocyte, an oligodendrocyte or a neuron; and (d) administering to the subject an effective amount of the iENP cell of step (b), or an effective amount of the astrocyte, the oligodendrocyte or the neuron of step (c) so as to alleviate or ameliorate the symptoms associated with the neurological disease.

In the step (a), the fibroblast is isolated from a subject having or suspected of having a neurological disease. The subject is a mammal; for example, a human, a mouse, a rat, a monkey, a chimpanzee, a cat or a dog. Preferably, the subject is a human. The neurological disease treatable with the present method may be a neurodevelopment disease, a neurodegenerative disease or a motor neuron disease.

The steps (b) and (c) of the method for treating the neurological disease are respectively the same as the steps (a) to (b) of the method for selecting drug candidates discussed hereinabove, and hence, detailed description thereof is omitted herein for the sake of brevity.

In the step (d), the iENP cell of step (b), or the induced astrocyte, oligodendrocyte or neuron of step (c) is administered to the subject. Depending on the desired effect, the induced cells may be administered by any suitable route, for example, by enteral, oral, nasal, parenteral (such as intramuscular, intravenous, intraarterial, subcutaneous, intraperitoneal, intracerebral, intracerebroventricular or intrathecal injection), topical or transmucosal administration.

Also disclosed herein are the cells induced by the present kit (i.e., 6TF, 7TF, 13TF, 15TF or 25TF), including an iENP cell, an astrocyte, an oligodendrocyte and a neuron. According to some embodiments of the present disclosure, the present iENP cell is capable of differentiating into an astrocyte, an oligodendrocyte and/or a neuron, in which the neuron may be a CNS neuron or a PNS neuron. The induced cell may be applied to treat a neurological disease. According to certain embodiments of the present disclosure, the induced iENP cell is administered to a subject having or suspected of having a neurological disease; in these embodiments, the induced iENP cell integrates into the CNS or PNS of the subject, and differentiates into an astrocyte, an oligodendrocyte and a neuron (either as a CNS neuron or as a PNS neuron).

In general, the neurological disease may be caused by physical injury, inflammation, aging or gene mutation. Preferably, the neurological disease is a neurodevelopment disease, a neurodegenerative disease, or a motor neuron disease. The neurodevelopment disease treatable with the present method and/or cells include, but are not limited to, autism spectrum disorder (ASD), fetal alcohol spectrum disorder, Down syndrome, attention deficit hyperactivity disorder, Mendelsohn's syndrome, schizophrenia and fragile-X syndrome. The neurodegenerative diseases include, but are not limited to, Alzheimer's disease (AD), Parkinson disease (PD), Huntington's disease (HD), frontotemporal dementia (FTD), Friedreich's ataxia, age-related macular degeneration, and Creutzfeldt-Jakob disease. Non-limiting examples of the motor neuron disease include, amyotrophic lateral sclerosis (ALS), primary lateral sclerosis (PLS), spinal muscular atrophy (SMA), progressive muscular atrophy (PMA), progressive bulbar palsy (PBP), pseudobulbar palsy, hereditary spastic paraplegia (HSP), Kugelberg-Welander syndrome, Lou Gehrig's disease, Duchenne's paralysis, Werdnig-Hoffmann disease, and benign focal amyotrophy.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods
Generation of iENPs

Constructs carrying candidate neural transcription factors were generated from the coding sequences of FOXG1, GATA3, MBD2, MYCN (all from transOMIC technologies), SOX2 (FUW-teto-SOX2; Addgene), CBX2, DACH1, DEPDC1, HES1, ID1, LHX2, MYEF2, NR2F2, NR6A1, OTX2a, PAX6a, SALL2, SIX3, SOX1, SOX11, TFAP2A, ZFP42, ZIC2, ZIC3, and ZNF423 (all from cDNA of hESC $H_9$-derived neural progenitors). The coding sequences were cloned into FUW or FUW-teto vector for further experiments. Reporter constructs were generated by cloning 1.3 kb PAX6 P1 promoter and 1 kb SOX1 promoter into FUW vector to generate PAX6:EGFP and SOX1:EGFP, respectively, and UbC:EGFP was used as a control. The iENPs were generated by producing lentiviral particles carrying candidate transcription factors with the use of 293FT cells in accordance with standard procedures. CCD112SK foreskin fibroblasts (FBs), HD FBs isolated from one female patient and one male patient (both HTT with 431 CAG repeats), and AD FBs (AD1 with a APOE4/E4 mutation, AD2 with the PSEN1 E184D mutation, and AD3 with PSEN1 P264L from Coriell Cell Repository) were infected with lentiviruses carrying the candidate transcription factor or reporter, and then cultured in FB media [DMEM, 10% FBS]. At one day after infection, media were replaced with neural induction media [DMEM/F12, N2 supplement, 20 µg/ml bFGF, 1% NEAA, 2 mM glutamine, 1 mM sodium pyruvate (Invitrogen), 2 µg/ml doxycycline (Sigma), 10 ng/ml LIF (Invitrogen), 3 µM CHIR99021 (Sigma) and 2 µM SB431542 (R&D)]; media were subsequently replaced every 2 days. For small molecule treatment, 10 µM RepSox, 0.1 µM DZNep, 0.1 nM PP242 (Selleckchem) or 50 µg/ml Vitamin C (Sigma) was introduced into neural induction medium. After a week of induction, GFP positive cells were purified on a BD FASCAriaII sorter and planted on matrigel-coated dishes with iENP media containing 2 µg/ml doxycycline [N2B27: 50% DMEM/F12, 50% Neurobasal, 0.5× N2 supplement, 0.5× B27 supplement, 10 µg/ml bFGF, 1% NEAA, 2 mM glutamine, 1 mM sodium pyruvate, 10 ng/ml LIF (Invitrogen), 3 µM CHIR99021 (Sigma), and 2 µM SB431542 (R&D)]. Cells spontaneously formed neural sphere-like structures after 2 or 3 days. The neural sphere-like structures were collected and trypsinized into single cells and then plated on ornithine-laminin coated dishes with iENP media containing 2 µg/ml doxycycline. The efficiency of iENP generation was measured by combining two parameters: the percentage of GFP positive cells driven by either PAX6:EGFP or SOX1:EGFP at day 6 post lentiviral infection, and the percentage of neurosphere formation at day 2 post purification. After 2 to 3 passages, doxycycline was removed from culture media and the cells were maintained and subcultivated every 7 days. After 2 passages without doxycycline, iENPs were examined for expression of neural genes, endogenous neural genes, and exogenous genes by RT-PCR analysis, exogenous gene insertion by PCR analysis, and neural gene expression by ICC analysis.

Differentiation and Drug Testing

General neural differentiation was examined using differentiation media [Neurobasal, B27 supplement, 1% NEAA, 2 mM glutamine, 1 mM sodium pyruvate (Invitrogen), 300 µg/ml dbcAMP, 50 µM ascorbic acid (Sigma), 20 ng/ml BDNF, 20 ng/ml GDNF, 50 ng/ml NGF (Peprotech)], while specific neuronal differentiation were examined using cortical neuronal differentiation media, dopaminergic neuronal differentiation media, and PNS neuronal differentiation media [cortical neuronal differentiation media: Neurobasal, N2 supplement, B27 supplement (Invitrogen), 100 ng/ml SHH, 125 ng/ml Noggin, 250 ng/ml DKK1, 10 ng/ml BDNF, 10 ng/ml bFGF (R&D), 2 µM XAV939, 100 nM LDN93189, 10 µM SB431542, 200 µM ascorbic acid, 200 µM dbcAMP (Sigma); dopaminergic neuronal differentiation media: DMEM/F12, N2 supplement (Invitrogen), 20 ng/ml BDNF, 200 ng/ml SHH, 100 ng/ml FGF8P (R&D), 200 µM ascorbic acid (Sigma); PNS neuronal differentiation media: DMEM/F12, N2 supplement (Invitrogen), 3 µM CHIR99021, 10 µM SU5402, 10 µM DAPT, 200 µM dbcAMP]. For AD drug testing, AD- and control-iENPs were subjected to cortical differentiation. At 7 days after differentiation, cells were treated with SB415286, 1-Azakenpaullone (Selleckchem), or DMSO (Sigma) for 2 days. For HD studies, cells were induced to differentiate and then treated with CGS21680 as previously described.

Aβ Measurement

AD-iENP and CCD1112sk (CTL)-iENP were plated in 24 well plates ($8 \times 10^5$ cells/well) and then induced to differentiate into cortical neurons. Media were harvested at 20 days after plating and stored at −80 degree till analysis. Secreted Aβ42 and 40 were measured using Aβ42 and 40 human ELISA kits (KHB3544 and KHB3482, Thermo Fisher Scientific), and detected using a Benchmark plus microplate spectrophotometer (BIO-RAD). Each experiment was performed in biological triplicates.

Electrophysiology

For electrophysiological recording, iENP-derived neurons were further co-cultured with mouse glial cells in neuronal maturation media [B27: Neurobasal, B27 supplement, 1% NEAA, 2 mM glutamine, 1 mM sodium pyruvate (Invitrogen), 20 ng/ml BDNF, 20 ng/ml GDNF, 50 ng/ml NGF (Peprotech)] for 2 weeks. Mouse glial cells were isolated from the brains of P1 ICR mice and subcultivated for more than 3 passages to eliminate neuron contamination, which was confirmed by examination of mouse Tuj1 mRNA and protein expression using RT-PCR analysis and ICC analysis, respectively. Electrophysiological properties were determined by whole cell patch clamp recording at room temperature with external solution [115 mM NaCl, 2 mM KCl, 10 mM HEPES, 1.5 mM MgCl 2, 3 mM CaCl 2, 10 mM Glucose. pH 7.4, 300 mOsm]; the patch pipettes were 5-10 MΩ filled with internal solution [130 mM K-gluconate, 10 mM NaCl, 2 mM MgCl2, 10 mM HEPES, 0.5 mM EGTA, 3 mM ATP]. TTX (1 µM) in external solution was used to block TTX-sensitive sodium channels. Seal resistance in the whole cell mode was over 1GΩ. Cells were visualized under a 20× Olympus BX51WI water-immersion lens with Sony CCD; action potentials were recorded in whole cell current-clamp mode, and sodium current was recorded in voltage-clamp mode using a Multiclamp 700B (Molecular Devices) controlled by Signal software and Power 1401 (CED). Results were analyzed using Microsoft Excel 2010.

Reverse Transcription Polymerase Chain Reaction (RT-PCR)

RNA was extracted with TRIzol reagent following the standard extraction protocol (Molecular Research Center). Extracted RNA was reverse-transcribed into cDNA with SuperScript III Reverse Transcriptase (Invitrogen). Each PCR used 25 ng of cDNA. GoTaq Green Master Mix (Promega) was used for RT-PCR analysis. For quantitative PCR (qPCR), SYBR® FAST 2× qRT-PCR Master Mix (KAPA) and a 7900HT Fast Real-Time PCR System (Applied Biosystems) were used.

Flow Analysis

To evaluate the proportion of GFP-positive cells, cells were dissociated and then resuspended in PBS. The results were recorded and analyzed with a BD FACSCalibur flow cytometer. The effect of withdrawing an individual factor was determined by normalizing the proportion of each set to the control.

Immunocytochemical (ICC) and Immnohistochemical Analysis (IHC)

The ICC procedure was performed as previously described. For IHC analysis of transplanted rat brains, samples were dehydrated using 20% sucrose in PBS and embedded in O.C.T. compound (Tissue-Tek). Consecutive coronal sections (12 µm) were performed using a Leica CM3050S Sliding Microtome. Tissue slices were post-fixed with 4% paraformaldehyde for 30 minutes at room temperature and cold methanol for 30 minutes. The primary and secondary antibodies are respectively listed in Tables 1 and 2. Signals were recorded using a Zeiss microscope and Spot software.

TABLE 1

Primary antibody

| Name | Company | Catalog | Host | Dilution |
|---|---|---|---|---|
| BLBP | Millipore | ABN14 | Rabbit | 1:500 |
| γH2AX | Millipore | 05-636 | Mouse | 1:500 |
| GABA | Sigma | A0310 | Mouse | 1:100 |
| GALC | Chemicon | MAB342 | Mouse | 1:200 |
| GFAP | Dako | M0761 | Mouse | 1:100 |
| GFAP | Chemicon | AB5804 | Rabbit | 1:500 |
| GFP | Abcam | Ab13970 | Chicken | 1:500 |
| HB9 | Santa cruz | Sc-22542 | Goat | 1:200 |
| HOXB4 | DSHB | | Rat | 1:50 |
| Human nuclei | Chemicon | MAB1281 | Mouse | 1:200 |
| ISL1 | DSHB | | Mouse | 1:50 |
| LHX/Lim2 | Chemicon | AB5756 | Rabbit | 1:200 |
| MAP2 | Chemicon | AB5622 | Rabbit | 1:200 |
| MBP | Chemicon | AB980 | Rabbit | 1:10000 |
| NCAD | Santa cruz | Sc-8424 | Mouse | 1:50 |
| Nestin | Chemicon | MAB5326 | Mouse | 1:200 |
| Nestin | Chemicon | ABD69 | Rabbit | 1:500 |
| NeuN | Chemicon | MAB377 | Mouse | 1:10 |
| NFH | Sigma | N4142 | Rabbit | 1:200 |
| NG2 | Chemicon | AB5320 | Rabbit | 1:200 |
| OTX2 | R&D | AF1979 | Goat | 1:100 |
| PAX6 | DSHB | | Mouse | 1:50 |
| AT8 | Thermo | MN1020 | Mouse | 1:40 |
| PRPH | Chemicon | AB1530 | Rabbit | 1:200 |
| SOX1 | Chemicon | AB15766 | Rabbit | 1:100 |
| STEM121 | STEM CELLs | AB-121-U-050 | Mouse | 1:200 |
| SYP | DSHB | | Mouse | 1:50 |
| TBR1 | Millipore | AB10554 | Rabbit | 1:200 |
| Tuj1 | Chemicon | MAB1637 | Mouse | 1:200 |
| Tuj1 | Covance | MRB-435P | Rabbit | 1:10000 |
| ZO1 | Santa cruz | Sc-10804 | Rabbit | 1:200 |

TABLE 2

Secondary antibody

| Host | Target | Fluorescence | Company | Catalog | Dilution |
|---|---|---|---|---|---|
| Donkey | Mouse | 488 | Thermo | R37114 | 1:500 |
| Donkey | Mouse | 594 | Thermo | R37115 | 1:500 |
| Donkey | Rabbit | 488 | Thermo | R37118 | 1:500 |
| Donkey | Rabbit | 594 | Thermo | R37119 | 1:500 |
| Donkey | Goat | 488 | Thermo | A-11055 | 1:500 |
| Goat | Chicken | 488 | Thermo | A-11039 | 1:500 |
| Donkey | Rat | 594 | Thermo | A-21209 | 1:500 |

Cell Transplantation and Ethics Statement

Long-Evans rats (7-8 weeks old) were subjected to ischemia by right MCAO and CCAs for 30 minutes, and then 50,000 undifferentiated iENP-6F and iENP-7F were injected into the cerebrum (A/P:0.3 cm, M/L: −2.0 cm, D/V: −2.8 cm, TB: −3.0 cm). After 12 weeks, rats were sacrificed and perfused with 4% paraformaldehyde in 0.1M PB buffer, and then the brains were isolated. All the animal experiments were approved by the Animal Care and Use Committee of Academia Sinica, and performed in accordance with the Institutional Animal Care and Use Committee of Academia Sinica.

Cell Proliferation and Death Analysis iENP-6F, iENP-7F, NP, and GFP control cells were seeded in 24 wells in iENP medium without doxycycline. Cell number was counted at day 1, 2, 3, 4, and 5. Results are shown relative to those of day 1. BrdU (93-3943, Thermo Fisher Scientific) incorporation and TUNEL (G3250, Promega) assays were performed following standard protocols. Images were detected using a Zeiss microscope and Spot software, and analyzed by Metamorph software.

Microarray Analysis

Total RNA was extracted from dermal fibroblasts, CCD112SK foreskin fibroblasts, hESC $H_9$-derived neural progenitors, iENP-6F, iENP-7F, iENP-15F, and iENP-13F using TRIzol reagent (Invitrogen). Two biological duplicates per cell type were examined. All gene expression results were obtained by the Affymetrix Gene Expression Service Laboratory at Academia Sinica, Taiwan. Chips were scanned with an Affymetrix GeneChip Scanner 7G and data were analyzed by GeneSpring X software (Agilent, Santa Clara, Calif., USA). Raw data were normalized independently for each experiment using Robust Multichip Average. Gene expression patterns were analyzed by Genespring Software and Ingenuity Pathway Analysis Software. The NCBI accession number for the microarray data reported in this article is GSE81554.

Figure 1A:
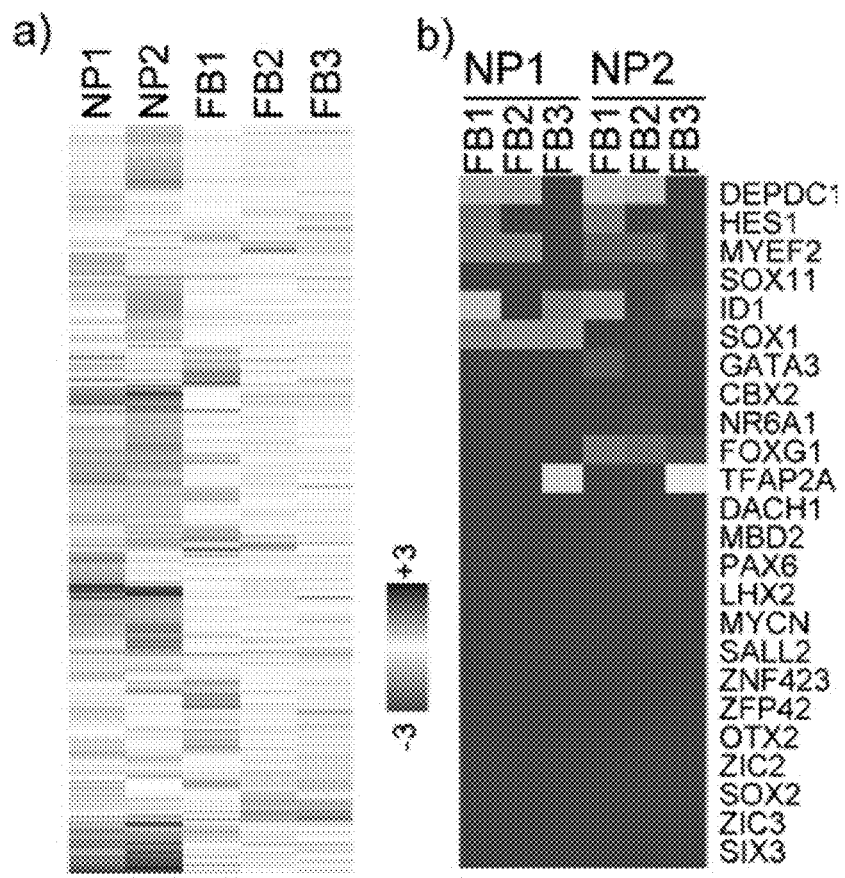
FIGS. 1A-1D. Induction of human FBs into iENPs by 25 nTFs highly expressed in hESC-ENPs.
Figure 8A:
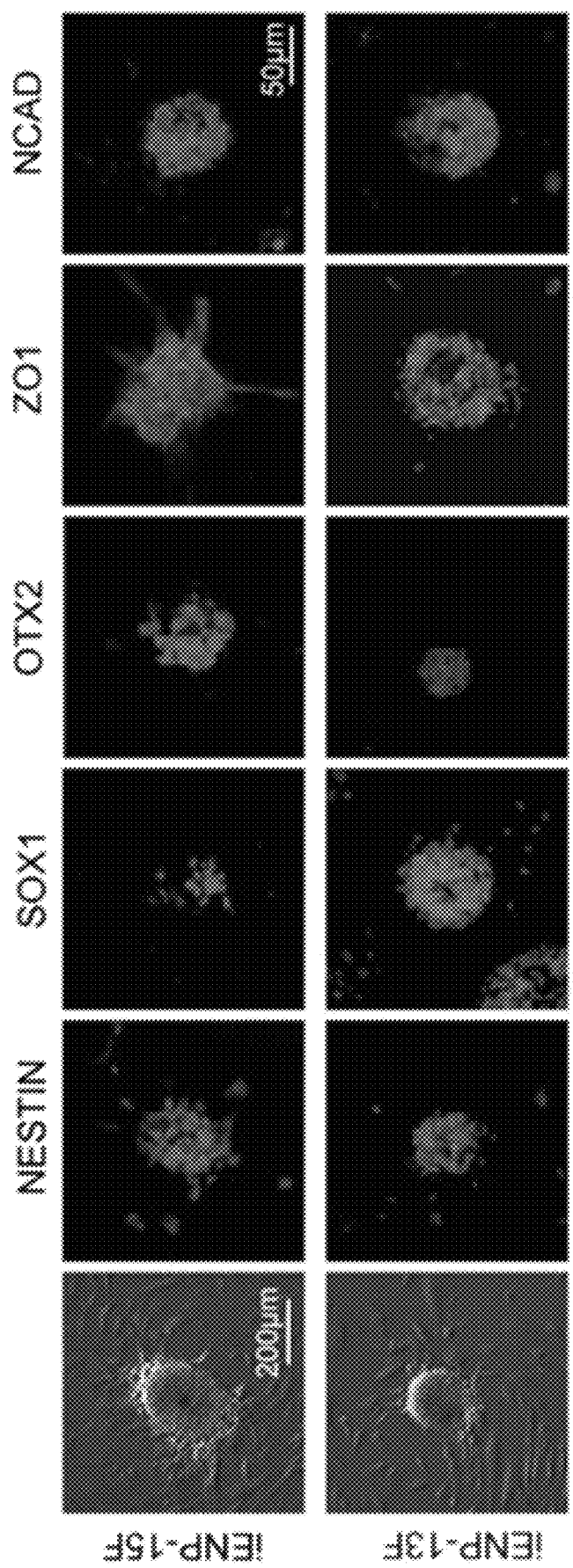
Figure 8B:
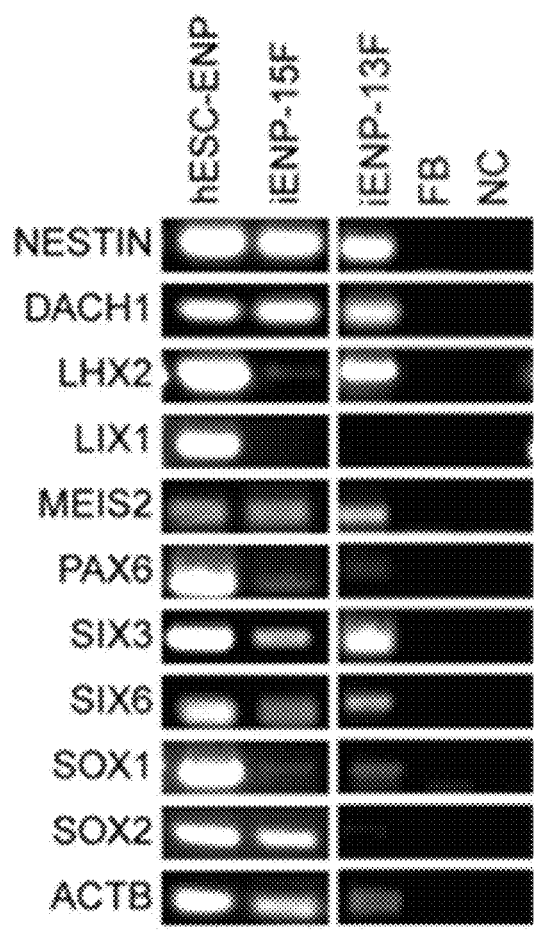

Example 1 Conversion of iENPs from Human FBs 1.1 Selection of Transcription Factors To screen potential TFs for iENP generation, we compared the global gene expression profiling of multiple hESC-ENP and FB populations by microarray analysis (FIG. 1A, Panel a). Twenty-four TFs were selected based on their greater levels of expression in hESC-ENPs than in FBs (FIG. 1, Panel b). NR2F2 was also selected because it was previously reported to be crucial for neural differentiation. As the hESC-ENP-TFs were highly expressed in heterogeneous ENP populations derived from hESCs, there is a possibility that certain combinations of our 25 hESC-ENP-TFs may be able to induce different types of ENPs from FBs. To this end, two reporter systems, PAX6:EGFP and SOX1:EGFP, were created to monitor the progression of neural fate conversion and to evaluate ENP induction efficiency, as both PAX6 and SOX1 have been reported to be expressed in hESC-ENPs. We confirmed that these reporters are expressed in hESC-ENPs (FIGS. 8A and 8B).

Figure 1B:
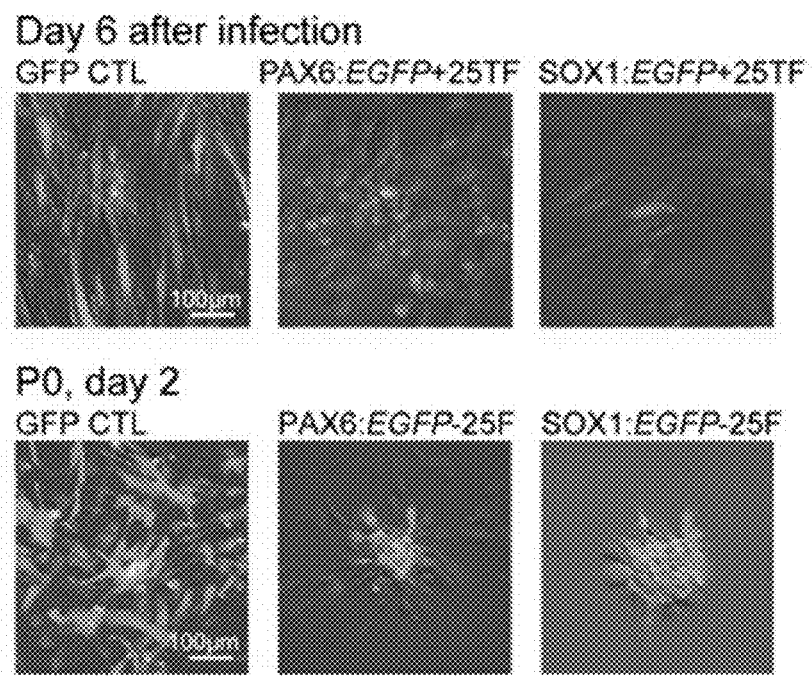
Figure 1C:
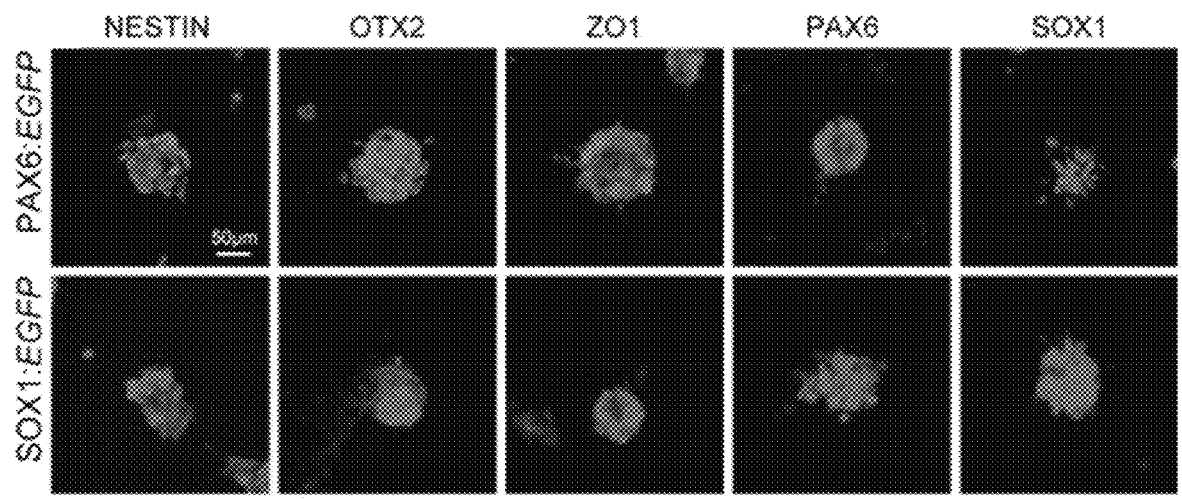
Figure 1D:
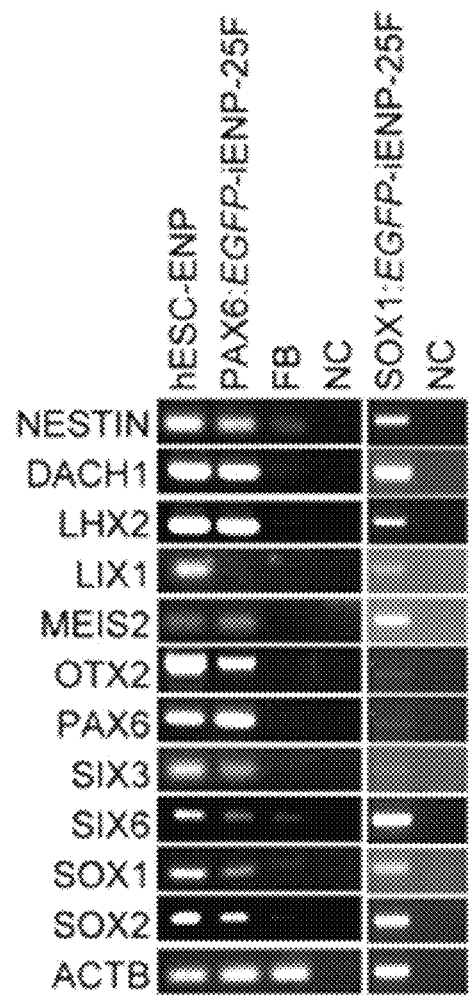
Figure 2A:
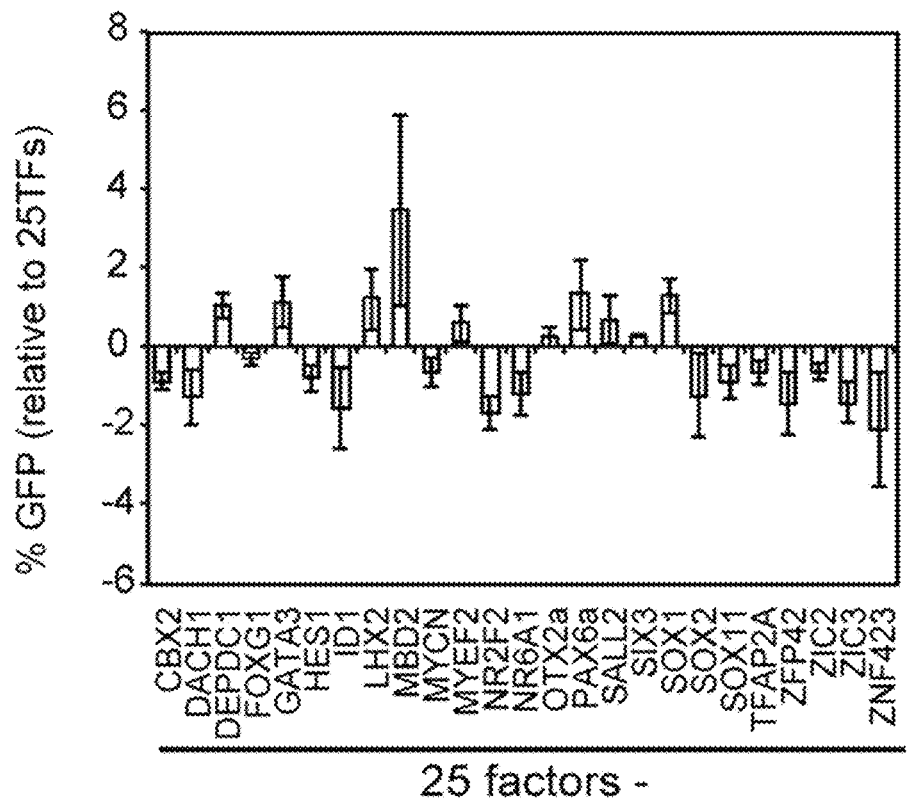
FIGS. 2A-2G. Induction of FBs into iENPs by six TFs selected using the PAX6:EGFP neural reporter.
Figure 4C:
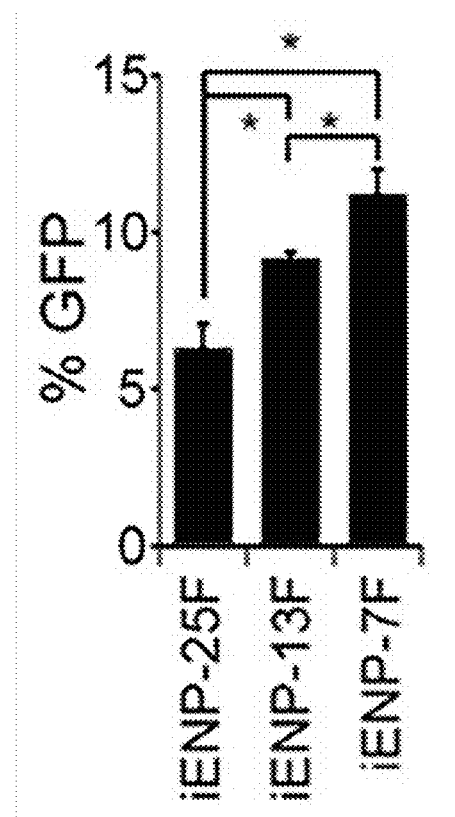

To generate iENPs, we simultaneously infected FBs with lentiviruses encoding each of the aforementioned 25 TFs as well as the neural reporter, PAX6:EGFP or SOX1:EGFP. At around 6 days post lenti-viral infection, PAX6:EGFP$^+$ cells with a rounded shape started to emerge, whereas no morphological change was noted in the control FBs infected with UbC:EGFP (FIG. 1B). Similar results were also observed in FBs transfected with the 25 TFs and SOX1:EGFP (FIG. 1B). The proportion of PAX6:EGFP$^+$ and SOX1:EGFP$^+$ cells was 5.31±0.38% and 6.31±0.45%, respectively (FIGS. 2C and 4C). After purification of the PAX6:EGFP$^+$ or SOX1:EGFP$^+$ cells by FACS and subsequent culture, the purified cells started to spontaneously form neural sphere-like structures (FIG. 1B) at 2 days after re-platting, whereas no neural sphere-like structures was observed in the control cells (FIG. 1B). We then characterized the putative iENPs generated using the 25 TFs (iENP-25F) with various assays. Through ICC and RT-PCR analysis, we showed that PAX6:EGFP- and SOX1:EGFP-iENP-25F expressed common neural markers, such as NESTIN, OTX2 and ZO1 (FIG. 1C), and neural genes (FIG. 1D).

Figure 4D:
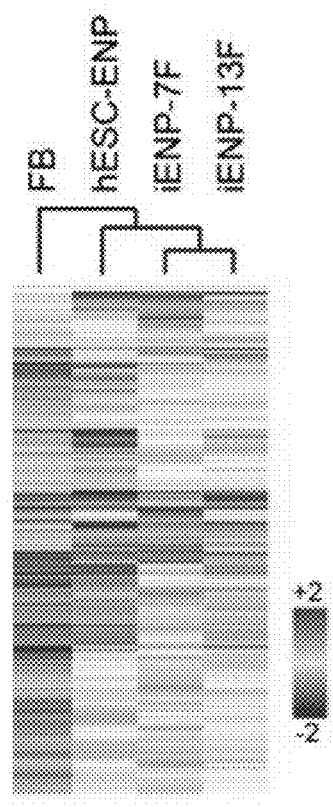
Figure 8C:
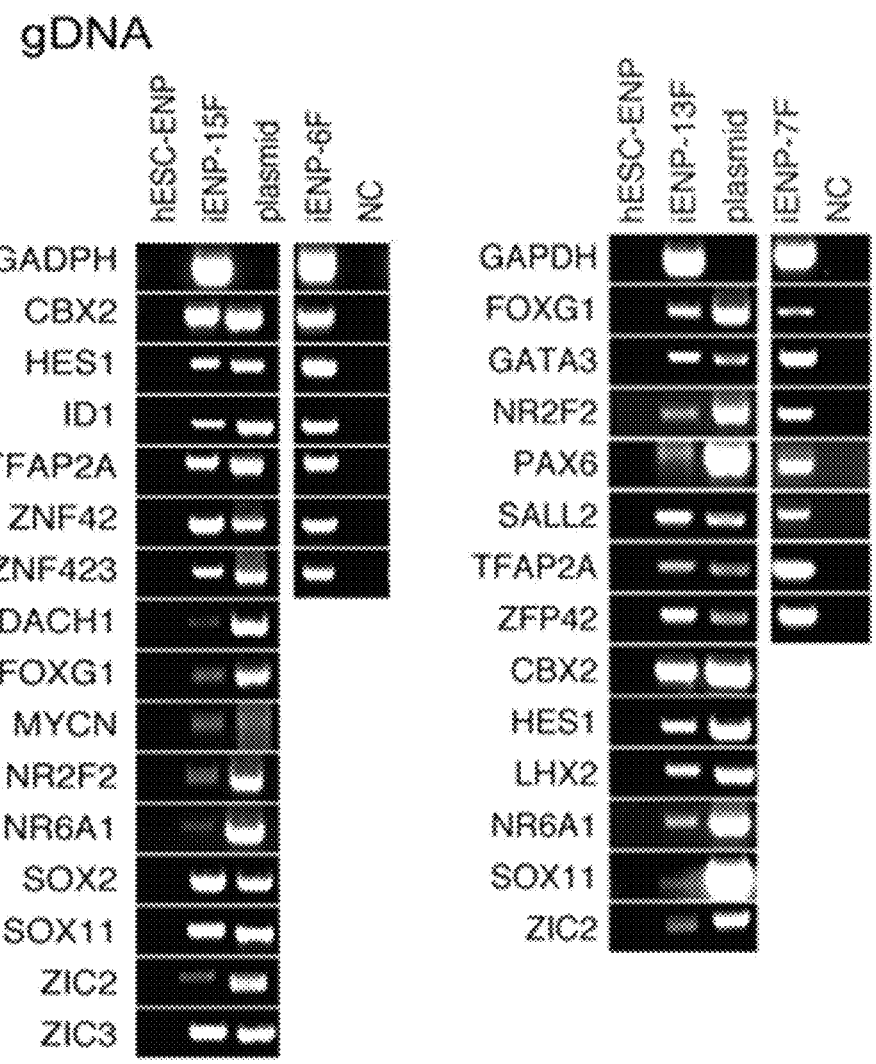
Figure 8D:
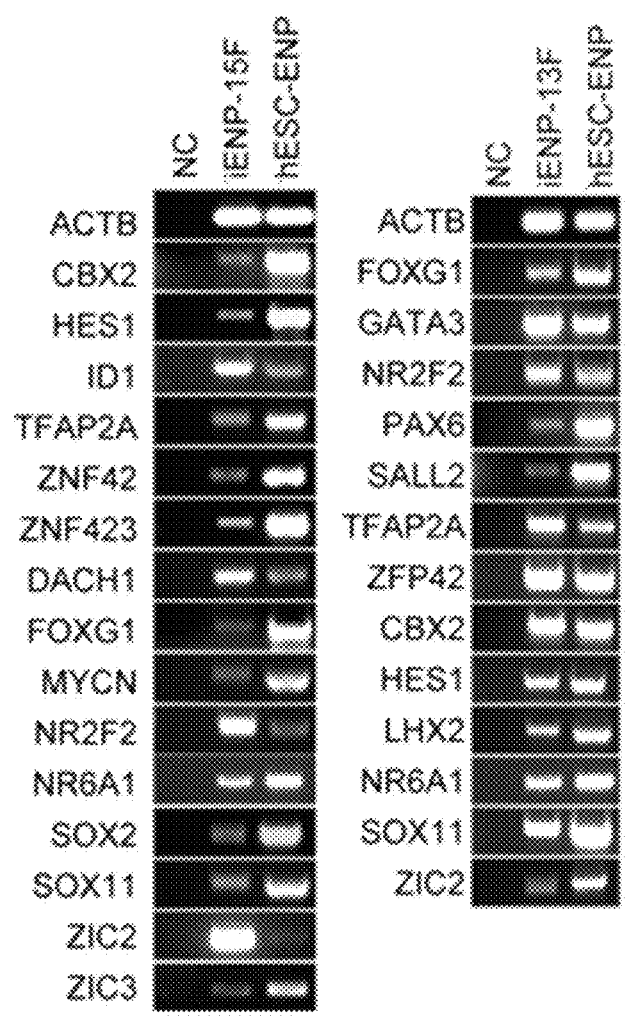
Figure 8E:
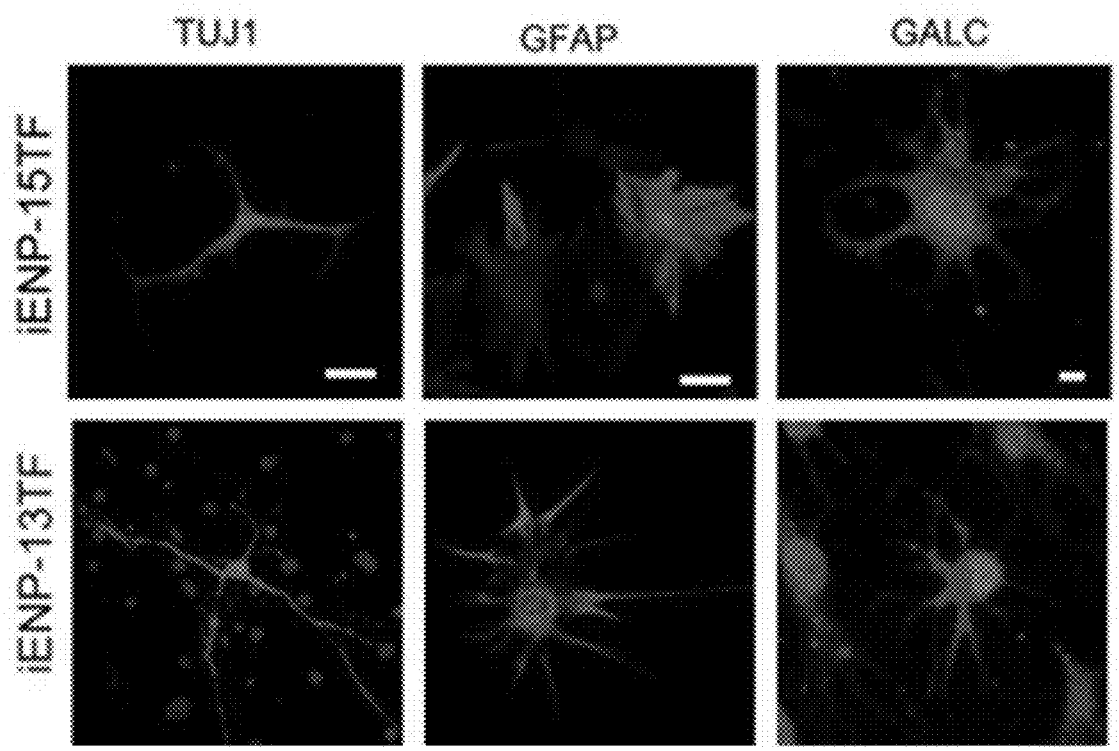

To reduce the number of TFs for iENP generation, we performed a two-step selection of TFs for iENP induction by removing one TF from the 25-TF pool each time, and infecting the FBs with the remaining 24 TFs with PAX6:EGFP or SOX1:EGFP reporters. The impact of the missing TF on the induction of PAX6:EGFP$^+$ or SOX1:EGFP$^+$ cells was then evaluated by flow cytometric analysis (FIGS. 2A and 4A). Accordingly, we identified 15 factors (CBX2, DACH1, FOXG1, HES1, ID1, MYCN, NR2F2, NR6A1, SOX2, SOX11, TFAP2A, ZFP42, ZIC2, ZIC3, ZNF423) and 13 (CBX2, FOXG1, GATA3, HES1, LHX2, NR2F2, NR6A1, PAX6, SALL2, SOX11, TFAP2A, ZFP42, ZIC2) whose removal significantly decreased the generation of the PAX6:EGFP or SOX1:EGFP$^+$ cells, respectively, compared to their counterparts generated with 25 TFs (FIGS. 2A and 4A). To determine whether iENPs can be induced from FBs using the deduced TF combinations, we infected FBs with lentiviruses encoding the selected 15 or 13 TFs under a doxycycline-inducible overexpression system. After purification of PAX6:EGFP$^+$ or SOX1:EGFP$^+$ cells by FACS, our subsequent analysis demonstrated that iENP-15F and iENP-13F, like iENP-25F, can spontaneously form neural sphere-like structures, and expressed neural markers and genes as revealed by ICC and RT-PCR analysis (FIGS. 8A-8B). Through PCR and RT-PCR analyses, we also confirmed integration of the exogenous transgenes into genomic DNA and activation of endogenous ENP gene expression after doxycycline withdrawal, respectively (FIGS. 8C-8D). Further microarray analysis revealed that the global gene expression profiles of iENP-15F and iENP-13F were overtly different from those of their respective parental FBs, and more similar to those of hESC-ENPs (FIGS. 2D and 4D). Importantly, in vitro differentiation of iENP-15F and -13F demonstrated that they are able to spontaneously give rise to TUJ1$^+$ neurons, GFAP$^+$ astrocytes, and GALC$^+$ oligodendrocytes (FIG. 8E). These results suggested that iENP-15F and iENP-13F possess the common characteristics of NPs, and are able to give rise to the major components of the human nervous system.

Figure 2B:
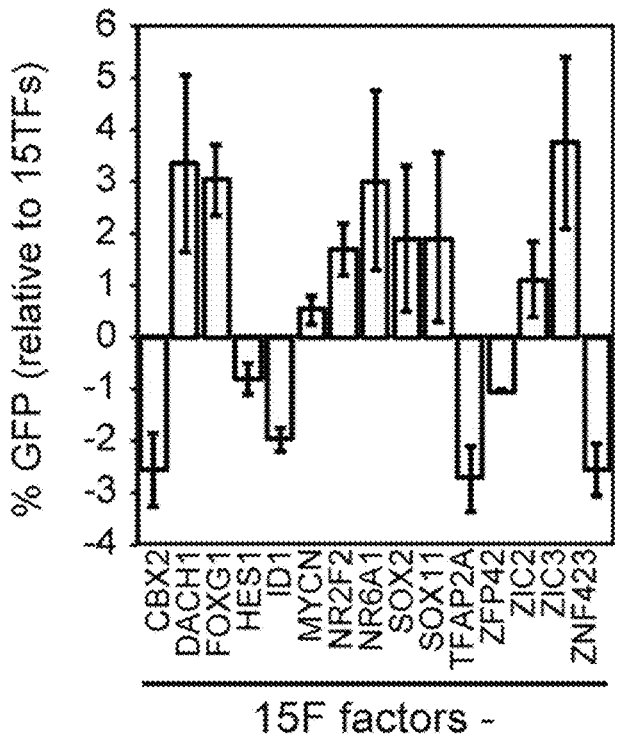
Figure 2C:
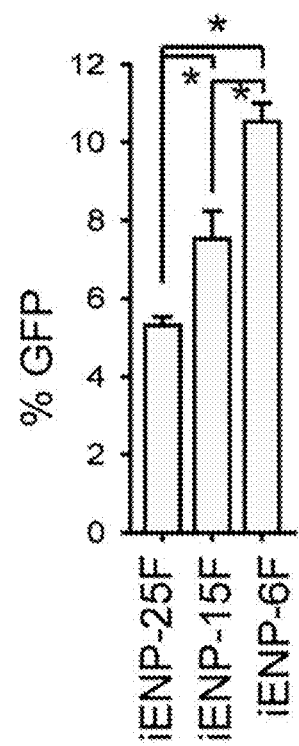
Figure 2D:
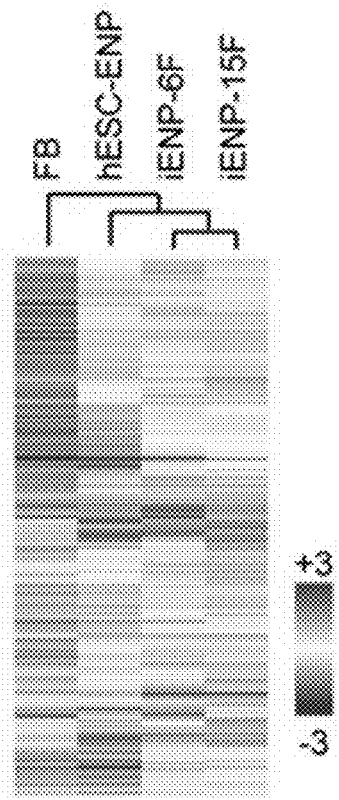
Figure 2E:
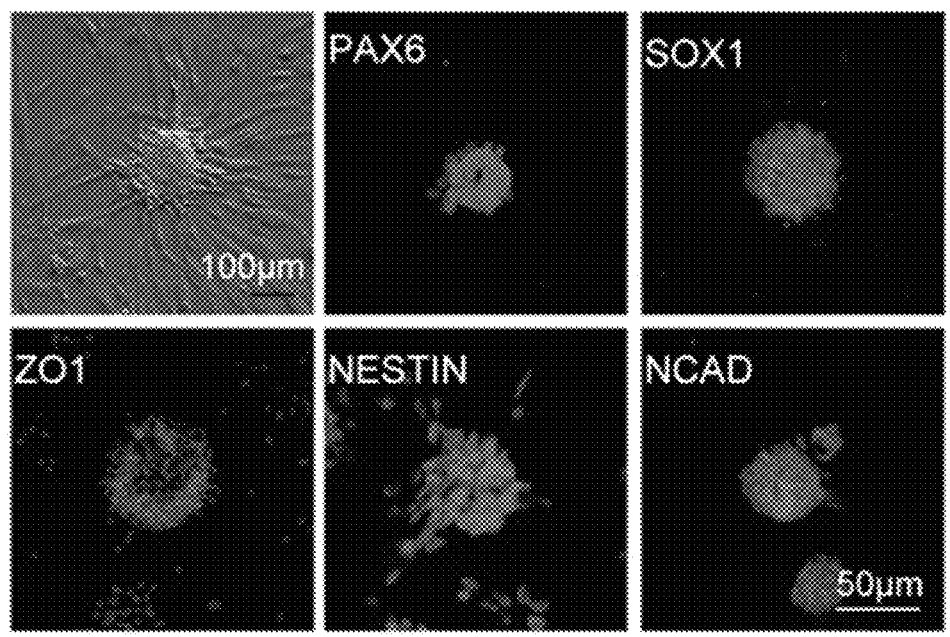
Figure 2F:
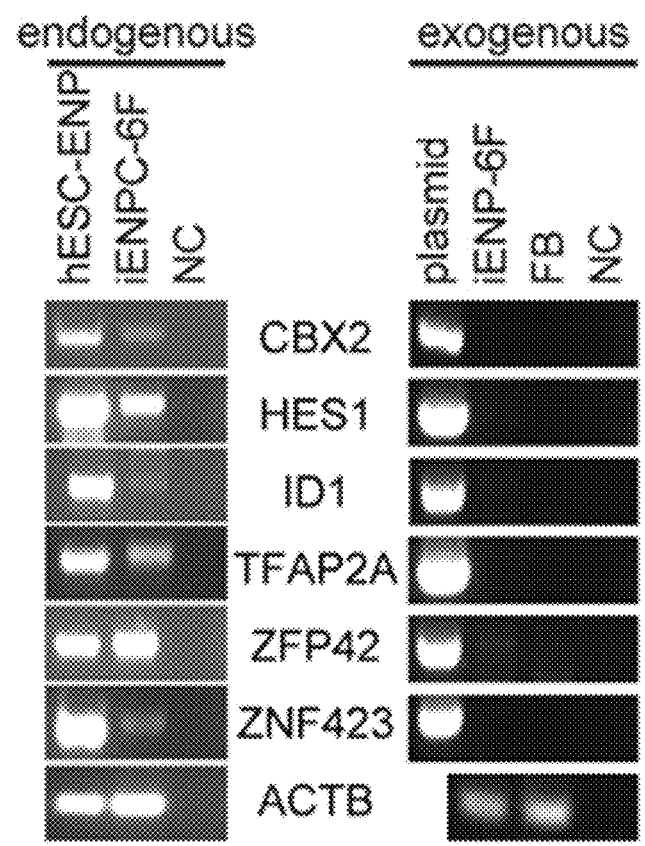
Figure 2G:
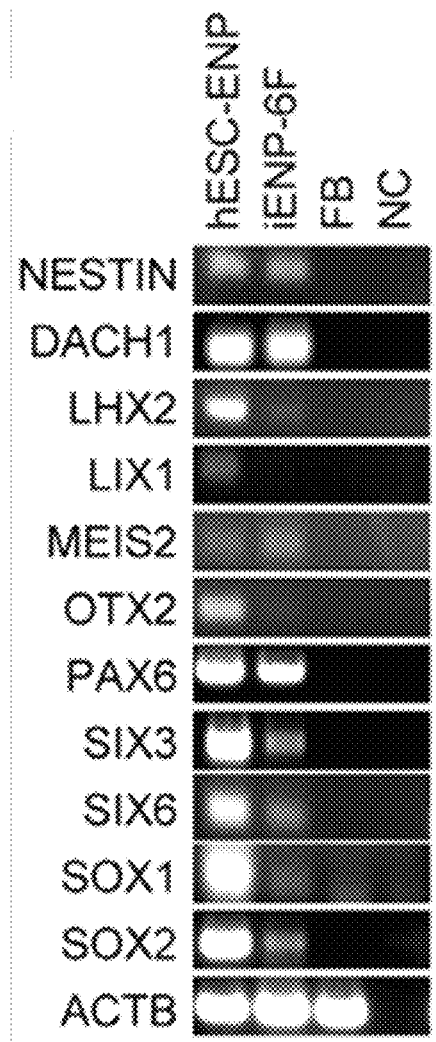
Figure 4E:
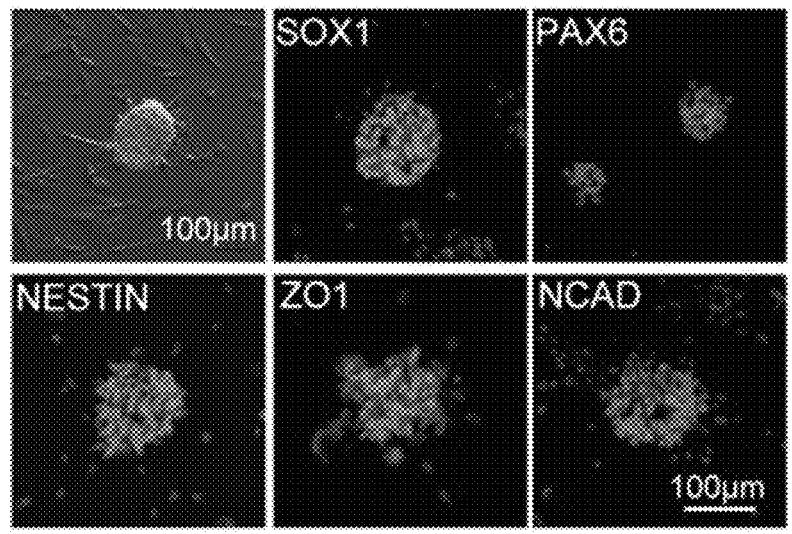
Figure 4F:
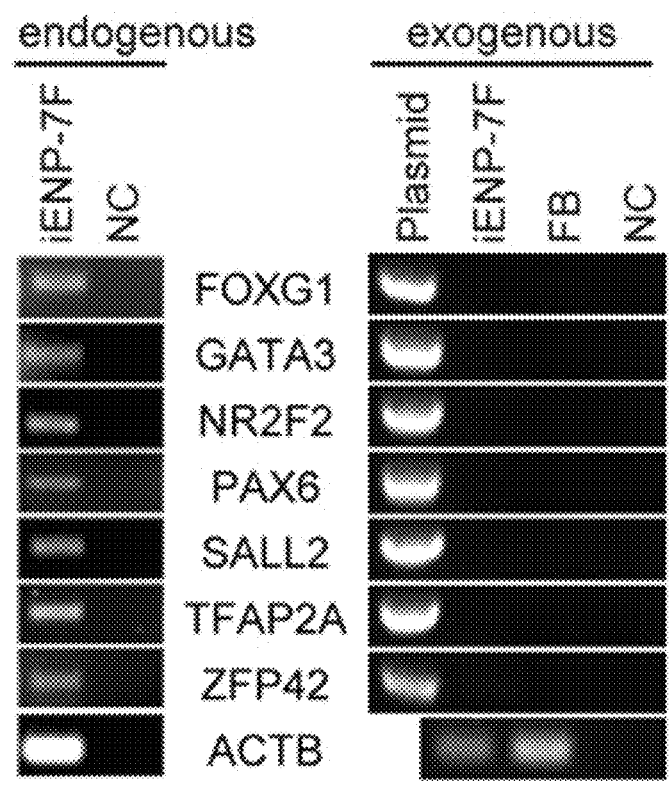
Figure 4G:
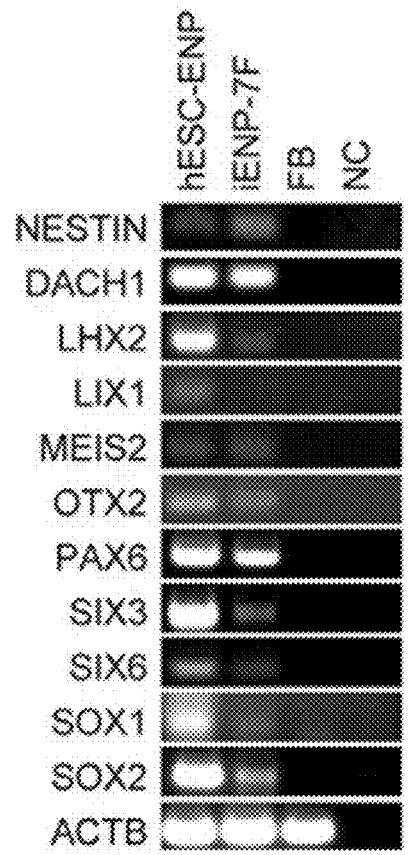

To define the minimal number of TFs required for iENP generation, we carried out an extra run of TF selection (through a procedure similar to that described above) to select the most potent TFs for iENP induction (FIGS. 2B and 4B). After the second TF selection, we found that removal of CBX2, HES1, ID1, TFAP2A, ZFP42, or ZNF423 (6F) and FOXG1, GATA3, NR2A2, PAX6, SALL2, TFAP2A, or ZFP42 (7F) from the 15-TF and 13-TF combinations caused a significant reduction of the generation of PAX6:EGFP$^+$ or SOX1:EGFP$^+$ cells, respectively (FIGS. 2B and 4B). After infection with the identified 6 TFs or 7 TFs, 10.54±0.47% of PAX6:EGFP$^+$ cells and 11.22±0.44% of SOX1:EGFP$^+$ cells were purified by FACS (FIGS. 2C and 4C). Similar to our observations for iENP-25F, -15F and -13F (FIGS. 1C and 9A), FACS-isolated iENP-6F and iENP-7F also spontaneously formed neural sphere-like structures (FIGS. 2E and 4E). Notably, removal of any individual factor from the 6- or 7-TF combination significantly compromised the generation of PAX6:EGFP$^+$ or SOX1:EGFP$^+$ cells, respectively (FIGS. 10A-10B), as well as neural-sphere like structure formation (FIG. 10C). Collectively, these results suggested that each TF in the 6- and 7-TF combinations are essential for iENP generation. Further, PCR analysis confirmed the integration of exogenous transgenes in genomic DNA of iENP-6F and iENP-7F (FIG. 8C), and RT-PCR analysis revealed that the expression of the exogenous transgenes was completely silenced, while the expression of the corresponding endogenous genes was activated in iENP-6F and -7F after doxycycline withdrawal (FIGS. 2F and 4F). Clustering global gene expression analysis by GeneSpring software showed that the gene expression profiles of iENP-6F and -7F were closer to those of hESC-ENPs than those of their parental FBs (FIGS. 2D and 4D) and expressed ENP markers and genes, as revealed by ICC and RT-PCR analysis (FIGS. 2E, 2G, 4E and 4F). Moreover, iENP-6F and -7F could be sub-cultivated for more than 20 passages while maintaining a normal karyotype (FIG. 9A), and subsequently cryopreserved and thawed for further expansion without losing their NP characteristics. Together, these results demonstrated that the morphological, biochemical and molecular traits of both iENP-6F and -7F resemble those of hESC-ENPs.

1.2 Small Molecules Promoted the Generation of iENP

As accumulating evidence indicated that small molecules can enhance reprogramming efficiency in various cellular systems, we proceeded to examine if small molecule treatment could further improve the efficiency of iENP generation. We selected a panel of candidate small molecules, including TGFβ inhibitor, RepSox, autophagy activator, PP242, histone methyltransferase inhibitor, DZNep, and DNA demethylation activator, Vitamin C, all of which have been reported to promote pluripotency reprogramming or direct cell fate conversion. To this end, we added the selected small molecules individually or in combination into the culture after the FBs were infected with virus encoding the 6 or 7TF combinations and the PAX6:EGFP or SOX1:EGFP reporter, respectively. The effect of individual or multiple small molecules on iENP generation was evaluated by FACS analysis of PAX6:EGFP or SOX1:EGFP positive cells (FIGS. 11A and 11B). Overall, our results showed that treatment with RepSox or RepSox plus PP242 significantly improved the efficiency of iENP-6F or iENP-7F generation, respectively (FIGS. 11A and 11B). Thus, these results suggested that small molecules can enhance TF-mediated induction of iENP from FBs.

Example 2 Multipotency of iENP In Vitro

As functional ENPs can differentiate into astrocytes, oligodendrocytes, and neurons, we examined the ability of our iENPs to differentiate in vitro (FIGS. 3 and 5). After 2-3 weeks of differentiation, GFAP$^+$ and GALC$^+$ cells and abundant neuron-like cells exhibiting neuronal process and expressing neuronal marker MAP2, NEUN, or TUJ1 were readily observed in both differentiating iENP-6F (FIGS. 3A-3D) and -7F cells (FIGS. 5A-5C) under neural differentiation conditions. Notably, the synapse marker synaptophysin (SYP) was also found co-expressed with mature neuronal marker, NFH (FIG. 3E). Further, quantification of the proportion of cell expressing TUJ1 GFAP, and GALC in the differentiating iENPs by ICC analysis revealed that the neuronal differentiation ability of iENP-6F was similar to that of hESC-ENPs, whereas iENP-15F was less able to generate neurons as compared to hESC-ENPs and iENP-6F, suggesting that removal of the 9 TFs from the 15-TF combination further enhanced the neuronal propensity of iENP-6F (FIG. 3F). The astrocyte and oligodendrocyte differentiation abilities of iENP-6F and -15F were significantly lower than those of hESC-ENPs (FIG. 3F), and iENP-15F exhibited poorer ability to generate oligodendrocytes as compared to iENP-6F (FIG. 3F). On the other hand, the neuronal differentiation abilities of iENP-7F and -13F were similar, but lower than that of hESC-ENPs (FIG. 5D). Both iENP-7F and -13F exhibited significantly lower ability to generate astrocytes and oligodendrocytes (FIG. 5D) as compared to hESC-ENPs.

Figure 5K:
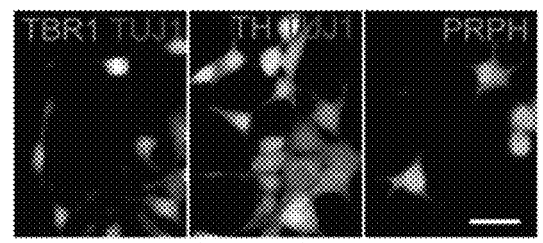
Figure 5K:
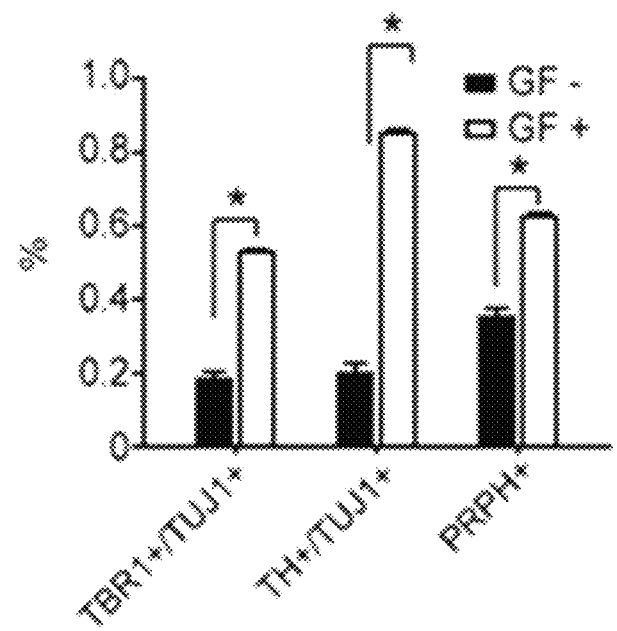

To determine whether iENPs can differentiate into various neuronal, we interrogated the iENP-6F and -7F-derived neuronal population with a panel of neuronal markers (FIGS. 3G-3M and 5E-5J). ICC analysis revealed that both iENP-6F and -7F can give rise to various neuronal subtypes, including GABA$^+$ (FIGS. 3G and 5E), TBR1$^+$ cortical (FIGS. 3H and 5F), TH+ dopaminergic (FIG. 3N, Panel b; and FIG. 5K, Panel a), HB9$^+$/ISL1$^+$ motor (FIGS. 3J, 3K and 5H) and BRN3A$^+$, PRPH$^+$, or NAV1.7$^+$ peripheral neurons (FIGS. 3L, 3M and 5I-5J). As hESC-ENPs can be coaxed by extrinsic stimuli to differentiating into specific neuronal subtypes, we examined whether our iENPs respond in a similar manner. To this end, iENPs were exposed to differentiation conditions for cortical, dopaminergic, and peripheral neuron generation (FIGS. 3N and 5K). ICC analysis with antibodies against TBR1, TH, or PRPH revealed that exposure to specific neuronal differentiation conditions significantly improved the generation of the representative neuronal subtypes (cortical, dopaminergic, or peripheral neurons, respectively) from the iENPs (FIGS. 3N and 5K). These findings suggest that iENPs are multipotent and able to respond to specific differentiation cues in a manner similar to hESC-ENPs.

Figure 5L:
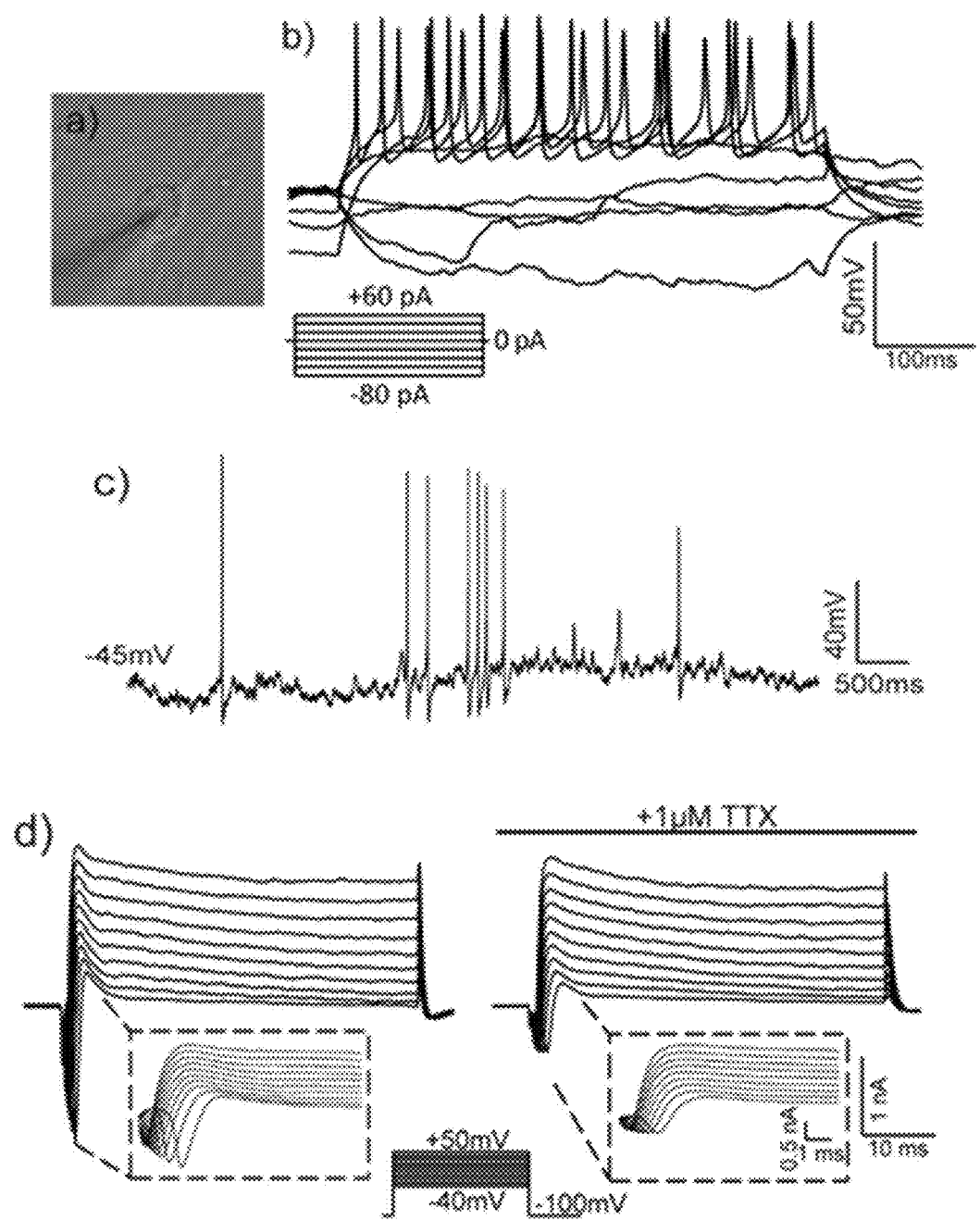

Next, we explored whether the iENP-derived neurons possess functional electrophysiological properties similar to those of neurons. We cultured iENP-derived neurons in neuronal maturation medium for 2 weeks, and then subjected them to whole-cell patch-clamp recoding, revealing that the resting membrane potential was $-35.25\pm0.64$ mV in iENP-6F-derived neurons (FIG. 3O, Panel a) and $-64.3\pm17.96$ mV in iENP-7F-derived neurons (FIG. 5L, Panel a). Action potentials could be elicited by membrane depolarization in current clamp mode (FIG. 3O, Panel b; and FIG. 5L, Panel b), and spontaneous action potentials were recorded in iENP-derived neurons (FIG. 5L, Panel c). Sodium channel-mediated inward currents were blocked by tetrodotoxin (TTX), a Na$^+$ ion channel-specific inhibitor (FIG. 3O, Panel c; and FIG. 5L, Panel d). These results suggested that the iENP-derived neurons possess functional electrophysiological properties similar to those of neurons.

Example 3 Transplanted iENPs Integrate and Differentiate in Rat Brains

Figure 5M:
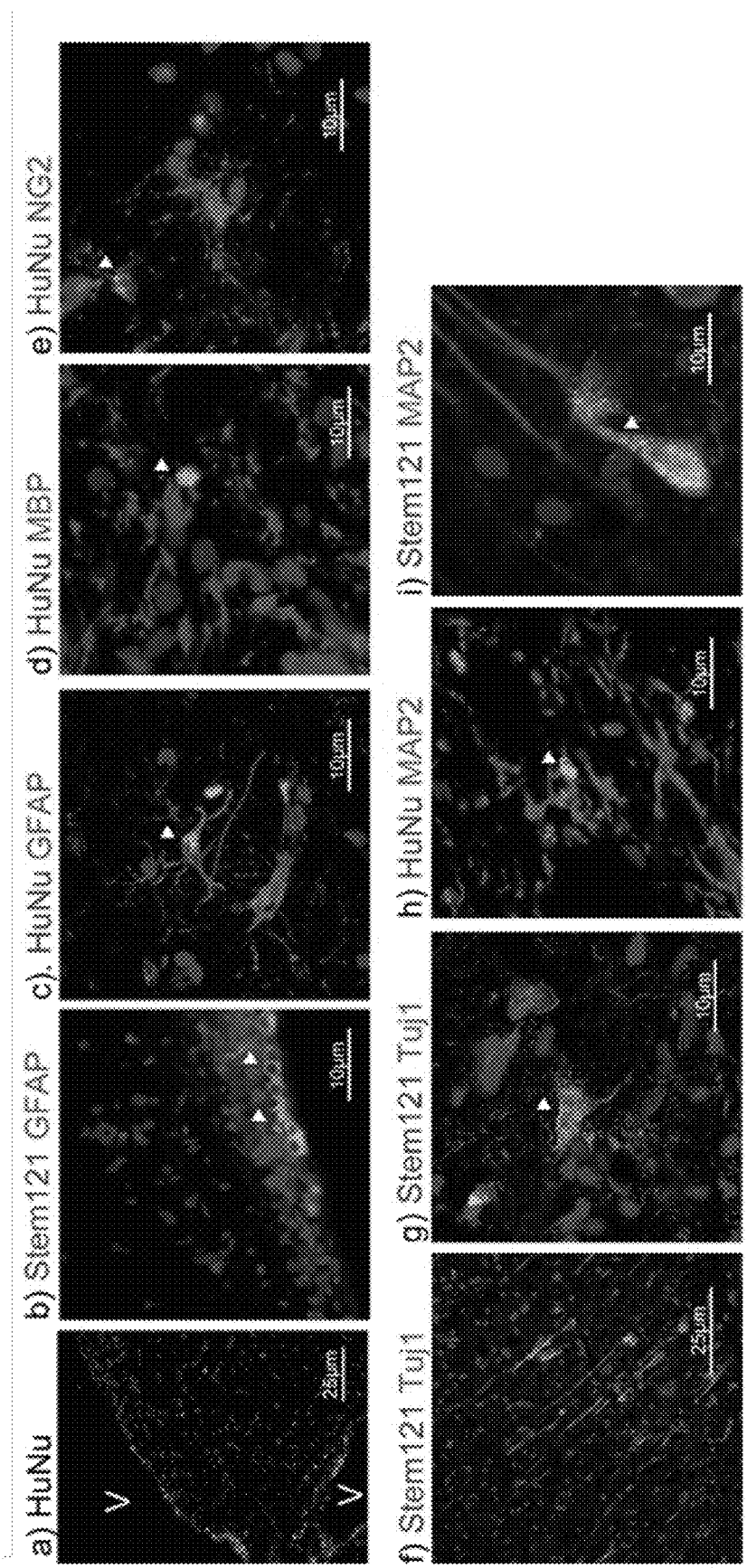

To assess the in vivo differentiation potency of iENP, we transplanted the iENPs into the corpus callosum of rat brains, and analyzed the brains 12 weeks after transplantation (FIGS. 3P and 5M). We first examined whether iENP transplantation caused tumor formation in the brain. H&E staining of brain sections and further RT-PCR and IHC analyses revealed no expression of tumor-associated markers or tumor formation in iENP-transplanted brains at 12 weeks post transplantation (FIG. 9). Interestingly, we found some of the transplanted cells migrated to the ventricular zones, a brain region where neurogenesis takes place, and GFAP, a radial glia progenitor marker, is expressed (FIG. 3P, Panels a-b; and FIG. 5M, Panels a -b). Consistent with the in vitro differentiation results, the transplanted iENPs were found to have differentiated into GFAP$^+$ astrocytes (FIG. 3P, Panel c; and FIG. 5M, Panel c), NG2$^+$ oligodendrocytes (FIG. 3P, Panels d-e; and FIG. 5M, Panels d-e), and TUJ1$^+$ or MAP2$^+$ neurons (FIG. 3P, Panels f and i) in the brains.

Together, our results indicate that iENPs integrate into adult brain tissue and differentiate into major neural cell types in vivo.

Figure 6A:
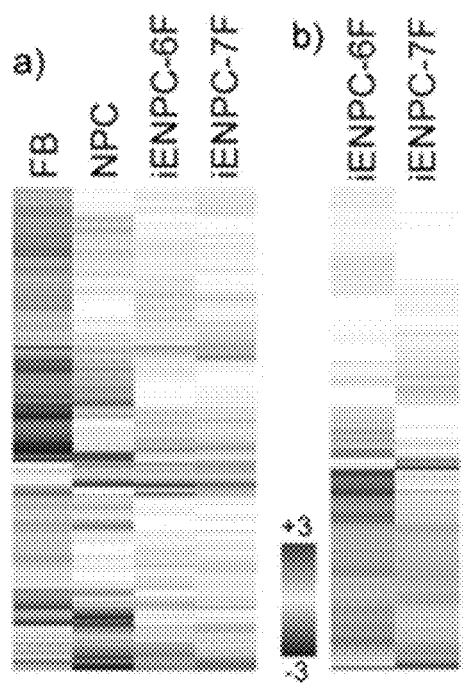
Figure 6B:
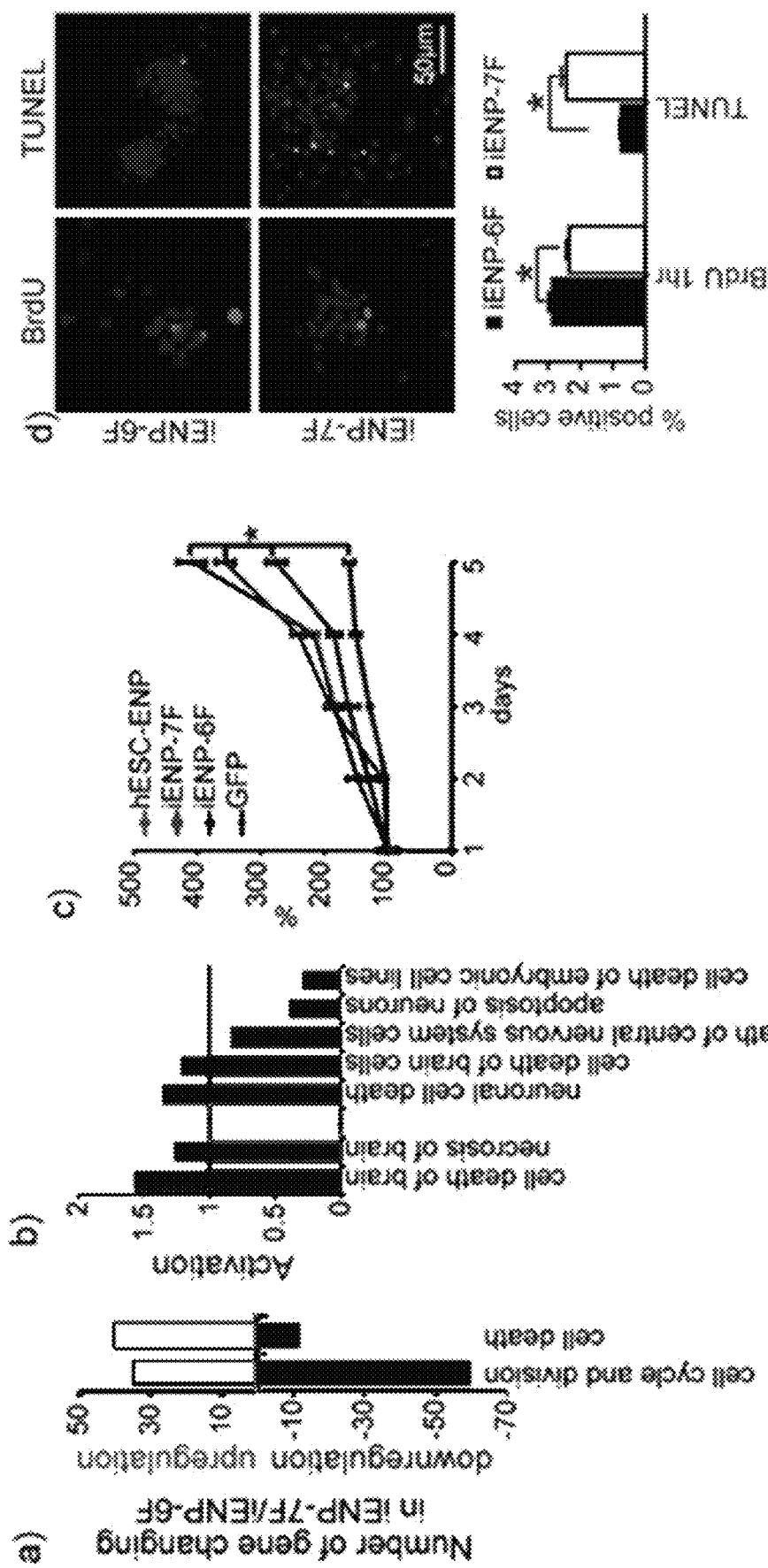

Example 4 the iENP-6F and -7F Populations Exert Differential Developmental Propensity As described above, our results indicated that iENP-6F and -7F possess different neural differentiation propensity. This observation prompted us to further explore the differences between these two populations. To this end, we first examined the gene expression profiles of these two iENP populations by microarray analysis. Heatmap analysis revealed that the global gene expression profiles of iENP-6F and -7F are similar (FIG. 6A, Panel a). Through IPA analysis and examination of combined fold change and gene ontology, the expression levels of 170 genes were found significantly different (>2 folds) between iENP-6F and -7F (FIG. 6A, Panel b). Of these, a panel of genes related to cell cycle and division exhibited lower expression in iENP-7F than in iENP-6F (FIG. 6B, Panel a) and IPA analysis showed the activation of cell death-associated pathways were activated in iENP-7F as compared to iENP-6F (FIG. 6B, Panel b). Consistently, the growth curve of iENP-6F was found to be similar to that of hESC-ENPs, whereas iENP-7F exhibited a slower proliferation rate (FIG. 6B, Panel c). Further analysis showed greater BrdU$^+$ and reduced TUNEL$^+$ proportions in iENP-6F as compared to iENP-7F (FIG. 6B, Panel d).

Figure 6C:
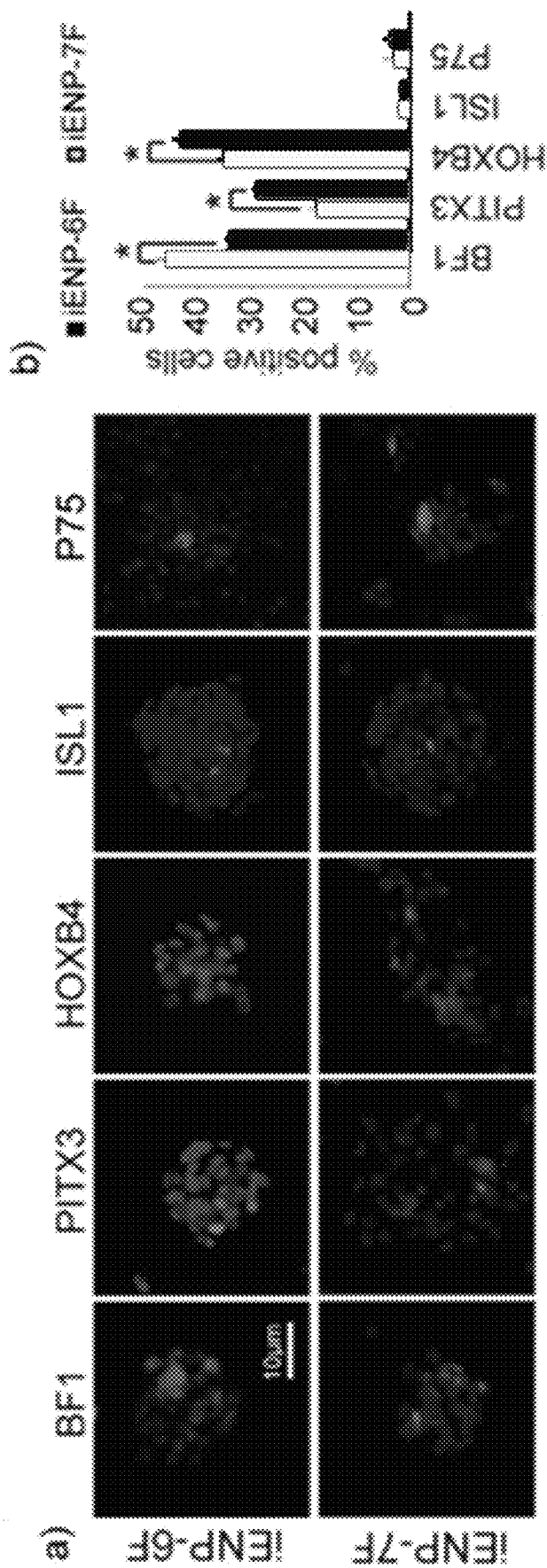
Figure 6D:
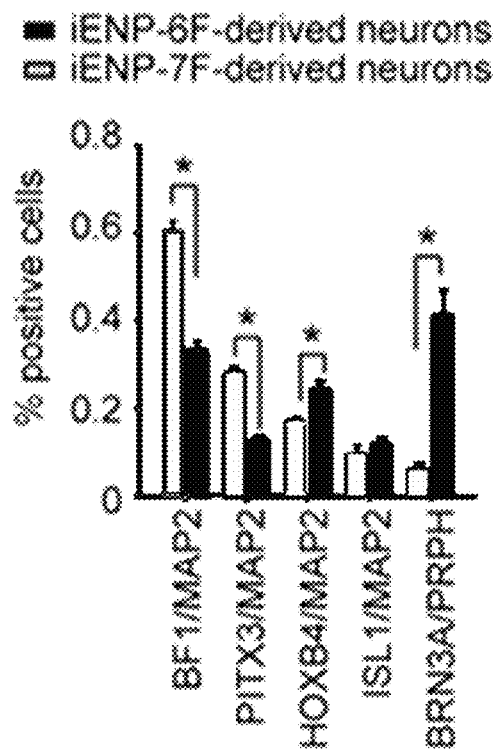
Figure 6E:
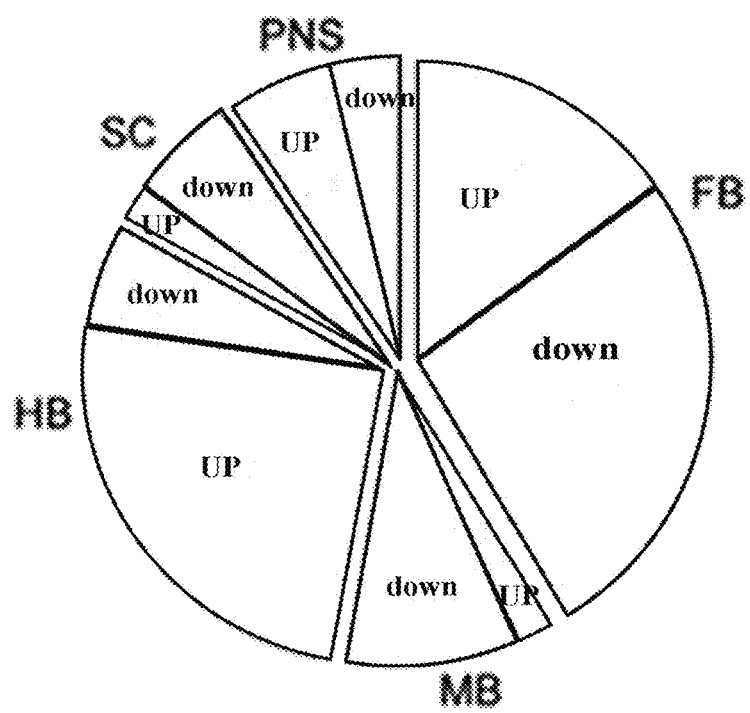
Figure 6F:
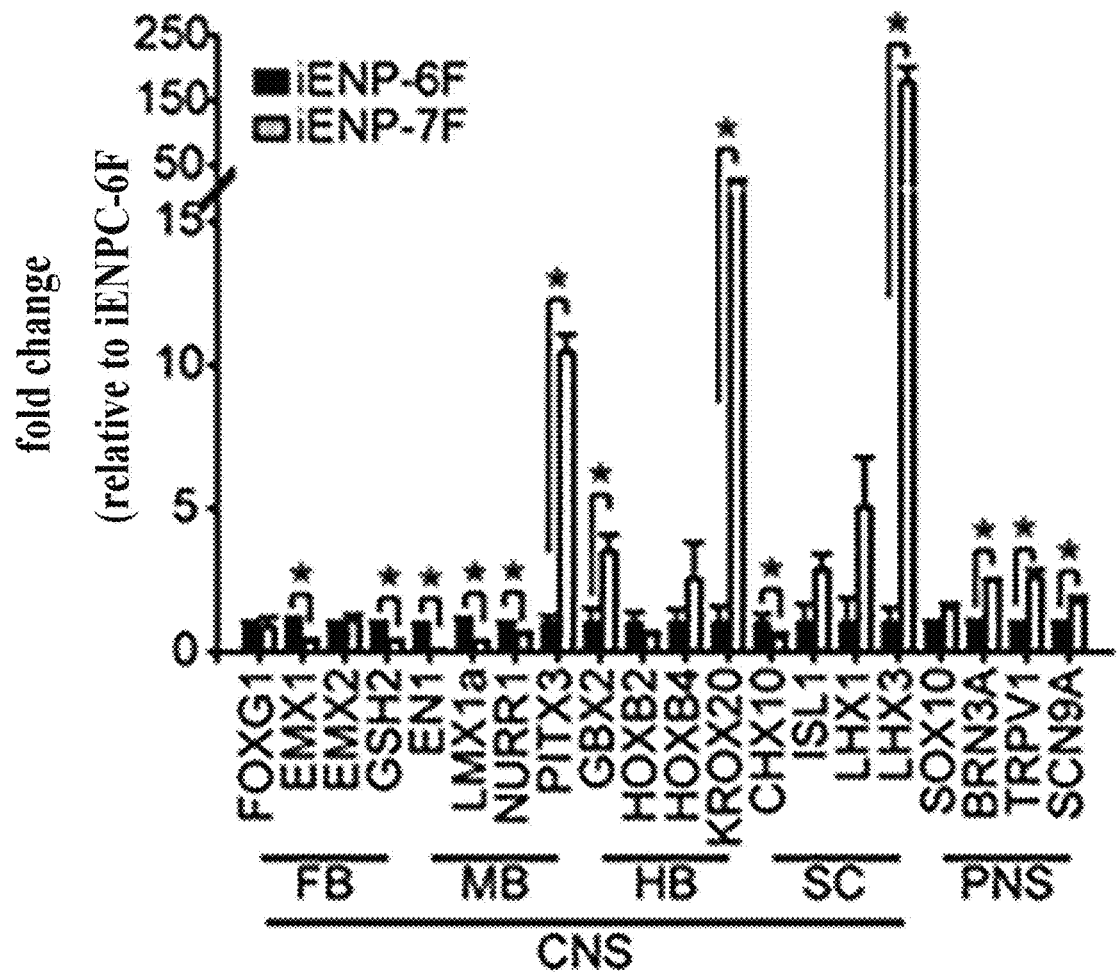

To further explore the developmental propensity of iENP-6F and -7F, we interrogated these populations with a panel of regional markers (FIG. 6C, Panel a). ICC analysis of the undifferentiated iENP populations and their derived neurons (iENP-Ns) revealed that the proportion of iENPs/iENP-Ns expressing BF1 (forebrain marker) was significantly higher in iENP-6F/-Ns than in iENP-7F/-Ns, whereas the proportion of cells expressing PITX3 (midbrain marker), HOXB4 (hindbrain marker), and p75 or BRN3A (PNS marker), were lower in iENP-6F/-N than in iENP-7F/-N (FIG. 6C, Panel b; and FIG. 6D). Consistent with our ICC analysis, comparative global gene expression profiling and RT-qPCR analysis between iENP-6F and 7F revealed that iENP-6F preferentially expressed more forebrain, midbrain, and spinal cord-related genes as compared to iENP-7F, whereas iENP-7F preferentially expressed more hindbrain and PNS-related genes as compared to iENP-6F (FIGS. 6E and 6F). Together, these results suggest that iENP-6F and -7F are different NP subpopulations, which possess different neural gene expression, growth rates and developmental propensities.

Example 5 Recapitulation of Pathological Features in Diseased iENPs

Figure 7A:
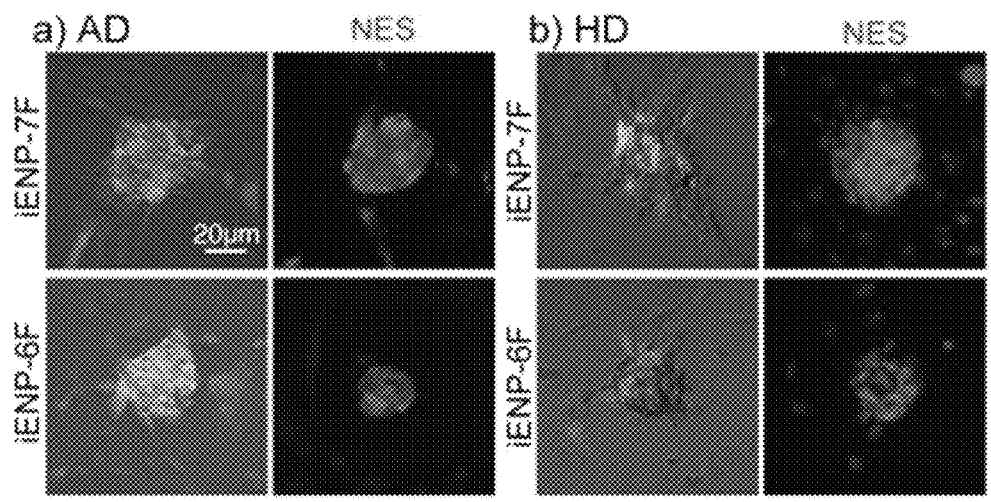
Figure 7B:
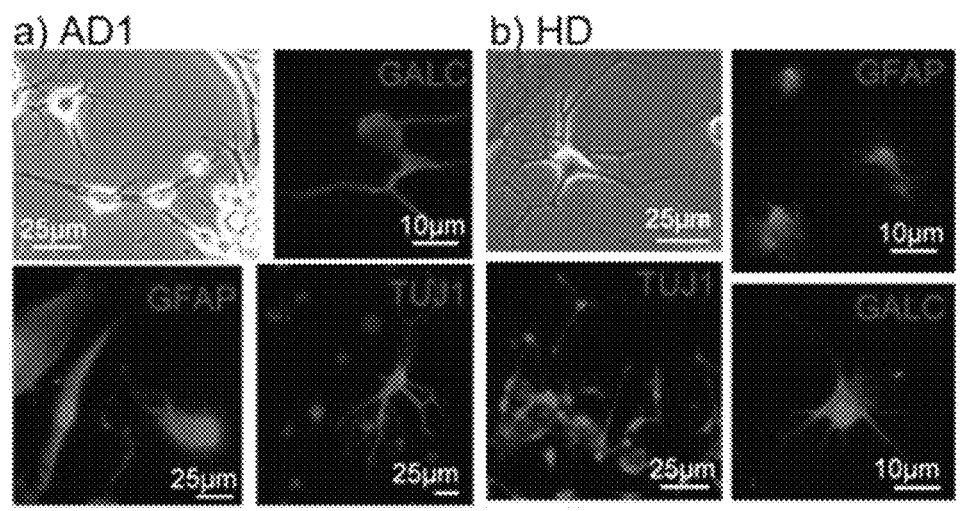
Figure 7C:
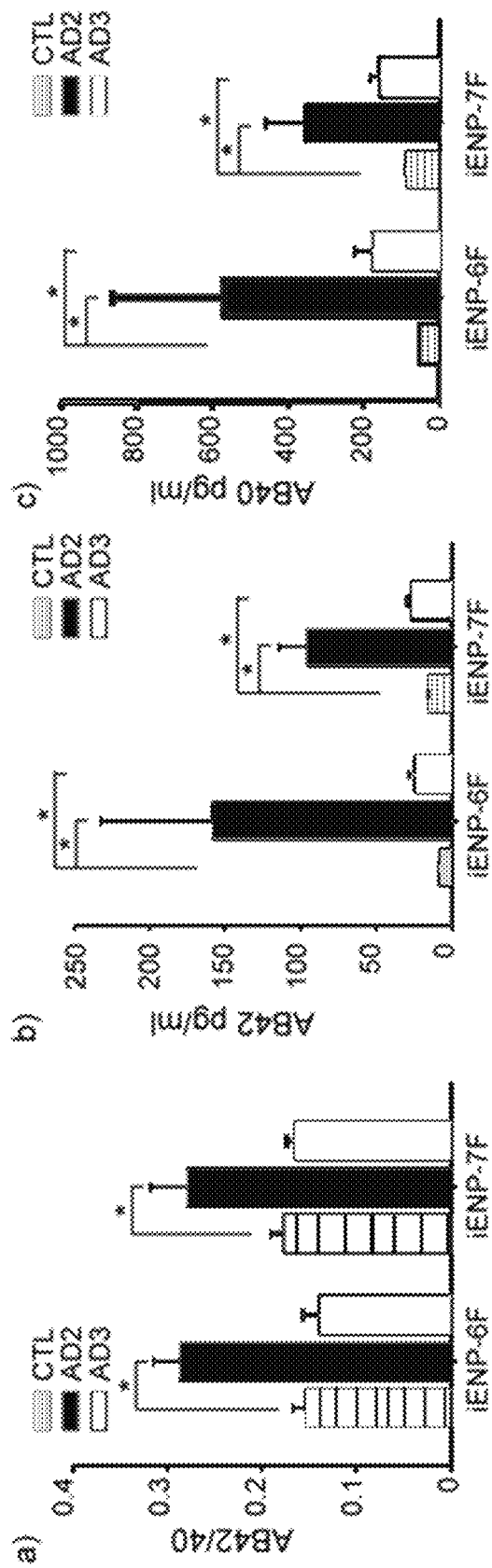

To explore the potential of iENPs for disease modeling, we generated iENPs from FBs derived from an AD patient with an APOE4/E4 mutation (AD1), and two familial AD (fAD) patients with the PSEN1 mutation (fAD, AD2 and AD3) and two HD patients (male and female, 41 CAG repeats in HTT gene). Similar to wild-type FBs, AD- and HD-FBs could be converted into PAX6:EGFP- and SOX1: EGFP$^+$ cells with the 6-TF or 7-TF combination (FIG. 12A), respectively, and these populations formed neural sphere-like structures and expressed NP markers/genes (FIGS. 7A and 12B-12C). Further, we showed that the putative AD- and HD-iENPs were able to give rise to TUJ1$^+$ neurons, GFAP$^+$ astrocytes, and GALC$^+$ oligodendrocytes (FIG. 7B).

Figure 7D:
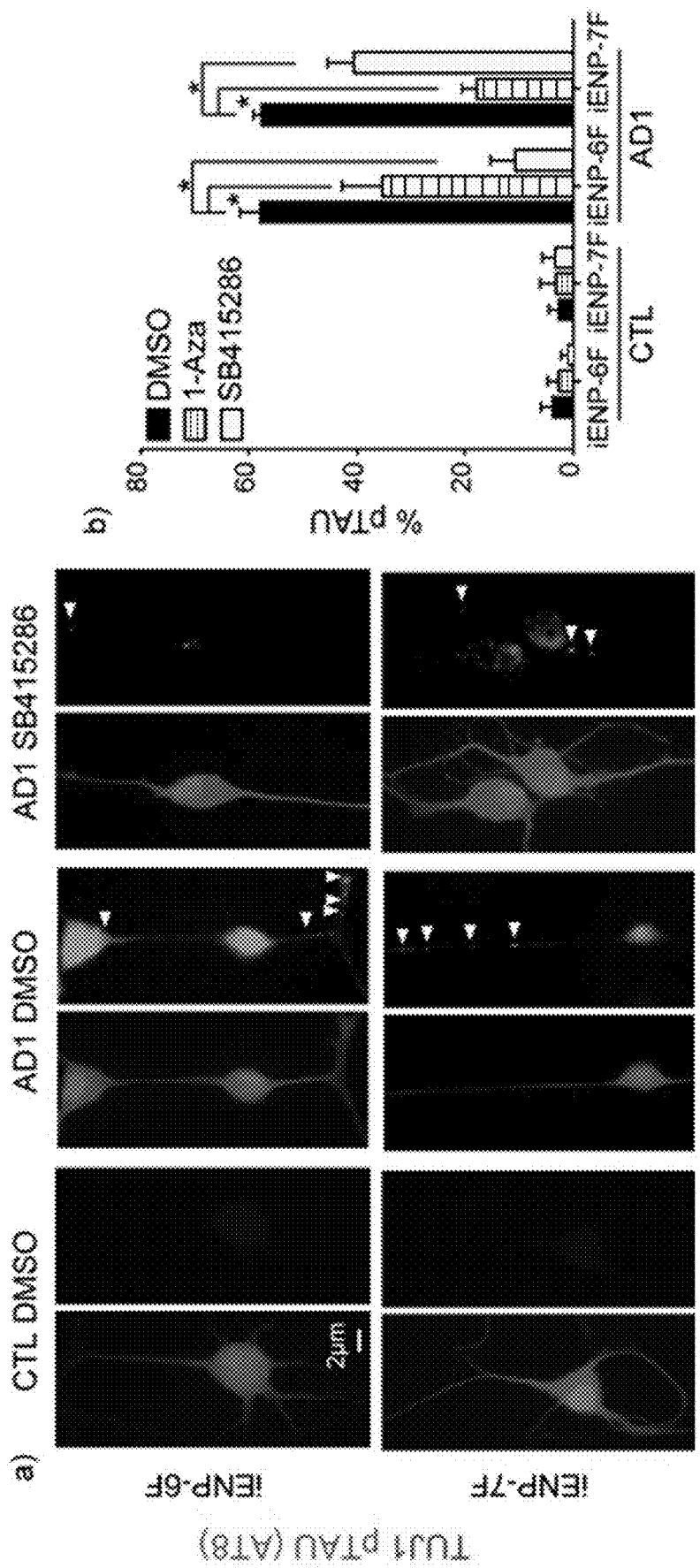

Next, we examined whether AD- and HD-iENP and their neuronal derivatives exhibit the pathological features of the relevant diseases. As an increase of Amyloid β (Aβ) and accumulation of phosphorylated TAU (pTAU) are the major pathological features present in the neurons of AD patient, we first measured the level of extracellular Aβ40 and Aβ42 in conditioned media of neurons differentiated from AD- or control-iENPs. The results of ELISA analysis revealed that the level of both AP isoforms was significantly elevated in the neurons of AD-iENP derived from two fAD-FB populations with the PSEN1 mutation (AD2 and AD3, FIG. 7C) as compared to the control-iENP-derived neurons. The Aβ42/Aβ40 ratio was also increased in the fAD-iENP-derived neurons induced from fAD-FBs with the PSEN1 E184D mutation (AD2), although no significant increase in the Aβ42/Aβ40 ratio was detected in the fAD-iENP-derived neurons induced from another fAD-FB population with the PSEN1 P264L mutation (AD3), which was previously reported to be associated with a slight increase in the Aβ42/Aβ40 ratio in PSEN1 P264L-overexpressing cells. To investigate pTAU pathologies in the AD-iENP-derived neurons, we first subjected AD1- and control-iENP-derived neurons to ICC analysis with an antibody recognizing pTAU (AT8); in this way, we readily detected pTAU in the processes of certain TUJ1$^+$ neurons, and observed patched pTAU aggregates in the cell body of AD-iENP-derived neurons, as previously reported in AD patients' cortex and AD-iPS-derived neurons (FIG. 7D, Panel a). In addition, treatment of AD-iENP-derived neurons with GSK3β inhibitors (SB415286 and 1-Aza) significantly reduced pTAU aggregation as compared to DMSO-treated and control-iENP-derived neurons (FIG. 7D).

Figure 7E:
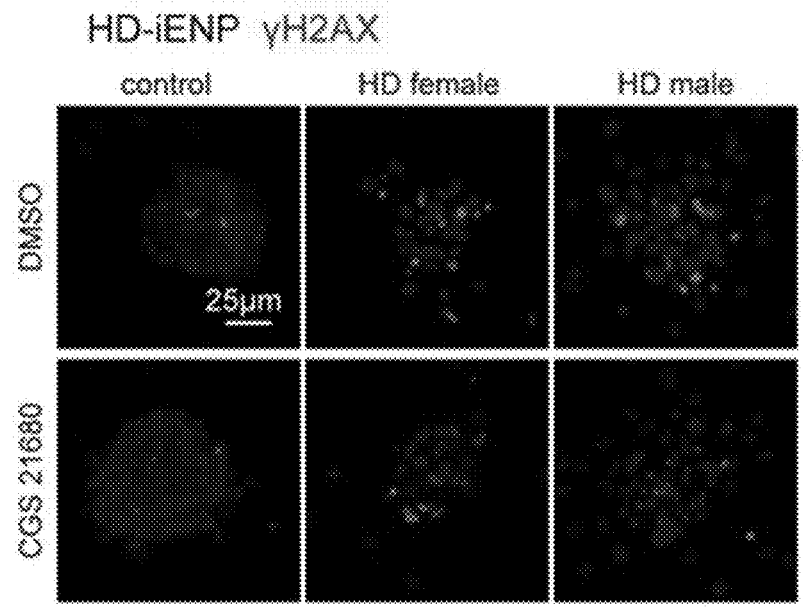
Figure 7E:
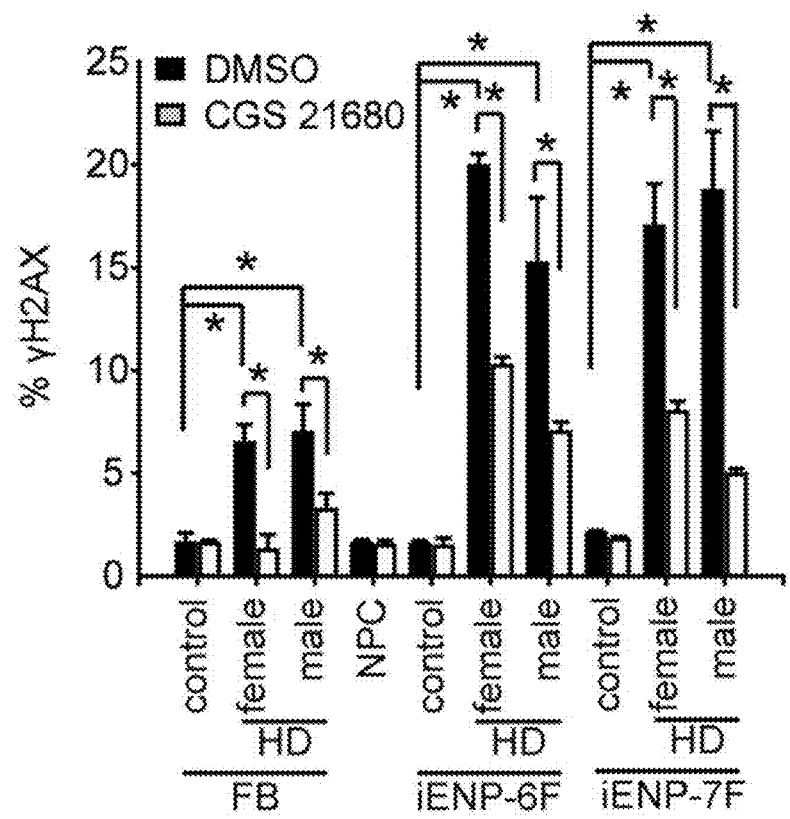
Figure 7E:
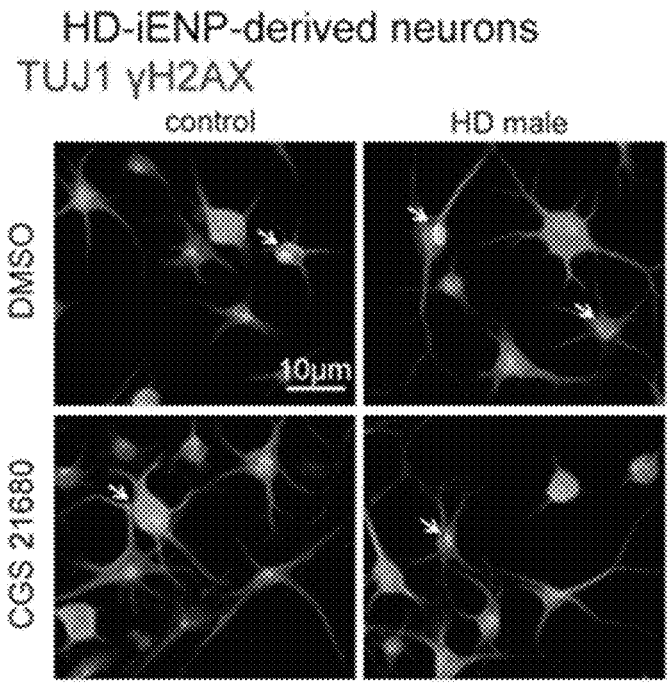
Figure 7E:
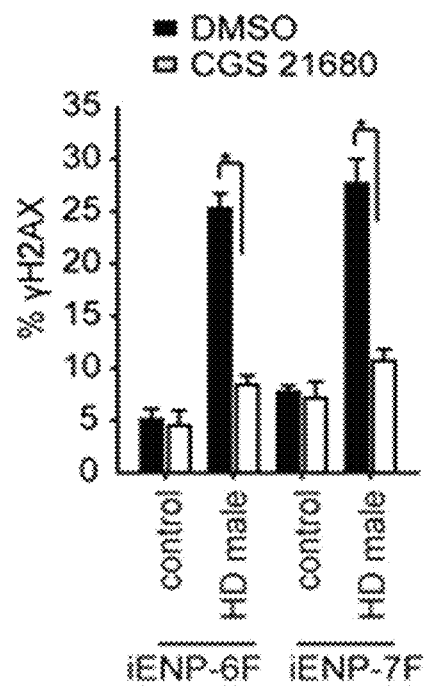

We previously reported that HD-iPSC-derived neurons are vulnerable to DNA damage, and that stimulation of $A_{2A}R$ using selective agonists reduced DNA damage in HD-iPSC-derived neurons. To identify whether the HD-iENPs and their neuronal derivatives recapitulate the above features of HD, we treated HD-iENPs and control-iENPs with a selective $A_{2A}R$ agonist, CGS21680. ICC analysis of the expression of phosphorylated γH$_2$AX, a hallmark feature of DNA damage, revealed that the number of γH$_2$AX$^+$ nuclei is significantly higher in HD-iENPs and their neuronal derivatives as compared to their counterparts derived from control cells (FIG. 7E). Furthermore, CGS21680 stimulation significantly decreased γH$_2$AX expression in the HD-iENPs and their neuronal derivatives, suggesting that activation of $A_{2A}R$ might reduce DNA damage in these cells (FIG. 7E, Panels b and d). Taken together, these results reveal that the diseased iENPs and their neuronal derivatives recapitulate the pathological features of AD and HD.

Previously, various TF combinations have been used to directly convert FBs into iNPs. These iNPs possessed the general properties of neural progenitors, such as neural marker/gene expression, proliferation, and differentiation propensity. Unlike the hESC-ENPs, which were demonstrated to differentiate into both CNS and PNS lineages, previous reported iNPs exhibited developmental potentials primary toward CNS subtypes. However, studies have rarely addressed whether these iNPs possess the ability to give rise to PNS neuron subtypes. In this study, we showed that iENP-6F and iENP-7F are able to differentiate into not only CNS lineages, but also PNS lineages. Furthermore, they responded to the same extracellular stimuli as hESC-ENP and give rise to specific neuronal subtypes. In line with these observations, genome-wide transcriptome profiling also confirmed a high similarity between the FB-induced ENP and their hESC-derived counterparts. Thus, our results suggest that the iENP population reprogrammed by the hESC-ENP-TFs may be more similar to embryonic NPCs than adult brain-derived NPCs.

Although the two iENP populations generated in this study shared similar NP characteristics, further investigation revealed that they exhibit different functional features. First, our analysis demonstrated that iENP-6F exhibited higher proliferation and reduced apoptosis as compared to iENP-7F. Second, iENP-7F showed stronger differentiation potency toward neuronal lineages than glial lineages. Third, dissection of the neuronal differentiation potential of the iENP populations revealed that iENPs-7F have a regional preference toward caudal identity, whereas iENPs-6F have a regional preference toward rostral identity. The above differences between iENP-6F and 7F may be explained by the neural reporters used for the TF and iENP selection. We used two neural reporters, PAX6 and SOX1, to monitor and evaluate the efficiency of neural fate conversion by hESC-ENP-nTFs, through which we identified a 6- and 7-TF combination for iENP-6F and -7F induction, respectively. On the other hand, PAX6 and SOX1 were also used to select the iENP-6F and 7F populations, respectively. Thus, it is tempting to suggest that neural reporter selection may decide the functional characteristics of the resulting iENP populations. It is well-known that hESC-derived neural rosettes and neural epithelia consist of various ENSCs/ENPs, which are responsible for the subsequent neural development of central and peripheral nervous systems. Therefore, the originally selected 25 nTFs highly expressed in hESC-ENPs are likely essential for the formation of heterogeneous NP populations. Accordingly, induction of FBs with specific nTF combinations selected from the 25-TF pool should result in the formation of an iENP population with specific neural characteristics. Together, these results suggest that the scheme described in this study may provide an excellent way for generating desirable iENP populations through the selection of specific TF combinations from the original 25-TF pool and iENP populations using different neural reporters. Future studies will be required to determine whether specific combinations of hESC-ENP-nTFs can define the functional aspects of the resulting iENPs, and elucidate the mechanisms by which the TF combinations reprogram FBs into iENPs.

Previously, it has been reported that iNP can be directly converted from human or mouse FBs by TF combinations including all iPSC factor(s), only certain factors, or single. Starting from a panel of 25 TFs, we identified two TF combinations, 6 TFs and 7 TFs, which can induce FBs into iENPs. Overall, the functional aspects of the TFs used for iENP induction are associated with neural development or neural identity maintenance. In the 6-TF combination, the majority of the component TFs have been reported to be involved in neuronal differentiation and maintenance of NSC fates. In the 7TF combination, most TFs were reported to be associated with the early CNS, PNS development, and early neural regional specification. Unlike most of the reported TF sets used for iNP generation, none of the TFs identified by our strategy are functionally associated with human iPSC generation, suggesting the induction of iENPs from FBs does not require iPSC factors. Thus, this precludes the possibility that the iENPs were generated through a transient pluripotent state, thereby circumventing the increased tumorigenic risk associated with iPSC factors. Of note, two TFs, TFAP2A and ZFP42/REX1, were shared between both TF combinations. TFAP2A is well documented to participate in the development of many tissues during embryogenesis, especially in neural development. ZFP42/REX1 is expressed in ESCs and NPs, but is dispensable for mouse pluripotency. However, infection of cells with lentivirus encoding TFAP2A and ZFP42 did not result in the generation of iENPs (data not shown), suggesting they may be essential, but insufficient, to induce iENPs.

One of the advantages of iNP generation is that it provides a cell-based platform for neurodegenerative disease modeling and drug discovery. As proof of principle, we induced iENPs from the FBs of AD and HD patients, and demonstrated that the diseased iENPs and their neuronal derivatives exhibited pathological features of HD and AD. For example, our data showed a dramatic increase of Aβ variants and Aβ42/Aβ40 ratio and increased pTAU expression in the AD-iENPs-derived neurons; expression of pTAU could be reduced by GSK3β inhibitors, suggesting the AD-iENP-derived neurons recapitulate some, if not all, of the AD pathological features. Several lines of evidence indicated that stress factors can cause DNA damage and increase profound neuronal death in cells derived from HD patients. Also, it has been reported that $A_{2A}R$ agonists are beneficial in HD transgenic animal models and HD-iPSC-derived neuronal population. In line with these observations, our results demonstrated that HD-iENPs and their neuronal derivatives were more susceptible to DNA damage than their counterparts derived from normal FBs. Moreover, CGS21680 treatment decreased DNA damage in the HD-iENPs and their neuronal derivatives. Together, these findings suggest that, to some extent, the iENP model can recapitulate neurodegenerative disease-relevant pathogenesis, and thus may be suitable for characterization of the disease mechanism and for screening novel therapeutic agents.

Through in vivo transplantation of iENPs into rat brains, we demonstrated that iENPs can survive and differentiate into various neural subtypes in the adult brain environment. This observation confirms that iENPs possess an in vivo differentiation propensity similar to that of hESC-ENPs, suggesting that the iENPs established in this study could serve as an autologous cell source to treat neurodegenerative diseases, such as AD and HD. Nevertheless, further efforts are required to explore the tumorigenic potential of the transplanted iENPs in brains, although our results showed that brains are free from tumor formation at 12 weeks post-transplantation.

Collectively, our studies have demonstrated a novel paradigm for direct conversion of multipotent iENPs from human somatic cells through overexpression of hESC-NP-enriched TFs. This system will allow generation of expandable iNP populations with desirable neural differentiation propensities, and also facilitate the discovery of novel mechanisms and drugs for treatment of neurodegenerative diseases and use in regenerative medicine.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A kit for inducing a fibroblast cell into an induced embryonic neural progenitor (iENP) cell, comprising a first to a twenty-fifth polynucleotides and a reporter polynucleotide, wherein the first to the twenty-fifth polynucleotides respectively comprise the sequences of SEQ ID NOs: 1-25, and the reporter polynucleotide comprises the sequence of SEQ ID NO: 26 or 27.

2. The kit of claim 1, further comprising an enhancer selected from the group consisting of: RepSox, PP242, DZNep, vitamin C and a combination thereof.

* * * * *